(12) United States Patent
Pastini et al.

(10) Patent No.: US 8,637,080 B2
(45) Date of Patent: Jan. 28, 2014

(54) RUPTURING CONTROLLED RELEASE DEVICE COMPRISING A SUBCOAT

(75) Inventors: Ana C. Pastini, Buenos Aires (AR); Joaquina Faour, Buenos Aires (AR); Juan A. Vergez, Buenos Aires (AR); Marcelo A. Ricci, Buenos Aires (AR); Gustavo A. Fischbein, Buenos Aires (AR)

(73) Assignee: Osmotica Kereskedelmi és Szolgáltató, KFT, Budapest (HU)

( * ) Notice: Subject to any disclaimer, the term of this patent is extended or adjusted under 35 U.S.C. 154(b) by 1129 days.

(21) Appl. No.: 12/146,069

(22) Filed: Jun. 25, 2008

(65) Prior Publication Data

US 2009/0004229 A1   Jan. 1, 2009

Related U.S. Application Data

(60) Provisional application No. 60/946,845, filed on Jun. 28, 2007, provisional application No. 60/947,081, filed on Jun. 29, 2007.

(51) Int. Cl.
| | |
|---|---|
| A61K 9/00 | (2006.01) |
| A61K 31/5513 | (2006.01) |
| A61K 31/519 | (2006.01) |
| A61K 31/195 | (2006.01) |
| A61K 31/4422 | (2006.01) |
| A61K 31/403 | (2006.01) |
| A61K 31/55 | (2006.01) |

(52) U.S. Cl.
USPC ........... 424/473; 424/400; 514/356; 514/411; 514/517

(58) Field of Classification Search
None
See application file for complete search history.

(56) References Cited

U.S. PATENT DOCUMENTS

| | | | |
|---|---|---|---|
| 3,247,066 A | 4/1966 | Milosovich, Jr. | |
| 3,916,899 A | 11/1975 | Theeuwes et al. | |
| 3,952,741 A | 4/1976 | Baker | |
| 4,016,880 A | 4/1977 | Theeuwes et al. | |
| 4,271,113 A | 6/1981 | Luschen | |
| 4,904,474 A | 2/1990 | Theeuwes et al. | |
| 4,948,592 A | 8/1990 | Ayer et al. | |
| 4,986,987 A | 1/1991 | Ayer et al. | |
| 5,141,752 A | 8/1992 | Ayer et al. | |
| 5,190,765 A | 3/1993 | Jao et al. | |
| 5,431,920 A * | 7/1995 | Bechard | 424/480 |
| 5,516,527 A | 5/1996 | Curatolo | |
| 5,681,584 A | 10/1997 | Savastano et al. | |
| 5,792,471 A | 8/1998 | Curatolo | |
| 5,840,335 A | 11/1998 | Wenzel et al. | |
| 5,876,750 A * | 3/1999 | Jao et al. | 424/457 |
| 6,146,662 A | 11/2000 | Jao et al. | |
| 6,210,712 B1 | 4/2001 | Edgren et al. | |
| 6,368,626 B1 | 4/2002 | Bhatt et al. | |
| 6,599,284 B2 | 7/2003 | Faour | |
| 6,764,697 B1 | 7/2004 | Jao et al. | |
| 7,011,850 B2 | 3/2006 | Geerke | |
| 2001/0031279 A1* | 10/2001 | Cruz et al. | 424/468 |
| 2002/0071866 A1 | 6/2002 | Geerke | |
| 2002/0086054 A1 | 7/2002 | Shaw | |
| 2003/0175346 A1 | 9/2003 | Billotte et al. | |
| 2005/0008702 A1* | 1/2005 | Faour et al. | 424/473 |
| 2005/0089570 A1 | 4/2005 | Cruz et al. | |
| 2005/0136113 A1 | 6/2005 | Bhatt et al. | |
| 2005/0158382 A1 | 7/2005 | Cruz et al. | |
| 2005/0163850 A1 | 7/2005 | Wong et al. | |
| 2005/0208132 A1 | 9/2005 | Sathyan et al. | |
| 2005/0220879 A1 | 10/2005 | Geerke | |
| 2005/0260264 A1 | 11/2005 | Edgren et al. | |
| 2006/0204578 A1 | 9/2006 | Vergez et al. | |
| 2006/0251721 A1 | 11/2006 | Cruz et al. | |

FOREIGN PATENT DOCUMENTS

| | | |
|---|---|---|
| EP | 0378404 | 7/1990 |
| WO | WO0152819 | 7/2001 |
| WO | WO2007057762 A1 | 5/2007 |

OTHER PUBLICATIONS

Product Specification sheet (OPADRY YS-1-7006) from supplier COLORCON (3 pages).

* cited by examiner

*Primary Examiner* — Scott Long
*Assistant Examiner* — Sarah Alawadi
(74) *Attorney, Agent, or Firm* — Rick Matos; Innovar, L.L.C.

(57) ABSTRACT

The present invention provides a simple and improved rupturing controlled release device that is capable of providing a controlled release of active agent contained in the core first through a preformed passageway and then through an in situ formed second passageway into an environment of use in a standardized release profile manner. The rupturing controlled release device comprises a core comprising at least one drug and at least one osmopolymer, a semipermeable membrane enclosing the core and having at least one preformed passageway there through, wherein the semipermeable membrane ruptures during use to form a second passageway in the semipermeable membrane at a location spaced away from the preformed passageway, and a release-controlling subcoat between the core and the semipermeable membrane.

43 Claims, 11 Drawing Sheets

Frequency of formation of small and large ruptures of the carvedilol tablets according to Example 5

Average release profile of 12 carbamazepine tablets prepared according to Example 6

RUPTURING CONTROLLED RELEASE DEVICE COMPRISING A SUBCOAT

CROSS-REFERENCE TO EARLIER FILED APPLICATION

This application claims the benefit of U.S. Provisional Application Ser. No. 60/946,845 filed Jun. 28, 2007 and No. 60/947,081 filed Jun. 29, 2007, the entire disclosures of which are hereby incorporated by reference.

FIELD OF THE INVENTION

This invention pertains to a delivery device for the controlled delivery of a maximum amount of active agent to an environment of use. More particularly, it pertains to a controlled release drug delivery device comprising a semipermeable membrane that ruptures during use, at least one preformed passageway, and a subcoat between the core and the semipermeable membrane that provides standardized release profiles.

BACKGROUND OF THE INVENTION

The U.S. Pat. No. 6,599,284 to Faour discloses an osmotic device comprising an active agent and at least one excipient in the core, a semipermeable membrane surrounding the core and comprising a preformed passageway that increases in size during use and an optional scored region of the membrane adjacent the passageway. The preformed passageway is larger after use than it is prior to use of the osmotic device, and the internal pressure of the device increases during use causing a membrane edge defining the passageway to rupture.

U.S. Pregrant Publication No. 2005/0008702 to Faour and Vergez discloses a coated controlled release device, wherein the coating surrounding the core of the device ruptures forming a second passageway during use, due to a buildup of internal pressure, thereby allowing controlled delivery of an active substance contained in the core of the device to an environment of use.

The benefits provided by the rupturing devices disclosed in the U.S. Pat. No. 6,599,284 and the U.S. Pregrant Publication No. 2005/0008702 include: 1) approximately complete delivery of the active substance contained in the core; 2) an increased release rate of active substance during use as the second passageway permits additional contents of the core to be released more quickly than would occur through just the preformed passageway alone; and 3) enablement of the release of large particle size and/or generally insoluble active agents.

Osmotic devices containing a layer between the membrane and the interior compartment have been disclosed in the art to provide means for a variety of purposes, e.g. for easy control of the depth of penetration of a laser beam during formation of at least one exit orifice in a dosage form (U.S. Pat. No. 7,011,850 and Pregrant Publication No. 20050220879, both to Geerke); to promote the flow between the semipermeable wall and the drug layers (U.S. Pat. No. 6,368,626 to Bhatt, et al.); to protect a formulation comprising a drug and to increase the fluid-transmission rate into the dosage form to maintain the linear drug release over time (U.S. Pat. No. 6,210,712 to Edgren, et al.); to delay the release of the drug from the core (U.S. Pat. No. 6,764,697, No. 6,146,662 and No. 5,190,765, all to Jao, et al., U.S. Pat. No. 5,141,752, No. 4,986,987 and No. 4,948,592, all to Ayer, and U.S. Pat. No. 4,904,474 to Theeuwes); to provide protection for an antiepileptic drug from the pH of 1 to 8 of the gastrointestinal environment and to give the wall support against the stress and the strain of a fluid moving gastrointestinal tract (U.S. Pat. No. 5,876,750 to Jao, et al.); as an osmotic layer comprising hydrophilic polymer having a molecular weight of about 1,000,000 to about 15,000,000 (U.S. Pregrant Publication No. 20050220879 to Geerke); as a flow-promoting layer that facilitates release of drug from the dosage forms of the invention by reducing the frictional forces between the semipermeable wall and the outer surface of the drug layer, thus allowing for more complete delivery of drug from the device (U.S. Pregrant Publications No. 20050136113 to Bhatt, et al., No. 20060251721, No. 20050158382, and No. 20050089570, all to Cruz, et al., No. 20050260264 to Edgren, et al., and No. 20050208132 to Sathyan, et al.)

It has now been found that the variability in the release profile of a controlled release drug delivery device comprising a semipermeable membrane that ruptures during use can be restricted by adding a subcoat between the core and the semipermeable membrane.

SUMMARY OF THE INVENTION

The present invention overcomes some of the disadvantages of the prior art by providing a rupturing controlled release device comprising: a) a core comprising at least one active agent and at least one excipient, b) a semipermeable membrane surrounding the core and comprising at least one preformed passageway that ruptures in a membrane edge defining the at least one passageway due to the increase of the internal pressure during use of the device, and is larger after use than it is prior to use of the device, c) an optional scored region of the membrane adjacent the passageway, and d) a rupture-controlling subcoat between the core and the semipermeable membrane. Some embodiments of the invention provide a rupturing controlled release device comprising: a) a core comprising at least one active agent and at least one excipient; b) a semipermeable membrane enclosing the core and comprising a weakened region and at least one preformed passageway there through; and c) a rupture-controlling subcoat between the core and the semipermeable membrane, wherein the semipermeable membrane ruptures at the weakened region during use due to the increase of the internal pressure of the device.

By rupture-controlling subcoat is meant a subcoat that controls the extent of rupture of the semipermeable membrane during operation of the device. The rupture-controlling subcoat can also provide control of drug release from the core, in which case the rupture-controlling subcoat is also a release-controlling subcoat. In some embodiments, the subcoat reduces variability in the drug release profile for drug released from the core, wherein the variability is determined on an osmotic device to osmotic device basis, a batch-to-batch basis, or a lot-to-lot basis. Due to the decreased variability in the drug release profile, for release of drug from the core, the subcoat provides a reproducible drug release profile that varies less than 15%, less than 10%, or less than 5%.

The present invention also overcomes some of the disadvantage of the prior art by providing a rupturing controlled release device comprising: a) a core comprising at least one active agent and at least one excipient, b) a semipermeable membrane enclosing the core and at least one preformed passageway there through, wherein the semipermeable membrane ruptures during use due to the increase of the internal pressure of the device to form a second passageway by breakage of the semipermeable membrane at a location spaced away from the preformed passageway, and c) a rupture-controlling subcoat between the core and the semipermeable membrane.

Another aspect of the present invention provides a rupturing controlled release device comprising: a) a core comprising alprazolam and at least one excipient, b) a semipermeable membrane enclosing the core and at least one preformed passageway there through, wherein the semipermeable membrane ruptures during use due to the increase of the internal pressure of the device to form a second passageway by breakage of the semipermeable membrane at a location spaced away from the preformed passageway, and c) a rupture-controlling subcoat between the core and the semipermeable membrane.

Another aspect of the present invention provides a rupturing controlled release device comprising: a) a core comprising sildenafil and at least one excipient; b) a semipermeable membrane enclosing the core and at least one preformed passageway there through, wherein the semipermeable membrane ruptures during use due to the increase of the internal pressure of the device to form a second passageway by breakage of the semipermeable membrane at a location spaced away from the preformed passageway; c) a rupture-controlling subcoat between the core and the semipermeable membrane wherein the subcoat comprises levodopa; and d) an external drug-containing coat wherein the drug is carbidopa.

Some embodiments of the invention include those wherein the rupturing controlled release device comprises: a) an inert water soluble or erodible coat composition surrounding the semipermeable membrane, b) an external drug-containing coat, c) two external drug-containing layers in stacked arrangement with respect to and on opposite sides of the controlled release device, d) one or more compression coatings and one or more sprayed-on coatings, e) one or more compression coatings and one or more sprayed-on membranes, f) two or more sprayed-on membranes, g) two or more sprayed-on coatings, h) two or more compression coatings, i) one or more coatings on the exterior of the semipermeable membrane, wherein the one or more coatings are independently selected at each occurrence from the group consisting of a drug-containing coating, a release rate modifying coating, a porous coating; a soluble coating, an insoluble coating, a semipermeable membrane; and a delayed release coating; j) alprazolam in the core; k) sildenafil in the core; and l) at least one osmopolymer in the core.

Some embodiments of the invention include those wherein: a) the core is a unitary core, a bi-layered core or a multi-layered core; b) the bi-layered core comprises the layers in stacked, substantially concentric or substantially eccentric arrangements; c) the bi-layered core comprises a nucleus comprising an inert composition comprising at least one swellable agent and a drug-containing layer surrounding the nucleus, d) the bi-layered core comprises a first layer comprising the active agent and a second layer comprising a swellable agent and an optional osmagent, e) the semipermeable membrane comprises at least one porosigen agent, f) a drug-containing coat surrounds the inert water soluble or erodible coat composition, g) the subcoat contains at least one active agent, h) the release rate of active agent increases over time during use, i) at least 80% of the active agent is released by the end of use.

The present invention further provides a method for treating a symptom, disorder and/or disease by the administration of a rupturing controlled release device comprising: a) a core comprising at least an active agent and at least one excipient, b) a semipermeable membrane surrounding the core and comprising at least one preformed passageway that ruptures in a membrane edge defining a passageway due to the increase of the internal pressure during use of the device, and is larger after use than it is prior to use of the device, c) an optional scored region of the membrane adjacent the passageway, and d) a rupture-controlling subcoat between the core and the semipermeable membrane.

The present invention further provides a method for treating a symptom, disorder and/or disease by the administration of a rupturing controlled release device comprising: a) a core comprising at least one active agent and at least one excipient, b) a semipermeable membrane enclosing the core and at least one preformed passageway there through, wherein the semipermeable membrane ruptures during use due to the increase of the internal pressure of the device to form a second passageway by breakage of the semipermeable membrane at a location spaced away from the preformed passageway, and c) a rupture-controlling subcoat between the core and the semipermeable membrane.

Some embodiments of the invention include those wherein: 1) the membrane ruptures more than about one hour or from one to twelve hours after exposure of the device to an environment of use; 2) the membrane ruptures in less than about one hour or within one min to 59 min after exposure of the device to an environment of use; 3) the membrane ruptures more than about three hours after exposure of the device to an environment of use; 4) the second passageway is smaller than or approximates the size of the at least one preformed passageway; 5) the second passageway is larger than or approximates the size of the at least one preformed passageway; 6) the at least one preformed passageway expands in size by rupture of the semipermeable membrane; 7) the at least one preformed passageway is disposed through the drug-containing coat; 8) the at least one preformed passageway is formed by mechanical means during manufacture of the osmotic device; 9) the at least one preformed passageway is plugged with a soluble material that dissolves during use of the osmotic device; 10) the extent to which the at least one preformed passageway increases in size is related to the viscosity, molecular weight or degree of substitution of the at least one excipient; 11) an increase in the viscosity, molecular weight, or degree of substitution of the at least one excipient is related to an increase in the extent to which the at least one preformed passageway increases in size; 12) the second passageway ranges in size from 0.3 to 1.49 mm, 1.5 to 2.99 mm, 3 to 6 mm, or 0.3 to 6 mm; and/or 13) the second passageway increases in size after initial formation.

Rupture formation generally begins at about 1 hour, 2 hours, 3 hours, 4 hours, 5 hours, 6 hours, 7 hours, 8 hours, 9 hours, 10 hours, 11 hours up to 12 hours after exposure of an osmotic device of the invention to an aqueous environment. In some embodiments, rupture formation occurs within 1 to 12 hours, within 1.5 to 12 hours, within 2 to 11 hours, within 2 to 10 hours, within 3 to 8 hours, within 3 to 9 hours, within 3 to 10 hours, within 4 to 8 hours, within 4 to 9 hours, or within 4 to 10 hours after exposure of the device to an aqueous environment.

Some embodiments of the invention include those wherein: 1) the subcoat ranges in thickness from 0.05 to 0.5 mm; 2) the subcoat comprises a water soluble and/or erodible polymer; 3) the subcoat comprises at least one active agent; and/or 4) the subcoat ranges in weight from 1 to 30 mg.

Some embodiments of the invention include those wherein the membrane ranges in thickness from 0.3 to 1.5 mm or 0.075 to 0.29 mm.

Some embodiments of the invention include those wherein: 1) the subcoat ranges in thickness from 0.05 to 0.2 mm, the membrane ranges in thickness from 0.075 to 0.29 mm and the extent of the rupture is about 3.00 mm or larger; 2) the subcoat ranges in thickness from 0.2 to 0.5 mm, the membrane ranges in thickness from 0.3 to 1.5 mm and the extent of the rupture is about 1.49 mm or smaller; 3) the subcoat ranges in thickness from 0.1 to 0.3 mm, the membrane ranges in thickness from 0.15 to 0.35 mm and the extent of the rupture ranges from 1.50 to 2.99 mm.

Different environments for use of the device include biological environments such as the oral, ocular, nasal, vaginal, glands, gastrointestinal tract, rectum, cervical, intrauterine, arterial, venous, otic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

The invention includes all combinations of the aspects, embodiments and sub-embodiments disclosed herein. Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1:
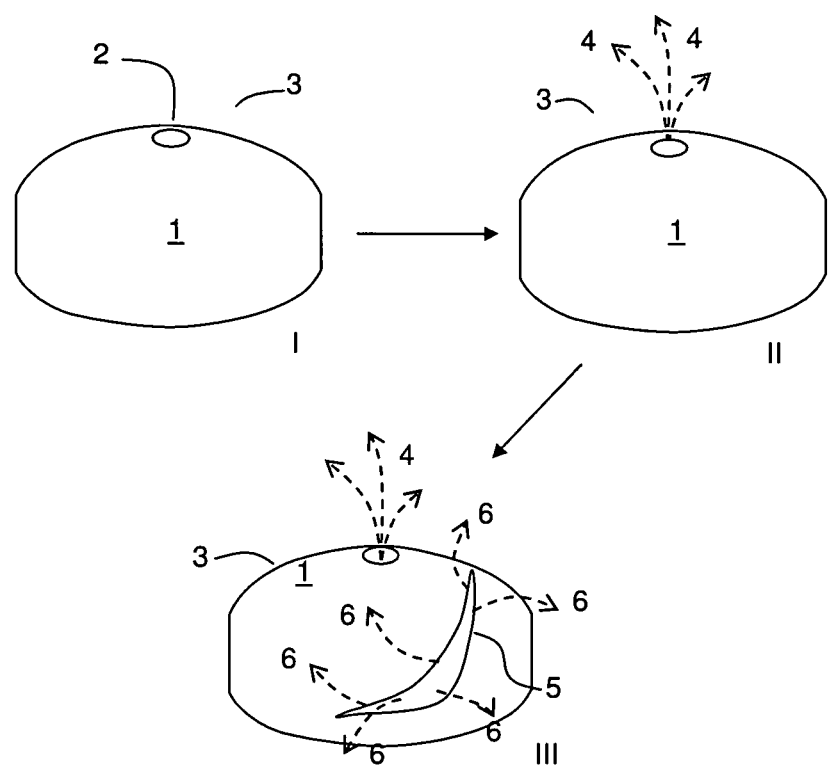
FIG. 1 depicts a perspective view of three general stages (I-III) of operation of a rupturing controlled release device according to Example 1.

By "environment" is meant an "environment of use", which is a locale in which a device of the invention is placed and into which the contents of the device (dosage form) are released. By "aqueous environment of use" is meant an environment of use containing an aqueous medium to which a device of the invention is exposed during use. The aqueous medium can be water, buffer, aqueous fluid, body fluid or other such medium. Exemplary aqueous environments of use include a subject, an assay fluid, or other similar environments. A subject can be human or non-human.

By "immediate release" is meant a release of an active agent to an environment over a period of seconds to no more than about 30 minutes once release has begun and release begins within a second to no more than about 15 minutes after administration.

By "rapid release" is meant a release of an active agent to an environment over a period of 1-59 minutes or 1 minute to three hours once release has begun and release can begin within a few minutes after administration or after expiration of a delay period (lag time) after administration.

By "controlled release" is meant a release of an active agent to an environment over a period of about eight hours up to about 12 hours, 16 hours, 18 hours, 20 hours, a day, or more than a day. A controlled release can begin within a few minutes after administration or after expiration of a delay period (lag time) after administration.

By "sustained release" is meant a controlled release of an active agent to maintain a constant drug level in the blood or target tissue of a subject to which the device is administered.

By "extended release" is meant a controlled release of an active agent from a dosage form to an environment over an extended period of time. As used herein, the term "extended release" profile assumes the definition as widely recognized in the art of pharmaceutical sciences. An extended release dosage form will release drug at substantially constant rate over an extended period of time or a substantially constant amount of drug will be released incrementally over an extended period of time. The term "extended release", as regards to drug release, includes the terms "controlled release", "prolonged release", "sustained release", or "slow release", as these terms are used in the pharmaceutical sciences.

A delayed but controlled release dosage form is one that provides a delayed release of a drug followed by a controlled release of the drug. By delayed release is meant any formulation technique wherein release of the active substance from the dosage form is modified to occur at a later time than that from a conventional immediate release product. In other words, the beginning of the controlled release of drug is delayed by an initial period of time. The period of delay is generally about 5 minutes to 10 hours, or 30 minutes to 10 hours, or 1 hour to 10 hours.

A zero-order release profile characterizes the release profile of a dosage form that releases a constant amount of drug per unit time. A pseudo-zero order release profile is one that approximates a zero-order release profile. A dissolution curve shows a zero or pseudo-zero order release profile if its release rate remains constant (or relatively constant within ±10% of the average value) in the interval of time $0 \leq a < t \leq b$. Any profile following the equation:

$$(M(t)/M_r) = k(t-a)^n \quad 0.9 \leq n \leq 1.1$$

has the following release rate equation:

$$(1/M)(dM/dt) = kn(t-a)^{n-1}$$

A sigmoidal release profile characterizes the release profile of a dosage form that releases a drug in a controlled manner but very slowly during a first release period, then more rapidly during a second release period and finally very slowly during a third release period such that the release profile resembles a sigmoid. A dissolution curve shows a sigmoid release profile within a certain interval of time $0 \leq a < t \leq b$ if its release rate reaches a single maximum within the interval (a, b) excluding the extremes. That is equivalent to consider a point of time T* so that the release rate is an increasing function of time for $a \leq t < T^*$ and a decreasing function of time, as determined by the following equation:

Weibull Function $$(M(t)/M_T) = W_{inf}\{1 - \exp\{-[(t-t_i)/\beta]^\alpha\}\} \text{Parameter ranges:}$$

$t_i$: between 0 and 3
$\beta$: between 7 and 12
$\alpha$: $1 < \alpha < 3$
Winf: between 0.5 and 1.1

A first order release profile characterizes the release profile of a dosage form that releases a percentage of a drug charge per unit time. A pseudo-first order release profile is one that approximates a first order release profile. A dissolution curve shows a first or pseudo-first order release profile within a certain interval of time $0 \leq a < t \leq b$ if its release rate is a continue monotone decreasing function of time. Specifically, a dissolution curve shows a first order profile whenever its release rate is proportional to the remaining undissolved amount of drug, as determined by the following equation:

$$(M(t)/MT) = 1 - \exp(-kt)$$

A dissolution curve shows a pseudo-first order profile when the drug release rate decreases with time as described by the Fickian or anomalous Fickian diffusion controlled release equation:

$$(M(t)/M_T) = kt^n, 0.3 \leq n \leq 0.7$$

By "unitary core" is meant the core of an osmotic device that is not divided into two or more layers or laminas. The core is considered to be the composition enclosed within the wall, e.g. semipermeable membrane, of the osmotic device. The ingredients of the core may be present as a heterogeneous mixture or homogeneous mixture. A homogeneous mixture is one wherein all of the ingredients have been thoroughly mixed such that the composition of the formulation is substantially the same throughout different portions of the core. The combined step of mixing and directly compressing the ingredients of the core generally provides a homogeneous mixture. A heterogeneous mixture is one wherein the ingredients of the core are divided into two or more groups that are processed separately to form two or more respective blends, at least one of which contains drug and at least one of which contains the osmagent. The blends are then mixed together and compressed to form the unitary core. A heterogeneous mixture can be obtained by wet granulation, dry granulation, pelleting or combinations thereof.

The terms "osmotic device" and "controlled release device" are generally used herein interchangeably. Basically, an osmotic device is a controlled release device that comprises a semipermeable membrane surrounding the drug-containing core, and optionally one or more other coatings and/or membranes. The preformed passageway is disposed at least through the semipermeable membrane. The core can be a unitary core and/or a single core, a bi-layered core or a multi-layered core. The layers in the core can be in stacked, substantially concentric or substantially eccentric arrangement. The core of the osmotic device can be a bi-layered core wherein the nucleus of the core is an inert composition containing swellable agents and the layer surrounding the nucleus is a drug-containing layer. The osmotic device can also comprise an inert water soluble or erodible coat composition surrounding the semipermeable membrane. The preformed passageway can be disposed through the inert water soluble or erodible coat composition and the semipermeable membrane. The semipermeable membrane can contain porosigen agents to provide the diffusion of the drug from the core through the membrane during use. The osmotic device can also comprise a drug-containing coat surrounding the inert water soluble or erodible coat composition. The osmotic device can also comprise two external drug-containing layers in stacked arrangement with respect to and on opposite sides of the osmotic device. A multi-layered osmotic device can comprise: 1) one or more compression coatings and one or more sprayed-on coatings; 2) one or more compression coatings and one or more sprayed-on membranes; 3) two or more sprayed-on membranes; 4) two or more sprayed-on coatings; or 5) two or more compression coatings.

By "osmotic pressure" is meant the hydrostatic pressure produced by a differential in the concentrations of solutes between the core and the external environment of use of the osmotic device.

By "swelling pressure" is meant the force build up by expansion of a swelling agent.

By "internal pressure" is meant an osmotic pressure and/or a swelling pressure.

FIG. 1 depicts three general stages (I-III) of operation of a controlled release device (1) according to Example 1. Stages I, II and III are illustrations of a general view of the device. The device comprises a core containing at least one active agent, and at least one excipient surrounded by a semipermeable membrane (3) which includes a preformed passageway (2). Stage I, the device is exposed to an aqueous environment of use. There is no or substantially no release of drug from the core through the preformed passageway. Stage II, the internal pressure starts to build up causing the beginning of the release of the active drug or core composition (4) through the preformed passageway such that active agent is released at a controlled rate over an extended period of time. Stage III, the internal pressure has built up sufficiently to cause rupture (5) of the semipermeable membrane (3) at a weakened region spaced away from the preformed passageway thereby forming a second passageway in the semipermeable membrane such that the active agent is release (6) at a controlled rate over an extended period of time. The composition in the core is then released through at least both passageways.

As used herein, the term "rupture" refers to breakage of the membrane such as by bursting, splitting, cracking, rending, severing, fracturing, tearing, cleaving, forcing open, puncturing, splitting, or ripping. The rupture occurs only to the extent that drug is still released from the core in a controlled release after rupture of the membrane. Rupture according to the invention does not include embodiments wherein the membrane breaks catastrophically thereby releasing the contents of the core in a burst or rapid manner. The mechanism of rupture, as used herein, is distinguished from mechanisms such as leaching, erosion or dissolution of material from the membrane, e.g. by inclusion of a pore-former in the membrane. The invention includes embodiments wherein the membrane ruptures even though it may also include a pore former.

Figure 2:
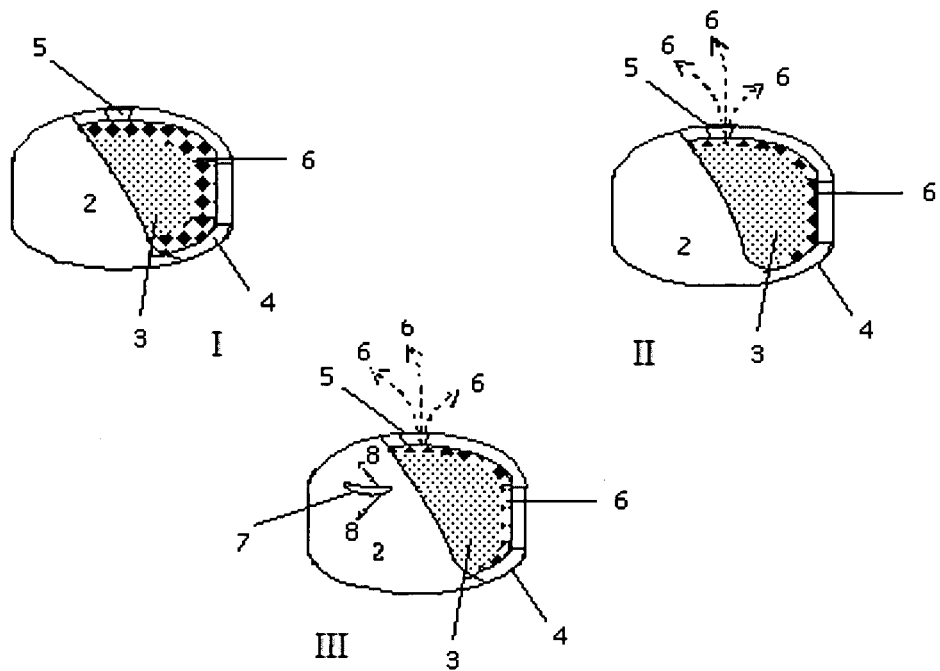
FIG. 2 depicts a partial sectional side view of three general stages (I-III) of operation of a rupturing controlled release device according to Example 2.

FIG. 2 depicts three general stages (I-III) of operation of a controlled release device (2) according to Example 2. Stages I, II and III are partial sectional views of the device of the invention with a portion of the semipermeable membrane removed to illustrate the structure of the device. The device comprises a core (3) containing at least one active agent, and at least one excipient surrounded by a semipermeable membrane (4), a preformed passageway (5), and a subcoat (6) between the core and the semipermeable membrane. Without being held bound to a particular mechanism of operation, it is believed that the osmotic device of the invention delivers one or more active agents to an environment of use as follows. Stage I, the device is exposed to an aqueous environment of use. There is no or substantially no release of drug from the core through the preformed passageway. Stage II, the internal pressure starts to build up causing the beginning of the release of the subcoat (6) composition through the preformed passageway meanwhile the core expands occupying the space left by the release of the subcoat (6) composition while exercising minimal internal pressure on the inner surface of the semipermeable membrane. Stage III, the core continues to expand and starts exercising sufficient internal pressure to cause the rupture (7) of the semipermeable membrane (4) at a weakened region spaced away from the preformed passageway, forming a second passageway in the semipermeable membrane, such that the active agent (8) is release providing less variable release profiles, in other words, providing standardized release profiles, as compared to the same osmotic device having no subcoat. The composition in the core is then released through at least both passageways.

One or more weakened regions can be included in the semipermeable membrane by: etching or scoring the membrane; shaping the osmotic device such that it has a shoulder, ridge, or border covered by the membrane and the membrane thickness at the shoulder, ridge or border is thinner than at a face adjacent the shoulder, ridge or border; including a brittling agent at one or more locations within or throughout the membrane; and/or applying the semipermeable membrane unevenly to the core or subcoat such that the membrane comprises one or more regions (weakened regions) that are thinner than the rest of the membrane. One or more weakened regions can be independently located adjacent or spaced away from one or more preformed passageways. The membrane may comprise one or two preformed passageways and one or two weakened regions. The membrane will comprise at least one preformed passageway and at least one weakened region.

Figure 3:
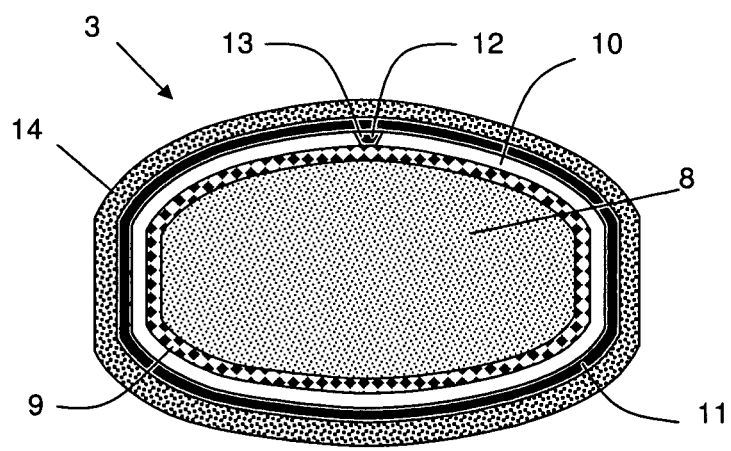
FIG. 3 depicts a sectional side view of a multi-layered rupturing controlled release device according to the invention.

The drug delivery device of the invention can operate as follows provided the right combination of materials is used to formulate the various coatings, the membrane and the core of the osmotic device. FIG. 3 illustrates an embodiment of the invention wherein the rupturing controlled release device (3) comprises a core (8) comprising at least one active agent and at least one excipient, a release-controlling subcoat composition (9) surrounding the core, a semipermeable membrane (10) that surrounds the subcoat composition (9), a polymer coat (11) surrounding the semipermeable membrane (10) and forming a plug (12) in the preformed passageway (13), and a water soluble, erodible and/or swellable external coat (14) which may contain an optional second active agent. In this embodiment, the semipermeable membrane was perforated by mechanical means, such as a laser, to form the preformed passageway (13) before applying the polymer coat (11). Following administration to a mammal, the water soluble, erodible and/or swellable external coat (14) begins to dissolve, erode, swell and/or detach from the osmotic device, thereby, releasing any second active agent contained in the external coat (14) into the stomach. As the rupturing controlled release device (3) of the invention moves through the gastrointestinal (GI) tract, portions of the external coat (14) will have partially or completely dissolved, eroded or become detached, thereby exposing the polymer coat (11), which in some embodiments is not soluble in acidic gastric juices. The polymer coat (11) then dissolves or erodes in one or more regions of the intestines according to the particular materials that comprise the polymer coat (11). For example, materials that are soluble in fluids having a pH of 4-6 will dissolve in the small intestine, whereas materials that dissolve in fluids having a pH of 7-8 will dissolve in the large intestine or colon. Combinations of these materials can be used. The polymer coat (11) can also be microporous to permit absorption of water into the core (8) of the rupturing controlled release device (3) without dissolution of the polymer coat (11). Once the polymer coat (11) has dissolved or eroded or once at least the plug (12) of the polymer coat (11) has dissolved or eroded, the core (8) will begin to release the subcoat composition (9) through the passageway (13) into the intestines due to the building up of the internal pressure until the pressure causes the rupture of the semipermeable membrane (10) at a weakened region spaced away from the preformed passageway, forming a second passageway in the semipermeable membrane (10), such that the drug is released providing less variable release profiles, in other words, providing standardized release profiles, as compared to the same osmotic device having no subcoat. The composition in the core is then released through at least both passageways.

Figure 4:
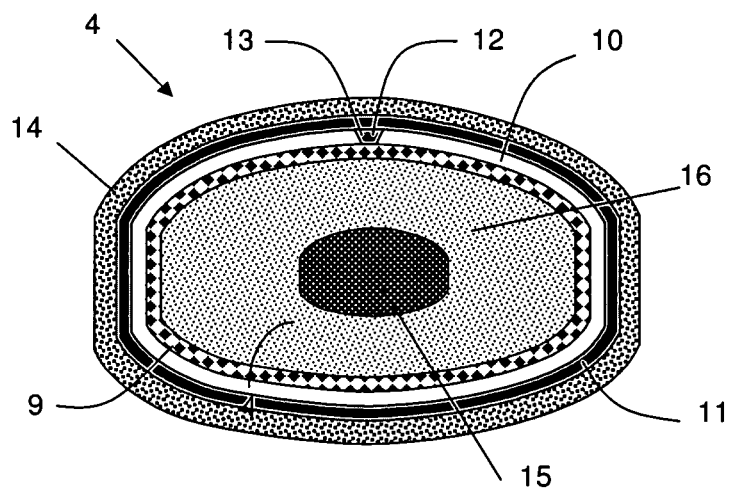
FIG. 4 depicts a sectional side view of a concentric layered core rupturing controlled release device according to the invention.

FIG. 4 illustrates an embodiment of the invention wherein the rupturing controlled release device (4) comprises a bi-layered core comprising a water swellable composition (15) surrounded by a drug-containing composition (16), a release-controlling subcoat composition (9) surrounding the core, a semipermeable membrane (10) that surrounds the subcoat composition (9), a polymer coat (11) surrounding the semipermeable membrane (10) and forming a plug (12) in the preformed passageway (13), and a water soluble, erodible and/or swellable external coat (14) which may contain an optional second active agent. In this embodiment, the semipermeable membrane was perforated by mechanical means, such as a laser, to form the preformed passageway (13) before applying the polymer coat (11). Following administration to a mammal, the water soluble, erodible and/or swellable external coat (14) begins to dissolve, erode, swell and/or detach from the osmotic device, thereby, releasing any second active agent contained in the external coat into the stomach. As the rupturing controlled release device (4) of the invention moves through the GI tract, portions of the external coat (14) will have partially or completely dissolved, eroded or become detached, thereby exposing the polymer coat (11), which in some embodiments is not soluble in acidic gastric juices. The polymer coat (11) then dissolves or erodes in one or more regions of the intestines according to the particular materials that comprise the polymer coat (11). As water permeates the internal osmotic pressure builds up and the water swellable second composition (15) swells and expands in size thereby forcing the first composition through the passageways and causing the rupture of the semipermeable membrane (10) at a region spaced away from the preformed passageway, forming a second passageway in the semipermeable membrane, such that the drug is release providing less variable release profiles, in other words providing more reproducible release profiles, as compared to the same osmotic device having no subcoat. The composition in the core is then released through at least both passageways. The extent to which the release of the active agent is controlled is known to depend upon a number of other variables such as the permeability of the semipermeable membrane, the magnitude of the osmotic pressure gradient, and the magnitude of the swelling pressure.

The expected maximum and minimum release profiles of the exemplary formulation of Example 1 are disclosed in Table I below.

TABLE I

| Time (h) | Range (%) | |
|---|---|---|
| | Min | Max |
| 0 | 0 | 0 |
| 1 | 0.8 | 1.9 |
| 4 | 7.5 | 41.1 |
| 8 | 30.9 | 71.6 |
| 12 | 46.4 | 86.6 |
| 15 | 57.0 | 92.8 |
| 24 | 72.4 | 93.7 |

The expected maximum and minimum release profiles of the exemplary formulation of Example 2 are disclosed in Table II below.

TABLE II

| Time (h) | Range (%) | |
|---|---|---|
| | Min | Max |
| 0 | 0 | 0 |
| 1 | 2.2 | 3 |
| 4 | 18.6 | 31.4 |
| 8 | 42.9 | 58.8 |
| 12 | 60.0 | 77.7 |
| 15 | 67.1 | 82.1 |
| 24 | 77.4 | 87.5 |

The values set forth in the above tables are approximate numbers. Depending upon the conditions of measurement as well as the assay used to determine those values, they may have a standard deviation of +/−2%, +/−5% or +/−10% of the indicated value.

Figure 5:
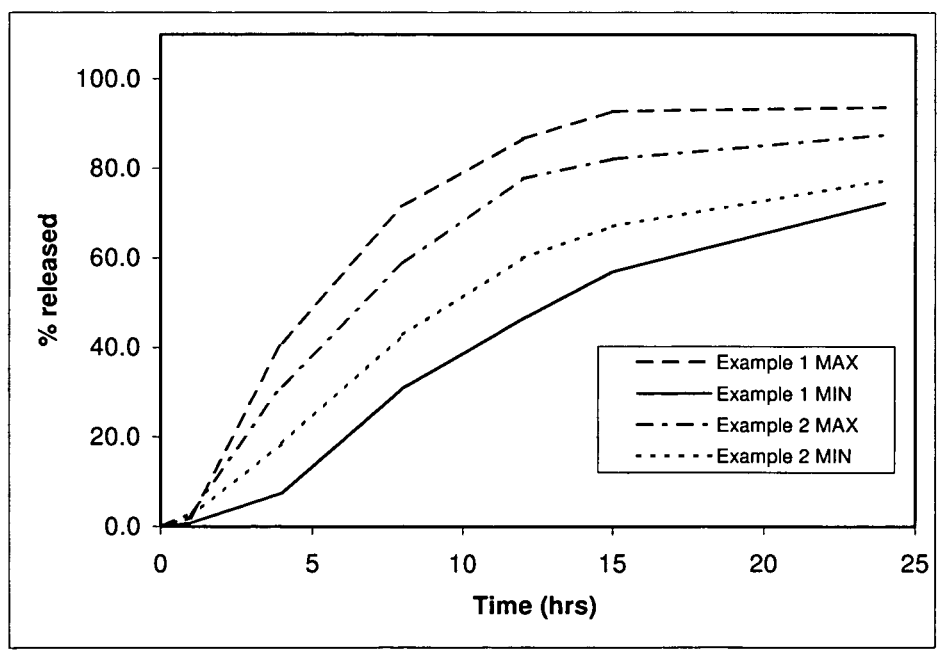
FIG. 5 depicts the expected maximum and minimum release profiles of alprazolam from the exemplary osmotic device according to Examples 1 and 2.

Examples 1 and 2 disclose two rupturing controlled release device formulations that only differ in the presence of the subcoat in Example 2. FIG. 5 depicts the expected maximum and minimum release profiles at each corresponding sampling time of alprazolam from the exemplary osmotic devices of Examples 1 and 2. The difference between the maximum and minimum release profile is due to the variability in drug release from the core exhibited by an osmotic device having a rupturing semipermeable membrane but not having a rupture-controlling subcoat, as in Example 1. The maximum and minimum release profiles can be thought of as approximations of the upper and lower boundaries within which the release profile of the exemplary osmotic device will vary on an overall or point to point basis. In other words, the area defined by the upper and lower boundaries is an approximation of the mean release profile plus or minus the standard deviation at the points of measurement. For the mean release profile for Example 1, the standard deviation can be ±0.05% to ±30% on a point-to-point or overall basis. For an osmotic device that ruptures, the variability in the drug release profile (from the core) is greater after rupture than before rupture of the device. Therefore, the variability will be greater on a point-to-point basis after rupture than before rupture.

FIG. 5 depicts the expected differences between the maximum and minimum release profiles at each corresponding sampling time of alprazolam from the exemplary osmotic device of Example 2. The expected release profiles (of Example 2) fall within the upper and lower boundaries defined for an osmotic device (of Example 1) without the subcoat. The upper and lower boundaries for the expected drug release profile of the osmotic device of Example 2 define the boundaries within which the mean release profile of the exemplary osmotic device may vary on an overall or point to point basis. For the mean release profile for Example 2, the standard deviation can be ±0.05% to ±15% on a point-to-point or overall basis.

Without being held bound to a particular mechanism, it is believed that the increased variability after rupture is due to the unpredictability of the extent of rupture and the rate of rupture of the membrane. The rupture-controlling subcoat, therefore, provides control of the extent and/or rate of rupture of the membrane. As a result, an osmotic device having a rupture-controlling subcoat provides a more reproducible, less variable drug release profile for drug released from the core.

The release profile of the osmotic device of the invention may vary from that shown in FIG. 5 according to the materials used to form the core and the semipermeable membrane covering the core, as well as the method used to form the passageway. For example, the release profile can be influenced by the various alternate embodiments of the preformed passageway such as the different sizes, shapes and functions depicted in FIG. 6. The release profile can also be influenced by the amount and properties of the active agent used to form the core, the amount of excipient used to form the core, the type of excipient used to form the core, and the amount or type of any other material used to form the core such as osmotically effective solutes, osmopolymers, or osmagents. The release profile can also be influenced by the material used to form the semipermeable membrane, covering the subcoat or by the material used to form any coating on the semipermeable membrane. The release profile can also be influenced by when the second passageway forms relative to initial exposure of the device as well as by the size of the second passageway once it forms. The device of the invention may also have a release profile that generally resembles a first order or pseudo first order release profile. In general, a rupturing osmotic device of the invention will have a smaller standard of deviation from the mean drug release profile that does an otherwise similar rupturing osmotic device not having a rupture-controlling subcoat.

Although the figures depict the rupturing controlled release device of the invention configured with particular shapes, it should be understood that the device can assume any shape or form currently known in the art of osmotic devices. That is, the device may assume any different shape and/or size according to which are optimal for the intended environment of use. In some embodiments, the delivery device will comprise one or more shoulders, ridges or edges covered by the membrane. In particular embodiments, the shape and size of the device will be optimal for use in subject mammals such as animals or human beings. The osmotic device can also include surface markings, cuttings, grooves, letters and/or numerals for the purposes of decoration, identification and/or other purposes.

The core of the rupturing controlled release device of the present invention comprises at least one active agent and can further comprise many other materials as discussed herein.

When the active agent is of limited solubility in the environment of use, osmotically effective solutes or osmotic agents, i.e. osmagents, that are capable of being totally or partially solubilized in the fluid, are added. These osmagents will aid in either the suspension or dissolution of the active agent in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art.

These osmagents can also be incorporated to the core of the osmotic device to control the release of an active agent therein. When the active agent is only partially or incompletely soluble in the fluid of an environment of use, it can be released as a suspension provided sufficient fluid has been imbibed or absorbed by the core to form a suspension.

One or more osmopolymers or swellable agents can also be added to the core of the device to aid in the delivery of the active agents. A "swellable agent" is any material that increases its volume upon exposure to a solution, such as a polymeric sorbent, for example, sodium polyacrylate, sodium polyacrylamide, poly-N-vinylpyrrolidone, poly-vinyltoluenesulfonate, poly-sulfoethyl acrylate, poly-2-hydroxyethyl acrylate, poly-vinylmethyloxazolidinone, hydrolyzed polyacrylamide, polyacrylic acid, copolymers of acrylamide and acrylic acid, and alkali metal salts of such of the polymers as contain sulfonate or carboxylate groups (see U.S. Pat. No. 3,926,891; U.S. Pat. No. 3,699,103, U.S. Pat. No. 5,693,411, all herein incorporated by reference in their entirety), or a naturally occurring water-swellable agent, such as mangrot seed, ground root of the buuk plant, cotton and sponge. Osmopolymers are well known to those of ordinary skill in the osmotic device art and well described in the patent and scientific literature. Exemplary osmopolymers include hydrophilic polymers that swell upon contact with water. Osmopolymers may be of plant or animal origin, or synthetic. Examples of osmopolymers include: poly(hydroxy-alkyl methacrylates) with molecular weight of 30,000 to 5,000,000, poly(vinylpyrrolidone) with molecular weight of 10,000 to 360,000, anionic and cationic hydrogels, polyelectrolyte complexes, poly(vinyl alcohol) having low acetate residual, optionally cross-linked with glyoxal, formaldehyde or glutaraldehyde and having a degree of polymerization of 200 to 30,000, a mixture of methyl cellulose, cross-linked agar and carboxymethylcellulose, a mixture of hydroxypropyl methylcellulose and sodium carboxymethylcellulose, sodium carboxymethylcellulose, hydroxypropyl methylcellulose, polyethylene oxide, polymers of N-vinyllactams, polyoxyethylene-polyoxypropylene gels, polyoxybutylene-polyethylene block copolymer gels, carob gum, polyacrylic gels, polyester gels, polyurea gels, polyether gels, polyamide gels, polypeptide gels, polyamino acid gels, polycellulosic gels, carbopol acidic carboxy polymers having molecular weights of 250,000 to 4,000,000, Cyanamer polyacrylamides, cross-linked indene-maleic anhydride polymers, Good-Rite™ polyacrylic acids having molecular weights of 80,000 to 200,000, Polyox™ polyethylene oxide polymers having molecular weights of 100,000 to 5,000,000, starch graft copolymers, and Aqua-Keeps™ acrylate polymer polysaccharides. These materials swell or expand to an equilibrium state when exposed to water or other biological fluids. This volume expansion is used to physically force the pharmaceutical agent out through openings that have been formed in the wall, shell or coating during manufacture. A water insoluble active agent is primarily released as insoluble particles, which therefore have limited bioavailability. Exemplary osmopolymers are disclosed in U.S. Pat. No. 5,422,123; No. 4,783,337; No. 4,765,989; No. 4,612,008; No. 4,327,725; No. 4,609,374; No. 4,036,228; No. 4,992,278; No. 4,160,020; 4,615,698. The osmopolymers generally swell or expand to a very high degree, usually exhibiting a 2 to 60 fold volume increase. The osmopolymers can be non-cross-linked or cross-linked. The swellable, hydrophilic polymers are, in some embodiments, lightly cross-linked, such as cross-links being formed by covalent or ionic bonds.

The subcoat comprises one or more water soluble and/or erodible materials. The subcoat will dissolve and/or erode when exposed to an aqueous environment of use for a sufficient period of time. Water soluble and/or erodible polymers are particularly useful materials. Materials which are suitable for making the subcoat composition include, by way of example and without limitation, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as hydroxymethylcellulose, hydroxyethylcellulose, and hydroxypropylcellulose; synthetic water-soluble cellulose-based lamina former such as alkyl cellulose (e.g. methyl cellulose) and its hydroxyalkyl methylcellulose cellulose derivatives such as a member selected from the group consisting of hydroxyethyl methylcellulose, hydroxypropyl methylcellulose, and hydroxybutyl methylcellulose; croscarmellose sodium; other cellulose polymers such as sodium carboxymethylcellulose; and other materials known to those of ordinary skill in the art. Other materials that can be used for this purpose include poly(vinylpyrrolidone), polyvinylalcohol, polyethylene oxide, a blend of gelatin and polyvinyl-pyrrolidone, gelatin, glucose, saccharides, povidone, copovidone, poly(vinylpyrrolidone)-poly(vinyl acetate) copolymer. This layer can comprise other pharmaceutical excipients that do or do not alter the way in which it behaves in the environment of use. The subcoat can comprise combinations of materials.

Other suitable materials include hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA:MMA:MA synthesized in the presence of N,N'-bis(methacryloyloxyethyloxycarbonylamino)-azobenzene, azopolymers, and calcium pectinate.

The subcoat can also comprise povidone, which is supplied by BASF under its trademark Kollidon™ K 30, and hydroxypropyl methylcellulose, which is supplied by Dow under its trademark Methocel™ E-15. The materials can be prepared in solutions having different concentrations of polymer according to the desired solution viscosity. For example, a 10% w/v aqueous solution of Kollidon™ K 30 has a viscosity of about 5.5-8.5 cps at 20° C., and a 2% w/v aqueous solution of Methocel™ E-15 has a viscosity of about 13-18 cps at 20° C.

An effervescent couple or gas-forming precursor can be included in the subcoat. An effervescent couple forms a gas when placed in an environment of use and includes an acidifying agent and a gas-forming precursor. For example, an effervescent couple includes a solid organic acid and a solid bicarbonate or carbonate salt. When place in contact with an aqueous environment (it need not be acidic), the individual components of the effervescent couple dissolve and react to form carbon dioxide.

As used herein, a "gas-forming precursor" is a compound or group of compounds that form a gas, such as nitrogen, carbon dioxide, chlorine dioxide or oxygen, when placed in an environment of use. For example, a bicarbonate or carbonate salt is considered a gas-forming precursor, since it forms carbon dioxide when placed in an acidic environment such as the gastric fluids of the stomach. Exemplary gas-forming precursors release a gas, or cause a solution to effervesce, when exposed to a proton source such as an acidic agent or water. The alkaline agent can be a carbon dioxide precursor, an oxygen precursor or a chlorine dioxide precursor. The preferred gas-forming precursor is a carbon dioxide precursor, compounds such as carbonate, sesquicarbonate and hydrogencarbonate salts (in this specification, carbonate and hydrogencarbonate, or bicarbonate, are generically referred to as carbonate) of potassium, sodium, calcium, ammonium, or L-lysine carbonate, arginine carbonate, sodium glycine carbonate, sodium amino acid carbonate. Acidic components suitable for incorporation into the dosage form include, for example, monosodium dihydrogen phosphate, tartaric acid, citric acid, fumaric acid, maleic acid, or other weak organic acids.

Many common materials known by those of ordinary skill in the art are suitable for use as the semipermeable membrane. Exemplary materials include cellulose esters, cellulose ethers, cellulose esters-ethers and combinations thereof. However, it has been found that a semipermeable membrane consisting essentially of cellulose acetate (CA) and poly(ethylene glycol) (PEG), in particular PEG 400, is preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50-99% by weight of CA: about 50-1% by weight of PEG, and generally about 95% by weight of CA:about 5% by weight of PEG. The ratio can be varied to alter permeability and ultimately the release profile of the osmotic device.

Representative materials for making the semipermeable membrane include a member selected from the group consisting of cellulose acylate, cellulose diacylate, cellulose triacylate, cellulose acetate, cellulose diacetate, cellulose triacetate, mono, di and tricellulose alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose diacetate having a D.S. of 1 to 2 and an acetyl content of 21 to 35%; cellulose triacetate having a degree of substitution (D.S.) of 2 to 3 and an acetyl content of 35 to 44.8%; and the like. More specific cellulosic polymers include cellulose propionate having a D.S. of 1.8 and a propionyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentalate, and the like. Additional semipermeable polymers include acetaldehyde dimethyl acetate, cellulose acetate ethyl carbamate, cellulose acetate phthalate for use in environments having a low ph, cellulose acetate methyl carbamate, cellulose acetate dimethyl aminoacetate, semipermeable polyamides, semipermeable polyurethanes, semipermeable sulfonated polystyrenes, cross-linked selectively semipermeable polymers formed by the coprecipitation of a polyanion and a polycation as disclosed in U.S. Pat. No. 3,173,876, No. 3,276,586, No. 3,541,005, No. 3,541,006, and No. 3,546,142; semipermeable polymers as disclosed by Loeb and Sourirajan in U.S. Pat. No. 3,133,132; lightly cross-linked polystyrene derivatives; cross-linked poly(sodium styrene sulfonate), cross-linked poly(vinylbenzyltrimethyl ammonium chloride). These and others polymers are disclosed in U.S. Pat. No. 3,845,770, No. 3,916,899, No. 4,765,989 and No. 4,160,020; and in Handbook of Common Polymers (Scott, J. R. and Roff, W. J., eds.; 1971; CRC Press, Cleveland, Ohio).

The cellulose esters differ in their cellulose chain length and the type and amount of ester groups attached to the chain. For cellulose acetates, as the amount of acetyl content increases, the permeability decreases. The cellulose acetate grade 1 comprises 7-10% by weight of hydroxyl groups and has a viscosity of 200-280 seconds as determined by ASTM Method D 1343. The cellulose acetate grade 2 comprises 3-5% by weight of hydroxyl groups and has a viscosity of 6 to 45 seconds. The cellulose acetate grade 3 comprises 3-5% by weight of hydroxyl groups and has a viscosity of 100 to 240 seconds.

Some exemplary grades of cellulose acetate that are suitable for use in the making the semipermeable membrane are also described in the table below, which is included by way of example. Cellulose acetate of differing grades is readily available from Eastman Chemical Company (Kingsport, Tenn., USA).

| Cellulose Acetate | Hydroxyl Content (% by wt.) | Acetyl Content (% by wt.) | Viscosity* (seconds) |
|---|---|---|---|
| Grade 1 | 7-10 | 30-36 | 200-280 |
| Grade 2 | 3-5 | 37-43 | 6-45 |
| Grade 3 | 3-5 | 37-43 | 100-240 |

*Viscosity determined as set forth in ASTM D817 (Formula A) and D1343, the disclosure of which is hereby incorporated by reference.

The semipermeable membrane can also comprise flux enhancing agents. The flux enhancing agent increase the volume of fluid imbibed into the core. The flux enhancing agents are water-soluble components such as sodium chloride, potassium chloride, sugar, sucrose, sorbitol, mannitol, polyethylene glycol (weight av. molecular weight 380-3700), propylene glycol, hydroxypropyl cellulose, hydroxypropyl methylcellulose and mixtures thereof. In other embodiments, the wall also provides the release of drug from the core through pores. The porosity of the semipermeable membrane will vary according to its composition. Preferred copolymers used in the manufacturing of the wall include: poly(ammonium methacrylate) copolymer RL (Eudragit™ RL), poly(ammonium methacrylate) copolymer (type A-USP/NF), poly(aminoalkyl methacrylate) copolymer RL-JSP I), and (ethyl acrylate)-(methyl methacrylate)-[(trimethylammonium)-ethylmethacrylate] (1:2:0.2) copolymer, MW 150,000. More preferred polymers include (Röhm Pharma, Weiterstadt): Eudragit™ RS 100: solid polymer, Eudragit™ RL 12.5:12.5% solution in solvent, Eudragit™ RL 30 D: 30% aqueous dispersion, and other equivalent products.

The following poly (ammonium methacrylate) copolymers can also be used: ammonium methacrylate copolymer RS (Eudragit™ RS), poly(ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150,000. Specific polymers include (Röhm Pharma, Weiterstadt): Eudragit™ RS 100: solid polymer, Eudragit™ RS 12.5:12.5% solution in solvent, Eudragit™ RS 30 D: 30% aqueous dispersion and other equivalent products.

Alternative embodiments of the invention include pore former(s) or porosigens in the semipermeable membrane to form pores over time to provide diffusion of the active agent through the semipermeable membrane. Acceptable pore formers include polysaccharides such as mannitol, galactose, mannose, aldohexose, altrose, talose and sorbitol; alkali metal salts such as sodium chloride, lithium carbonate, potassium chloride, and potassium sulfate; alkaline earth metal salts such as calcium phosphate, and calcium nitrate; and transition metal salts such as zinc sulfate, ferric chloride, and ferrous sulfate.

In alternate embodiments, plasticizers can be included in the present device to create pores over time to provide diffusion of the active agent through the semipermeable membrane and/or to modify the properties and characteristics of the polymers used in the coats or core of the device. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, NY) the disclosure of which is hereby incorporated by reference.

As used herein, the term "brittling agent" refers to a compound or composition that renders the semipermeable membrane more susceptible to rupture during use thereby facilitating increasing the size of the preformed passageway. The brittling agent can be placed at one or more specific locations within or placed throughout the membrane to form one or more weakened sections.

The polymer coat (11) (see FIG. 3), that covers the semipermeable membrane (10) and blocks the passageway (13), is made of synthetic, semisynthetic or natural material which, through selective dissolution and/or erosion shall allow the passageway to be unblocked thus allowing the process of osmotic delivery to start. This slow or fast dissolving polymer coat (11) can be impermeable to a first external fluid, while being soluble in a second external fluid. This property can help to achieve a controlled and selective release of the active compound in the core.

The polymer coat (11) will generally comprise an inert and non-toxic material which is at least partially, and generally substantially completely, soluble and/or erodible in an environment of use. The polymer coat (11) can be soluble in one or more environments of use. For example, the polymer coat (11) can be soluble in the same environment of use in which the external coat (14) is soluble in, or it can be soluble in the same environment of use in which the core (8) is soluble. Although the art discloses microporous layers comprising materials which can be included in the polymer coat (11), the presence of poly(vinylpyrrolidone)-(vinyl acetate) copolymer in the polymer coat (11) has been found to provide advantageous properties and characteristics to the polymer coat. Thus, the polymer coat (11) will, in some embodiments, comprise poly(vinylpyrrolidone)-(vinyl acetate) copolymer, and it can also include other water soluble materials useful for this type of coat. Exemplary materials are disclosed in U.S. Pat. Nos. 4,576,604 and 4,673,405, and the text Pharmaceutical Dosage Forms: Tablets Volume I, Second Edition. A. Lieberman. ed. 1989, Marcel Dekker, Inc. the relevant disclosures of which are hereby incorporated by reference.

In specific embodiments, the polymer coat (11) will be insoluble in the fluid of a first environment of use, such as gastric juices, acidic fluids, or polar liquids, and soluble or erodible in the fluid of a second environment of use, such as intestinal juices, substantially pH neutral or basic fluids, or apolar liquids. A wide variety of other polymeric materials are known to possess these various solubility properties and can be included in the polymer coat (11). Such other polymeric materials include, by way of example and without limitation, cellulose acetate phthalate (CAP), cellulose acetate trimelletate (CAT), poly(vinyl acetate) phthalate (PVAP), hydroxypropyl methylcellulose phthalate (HP-MCP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit™ L-30-D (MA-EA, 1:1), Eudragit™ L-100-55 (MA-EA, 1:1), hydroxypropyl methylcellulose acetate succinate (HPMCAS), Coateric™ (PVAP), Aquateric™ (CAP), AQUACOAT™ (HPMCAS) and combinations thereof. The polymer coat (11) can also comprise dissolution aids, stability modifiers, and bioabsorption enhancers.

When the polymer coat (11) is intended to be dissolved, eroded or become detached from the core in the colon, materials such as hydroxypropylcellulose, microcrystalline cellulose (MCC, Avicel™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be included in the polymer coat (11).

One polymeric material for use in the polymer coat (11) involves enteric materials that resist the action of gastric fluid avoiding permeation through the semipermeable wall while one or more of the materials in the core (8) are solubilized in the intestinal tract thereby allowing delivery of a drug from the core (8) by osmotic pumping to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The polymer coat (11) can also comprise povidone, which is supplied by BASF under its Kollidon K 30 trademark, and hydroxypropyl methylcellulose, which is supplied by Dow under its Methocel E-15 trademark. The materials can be prepared in solutions having different concentrations of polymer according to the desired solution viscosity. For example, a 10% w/v aqueous solution of Kollidon K 30 has a viscosity of about 5.5-8.5 cps at 20° C., and a 2% w/v aqueous solution of Methocel E-15 has a viscosity of about 13-18 cps at 20° C.

The polymer coat can also comprise other materials suitable which are substantially resistant to gastric juices and which will promote either enteric or colonic release. For this purpose, the polymer coat can comprise one or more materials that do not dissolve, disintegrate, or change their structural integrity in the stomach and during the period of time that the osmotic device resides in the stomach. Representative materials that keep their integrity in the stomach can comprise (a) a member selected from the group consisting of keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abietate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkylacrylic acid and alkylacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 molecular weight, methacrylic acid-dimethylaminoethyl-methacrylate-ethylacrylate of 750,000 molecular weight, methacrylic acid-methylmethacrylate-ethylacrylate of 1,000,000 molecular weight, and ethylacrylate-methylmethacrylate-ethylacrylate of 550,000 molecular weight; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The external coat is comprised of one or more coatings, which are generally independently selected at each occurrence from the group consisting of: a drug-containing coating, a release rate modifying coating, a porous coating; a soluble coating, an insoluble coating, a semipermeable membrane; and a delayed release coating. A delayed release coating can be a timed-release coating, enteric coating, colonic delivery coating, gastric fluid resistant coating or other such coating used in the pharmaceutical sciences for delaying the release of a compound from a dosage form for a period time after exposure to an environment of use.

In alternate embodiments, the external coat may contain a second active agent that may or may not be the same as a first active agent in the core. Depending on the composition of the external coat, the second active agent is available for immediate, slow, delayed, sustained, pseudo-first order, pseudo-zero order, timed, controlled release or combinations thereof. The second active agent can be applied to the surface of the device according to common methods of preparing similar osmotic devices such as applying to its surface solids in solution or suspension through the use of a sprayer that spreads them uniformly over the core or by employing nucleated compression or other suitable methods known to those of ordinary skill in the art. The external coat can comprise poly (vinylpyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The active agent-containing external coat can also comprise dissolution aids, stability modifiers, and bioabsorption enhancers.

When the external coat comprises a combination of materials, the relative amounts and ratios of those materials can be varied as desired. For example, when the external coat comprises PVP and PEG, the ratio of PVP:PEG can vary as needed, e.g., from about 3-60% by weight of PVP: about 0.1-30% by weight of PEG based upon the weight of the external coat.

The external coat can also comprise a second active agent generally present in an amount ranging from about 0.1 to 99% by weight of the coat. This wide range provides great latitude in the design and application of the osmotic device. Those of ordinary skill in the art will appreciate that the particular amount of second active agent employed will vary according to, among other things, the identity and physical properties and characteristics of the second active agent, the intended application of the osmotic device, the desired effect the second active agent is intended to have, and the physiological condition, if any, being treated.

As used herein, the term "preformed passageway" refers to a passageway or passageway precursor that has been formed on the semipermeable membrane of the device by mechanical means, such as by a laser, drill and/or etching apparatus. A preformed passageway is optionally plugged after initial formation, such as depicted in FIG. 3. If a water soluble plug is used, the preformed passageway will increase in size even after all of the plug has been removed from the preformed passageway. The term "preformed passageway" is not intended to cover pores, holes, apertures, channels or other similar structures formed in the semipermeable membrane by incorporation of pore formers, water soluble particulates, or similar materials known to those of ordinary skill, into the semipermeable membrane of the rupturing controlled release device during manufacture of the osmotic device.

The osmotic device of the invention comprises at least one preformed passageway (pore, hole, or aperture) that communicates the exterior of the semipermeable membrane with the core of the device. The preformed passageway can be formed according to any of the known methods of forming passageways in a semipermeable membrane. Such methods include, for example, 1) drilling a hole through the semipermeable membrane with a bit or laser; 2) punching a hole through the semipermeable membrane; or 3) employing a tablet punch having a pin to punch a hole through the semipermeable membrane. The passageway can pass through the semipermeable membrane and one or more of any other coating onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming preformed passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., U.S. Pat. No. 3,845,770 to Theeuwes et al., PCT International Publication No. WO 04/103349 to Faour, and U.S. Pat. No. 6,809,288 to Faour, the disclosures of which are hereby incorporated by reference.

A preformed passageway can be made to substantially retain its size during use of the device or it can be made to increase in size during use of the dosage form. Preformed passageways of different sizes, shapes and functions can be used.

In some embodiments, the membrane defining the edge of the preformed passageway in the wall may tear (rupture) in a predetermined or random manner, and the shape of the preformed passageway after enlargement can be made to approximate a predetermined or randomly determined shape. The extent to which a passageway increases in size can also be related to the viscosity, molecular weight or degree of substitution of the at least one excipient. Generally, increasing the viscosity, molecular weight, or degree of substitution of the at least one excipient will increase the extent to which the passageway increases in size.

A device according to the present invention can comprise one or more preformed passageways including two, three, four, five, six, seven, eight, nine, ten or more preformed passageways. It is only necessary that the preformed passageways together are adapted to permit controlled release of ingredients from the core during use. In some embodiments, the semipermeable membrane comprises at least one preformed passageway having a diameter ranging from 0.2 mm to 0.8 mm. In other embodiments, the total area of the preformed passageway(s) present in the membrane ranges from 0.12 mm$^2$ to 2.1 mm$^2$.

Figure 6:
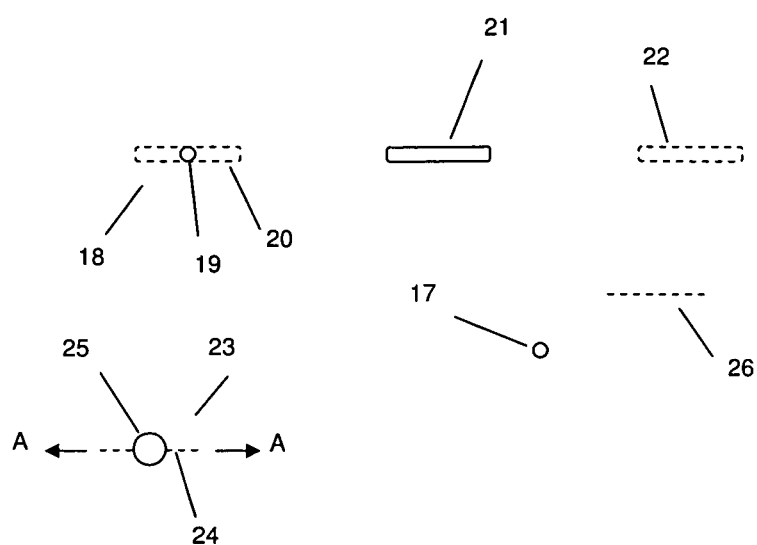
FIG. 6 depicts various alternate embodiments for a preformed aperture according to the invention.

According to some embodiments, at least one rupturing controlled release device is moved along a predetermined path in a laser apparatus at a predetermined linear velocity that is greater than the velocity used to make similar osmotic devices that do not have passageways that increase in size during use. The device is tracked at the predetermined velocity with a laser having a wavelength that is absorbable by the coating. During the tracking, a laser beam, which comprises sequential individual pulses, is then fired at a predetermined section of the coated core for a predetermined period of time and with a predetermined pulse period. The pulse period is the period of time measured from the beginning of a first individual pulse to the beginning of the next individual pulse of the laser beam. The laser beam is also adjusted to fire with a predetermined pulse width, which is the amount of time from the beginning of an individual pulse to the end of that same individual pulse. By controlling the three pulse parameters and the liner velocity, passageways as depicted in FIG. 6 can be prepared.

A preformed passageway can be made to substantially retain its size during use of the device or it can be made to increase in size during use of the dosage form. Preformed passageways of different sizes, shapes and functions, such as those depicted in FIG. 6 can be formed. The passageway (18) includes a central circular hole (19) that penetrates the semipermeable membrane, and two laterally extending portions (20), which are scored or etched regions, that do not penetrate the semipermeable membrane. When this passageway is used, the semipermeable membrane tears along the etched regions to form the enlarged preformed passageway. The laterally extending regions can be any length desired. The passageway (21) is oval- or slot-shaped, and it penetrates the semipermeable membrane. When it is used, the preformed passageway will generally tend to tear at the ends of the slot. The passageway (22) is scored on the surface of the semipermeable membrane. The scored region ruptures during use to form the actual passageway through which active agent is released. This preformed passageway can continue to tear along the direction of the score or it can tear in random directions. The passageway (23) is similar to the passageway (18) except that these scored regions (24 and 25) have a much narrower width and depth than the other scored regions (20). The passageway (26) is actually a scored region on the semipermeable membrane that ruptures during use of the osmotic device. The passageways (17, 18, 21, 22, 23, and 26) are generally formed with a laser. The passageways (18, 21, 22, 23, and 26) will generally increase in size in a predetermined manner during use, i.e., generally in a direction extending along the lateral axes of the passageways. The preformed passageway does not require etchings or scored regions at its edge in order to increase in size during use.

Figure 7:
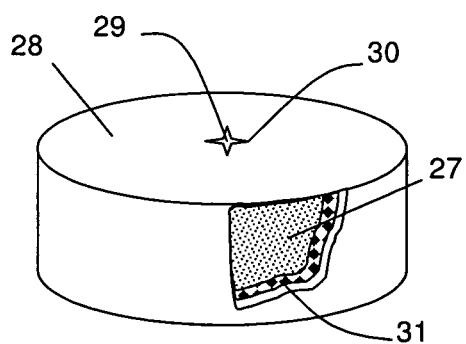
FIG. 7 depicts a partial sectional perspective view of the general stage III of operation of a rupturing controlled release device comprising at least one preformed passageway that ruptures in a membrane edge.

FIG. 7 discloses a rupturing controlled release device comprising: a) a core (27) comprising at least one active agent and at least one excipient, b) a semipermeable membrane (28) comprising at least one preformed passageway (29) that ruptures in a membrane edge (30) due to the increase of the internal pressure of the device (the preformed passageway is larger after use than it is prior to use of the device), c) an optional scored region of the membrane adjacent the passageway, and d) a release-controlling subcoat (31) between the core and the semipermeable membrane (28).

In some embodiments, the subcoat of the rupturing controlled release device contains at least one active agent. Example 3 discloses a rupturing controlled release device formulation containing sildenafil in the core, levodopa in the subcoat, and carbidopa in an immediate or rapid release external coat.

The expected release profiles of the sildenafil, levodopa and carbidopa from the osmotic device formulation of Example 3 are disclosed in the example.

Sildenafil is commercially available under the trademark Viagra™. Sildenafil is an orally active, potent, and selective inhibitor of CGMP-specific phosphodiesterase type 5 (PDE5). Sildenafil thus enhances the relaxant effect of nitric oxide (NO) released in response to sexual stimulation by increasing cGMP concentrations in smooth muscle in the corpus cavernosum, preventing it hydrolysis, allowing blood to flow into the penis, thereby producing an erection and prolonging the vasodilatation effect. Levodopa (3,4-dihydroxyphenylalanine) is the metabolic precursor of dopamine after decarboxylation within the presynaptic terminals of dopaminergic neurons, and it actions in the brain are mediated by a family of dopamine receptor proteins. Levodopa is almost always administered in combination with a peripherally acting inhibitor of aromatic L-amino acid decarboxylase, such as carbidopa, in order to improve absorption. Viagra™ tablets at recommended doses has no effect in the absence of sexual stimulation. Both et al. disclose the effect of levodopa on sexual response in men by the administration of 100 mg (Neuropsychopharmacology (2005) 30, 173-183). While brain and spinal cord dopaminergic receptor activation are believed to participate in regulation of male sexual desire, mediating sexual behavior and erection which are triggered by levodopa administration, the co-administration of levodopa and sildenafil as an erectogenic agent, would support the arousal in patients with erectile dysfunction, potentiating the libido with the physical flair.

Examples 4, 5, and 6 disclose controlled release device formulations containing nifedipine, carvedilol and carbamazepine respectively. Each example discloses four controlled release device formulations comprising 0, 5, 10 and 15 mg of subcoat.

Figure 9:
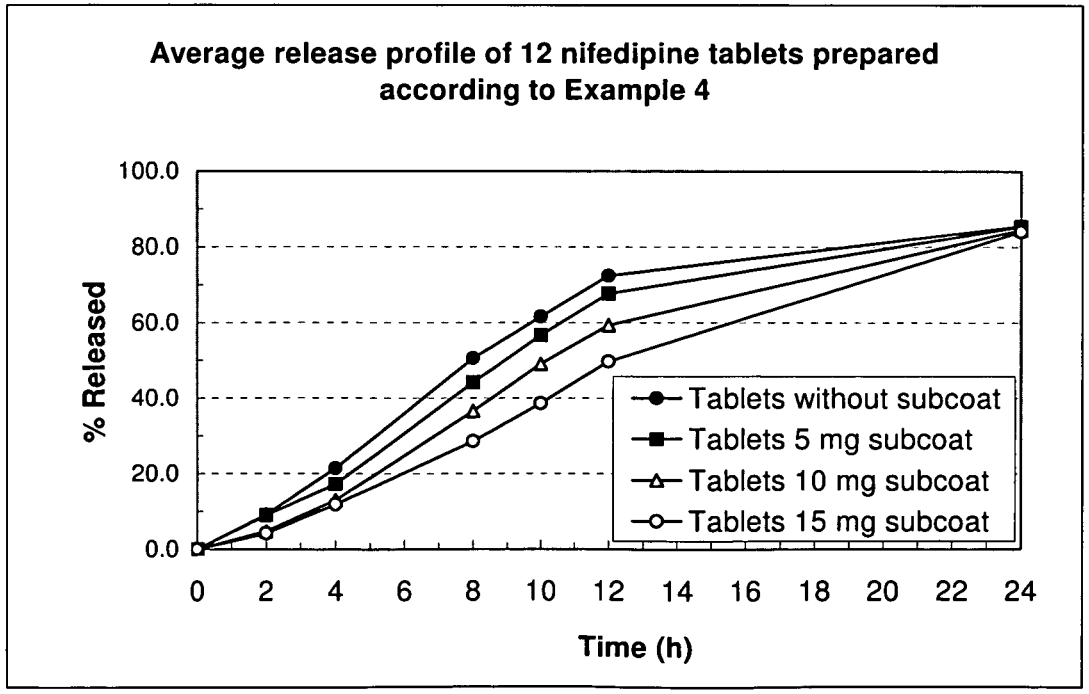
FIG. 9 depicts the average release profiles of 12 nifedipine tablets prepared according to Example 4.
Figure 10:
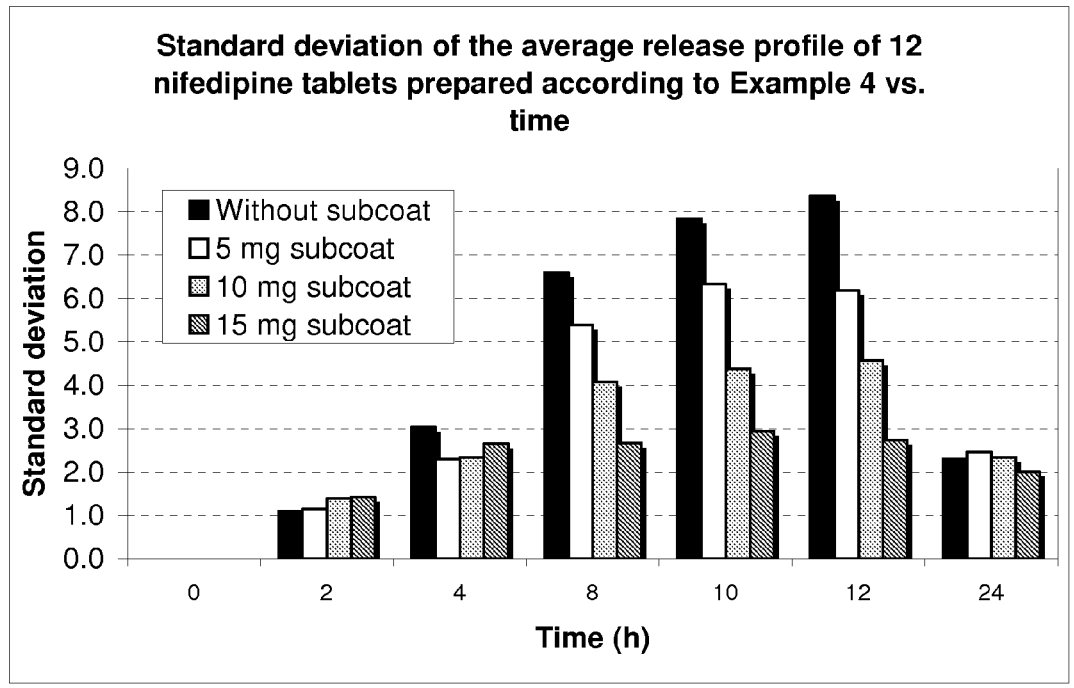
FIG. 10 depicts the standard deviation of the average release profiles of 12 nifedipine tablets prepared according to Example 4 versus time.
Figure 11:
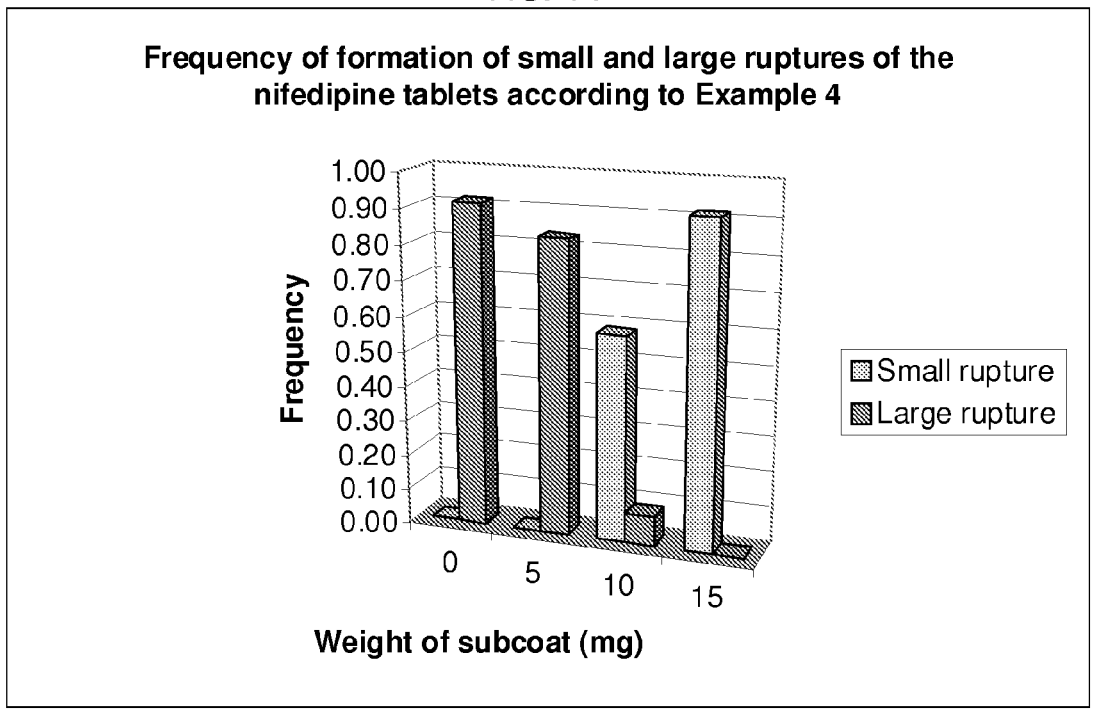
FIG. 11 depicts the frequency of formation of small and large ruptures in the membrane of the nifedipine tablets prepared according to Example 4.

Example 4 discloses four different rupturing controlled release device formulations containing nifedipine in the core. The formulations only differ in the amount or weight of the subcoat. The drug release data and aperture formation data are summarized in the example. FIG. 9 depicts the average release profiles of nifedipine tablets prepared according to Example 4. The average release profiles are disclosed in Tables A (tablets without subcoat), B (tablets comprising 5 mg subcoat), C (tablets comprising 10 mg subcoat) and D (tablets comprising 15 mg subcoat). Both the extent and the rate of release of nifedipine over the time depend on the amount or weight of subcoat. A lower amount or weight of subcoat results in a slower release profile and slower rates of release, whereas the overall or final amount of nifedipine released is the same for different amounts or weights of subcoat. FIG. 10 depicts the standard deviation of the average release profiles of 12 nifedipine tablets prepared according to Example 4 vs. time. The standard deviation of the release profiles at 8, 10 and 12 hours corresponding to the dosage forms comprising 0, 5, 10 and 15 mg of subcoat indicates the increased reproducibility (lower SD) in the release profiles. FIG. 11 depicts the frequency of formation of small and large ruptures obtained for twelve tablets (#1-#12) of nifedipine formulations with different weight of subcoat when the tablets were exposed to an aqueous environment of use (such as an aqueous assay solution). The results show that the frequency of formation for large ruptures (those about 3.00 mm or larger) decreases as the amount or weight of subcoat increases, and the frequency of formation for small ruptures (those about 1.49 mm or smaller) increases as the amount or weight of subcoat increases.

Nifedipine is commercially available under the trademark Procardia™ XL. Nifedipine is a drug belonging to a class of pharmacological agents known as the calcium channel blockers. Its chemical name is 3,5-pyridinedicarboxylic acid, 1,4-dihydro-2,6-dimethyl-4-(2-nitrophenyl)-, dimethyl ester. Procardia™ XL is indicated for the management of vasospastic angina, chronic stable angina (effort-associated angina) and for the treatment of hypertension.

Figure 12:
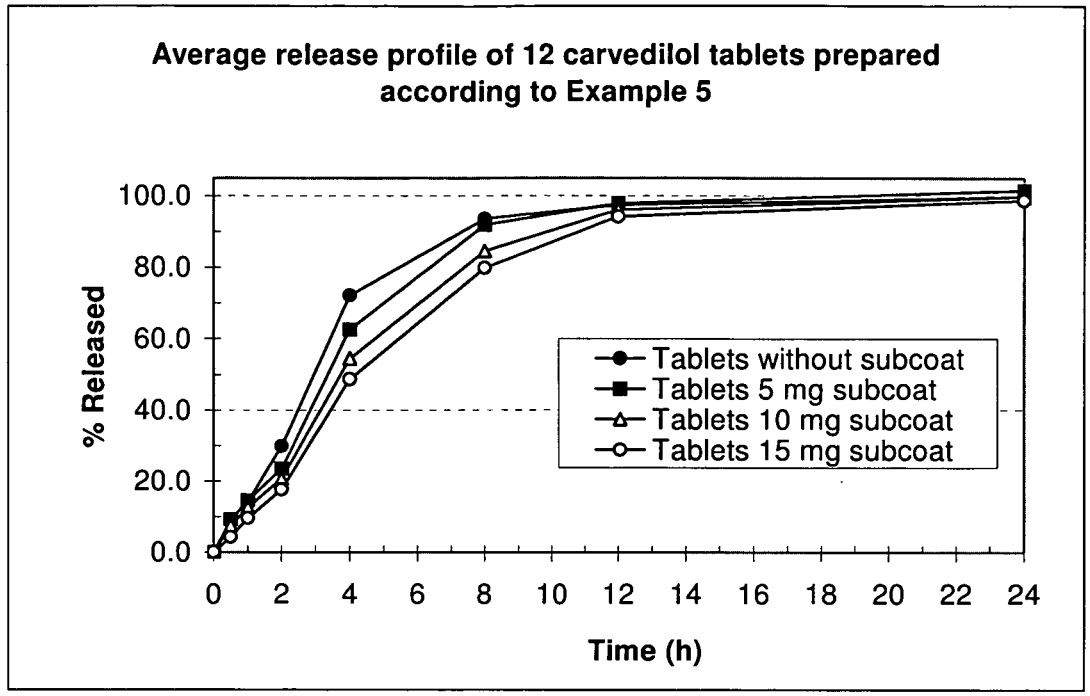
FIG. 12 depicts the average release profiles of 12 carvedilol tablets prepared according to Example 5.
Figure 13:
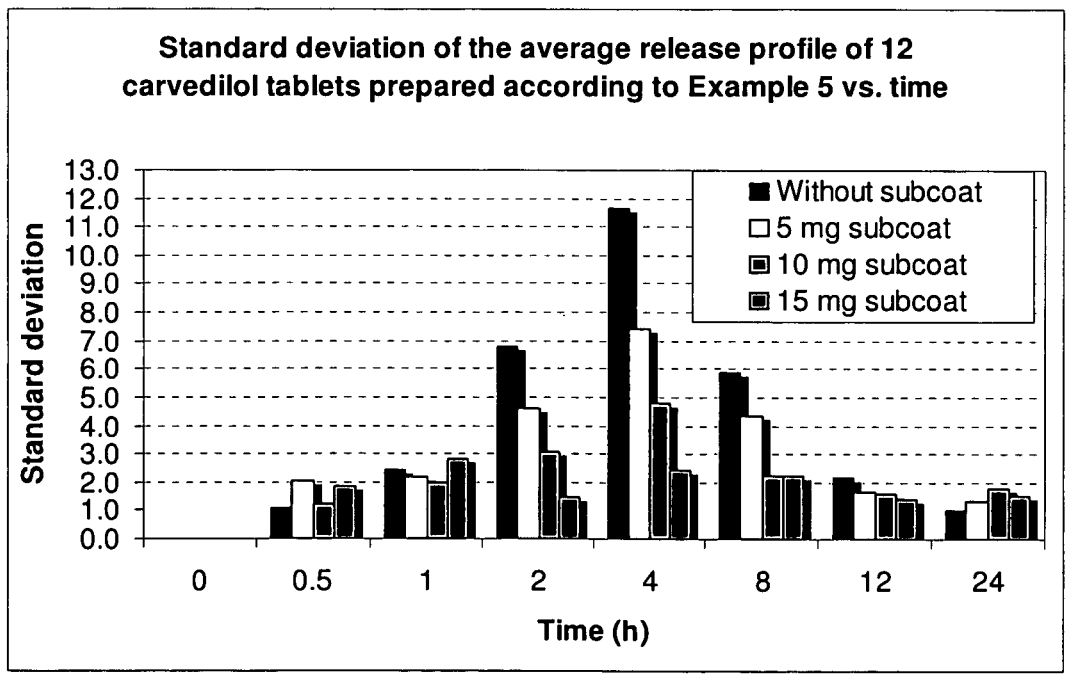
FIG. 13 depicts the standard deviation of the average release profiles of 12 carvedilol tablets prepared according to Example 5 versus time.
Figure 14:
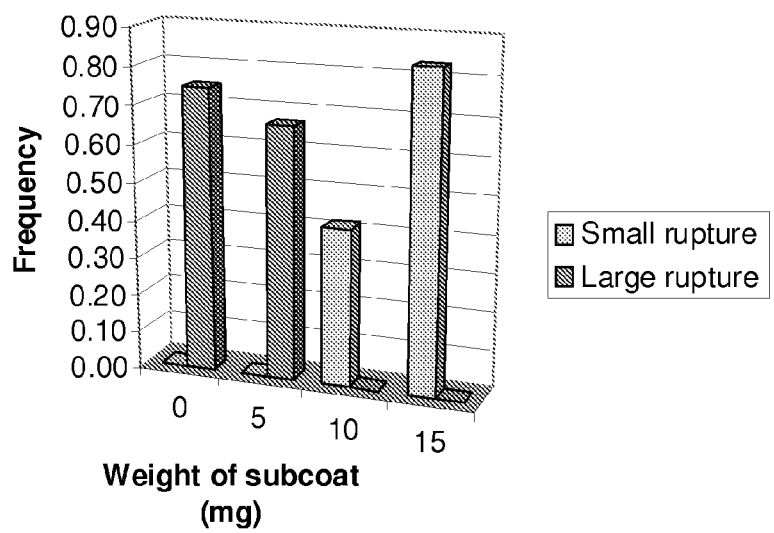
FIG. 14 depicts the frequency of formation of small and large ruptures in the membrane of the carvedilol tablets prepared according to Example 5.

Example 5 discloses four rupturing controlled release device formulations containing carvedilol in the core. The formulations only differ in the amount or weight of the subcoat. The drug release data and aperture formation data are summarized in the example. FIG. 12 depicts the average release profiles of carvedilol tablets prepared according to Example 5. The average release profiles are disclosed in tables E (tablets without subcoat), F (tablets comprising 5 mg subcoat), G (tablets comprising 10 mg subcoat) and H (tablets comprising 15 mg subcoat). Both the extent and the rate of release of carvedilol over the time depend on the amount or weight of subcoat. A lower amount or weight of subcoat results in a slower release profile and slower rates of release, whereas the overall or final amount of carvedilol released is the same for different amounts or weights of subcoat. FIG. 13 depicts the standard deviation of the average release profiles of 12 carvedilol tablets prepared according to Example 5 vs. time. The standard deviation of the release profiles at 2, 4 and 8 hours corresponding to the dosage forms comprising 0, 5, 10 and 15 mg of subcoat indicates the increased reproducibility (lower SD) in the release profiles. FIG. 14 depicts the frequency of formation of small and large ruptures obtained for twelve tablets (#1-#12) of carvedilol formulations with different weights of subcoat. The results show that the frequency of formation of large ruptures (those about 3.00 mm or larger) decreases as the amount or weight of subcoat increases, and the frequency of formation of small ruptures (those about 1.49 mm or smaller) increases as the amount or weight of subcoat increases.

Carvedilol phosphate (extended-release capsules) is commercially available under the trademark Coreg™ CR. Carvedilol phosphate is a nonselective β-adrenergic blocking agent with α1-blocking activity. Its chemical name is (2RS)-1-(9H-Carbazol-4-yloxy)-3-[[2-(2-methoxyphenoxy)ethyl]amino]propan-2-ol phosphate salt (1:1) hemihydrate. COREG™ CR is indicated for the treatment of mild-to-severe heart failure, left ventricular dysfunction following myocardial infarction, and essential hypertension. Carvedilol can be administered alone or in combination with other drugs such as digoxin for the management of atrial fibrillation in patients with heart failure.

Figure 15:
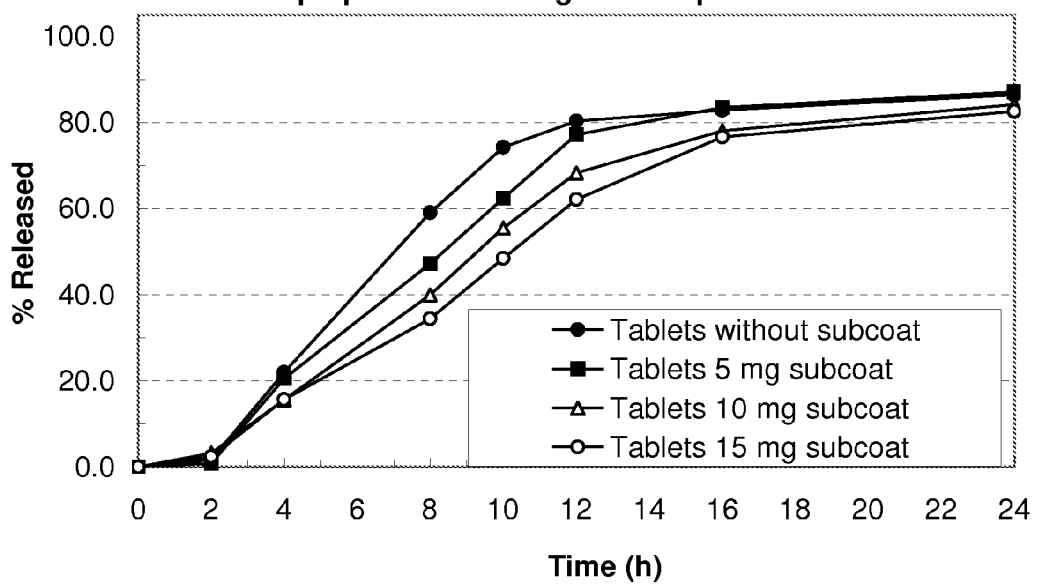
FIG. 15 depicts the average release profiles of 12 carbamazepine tablets prepared according to Example 6.
Figure 16:
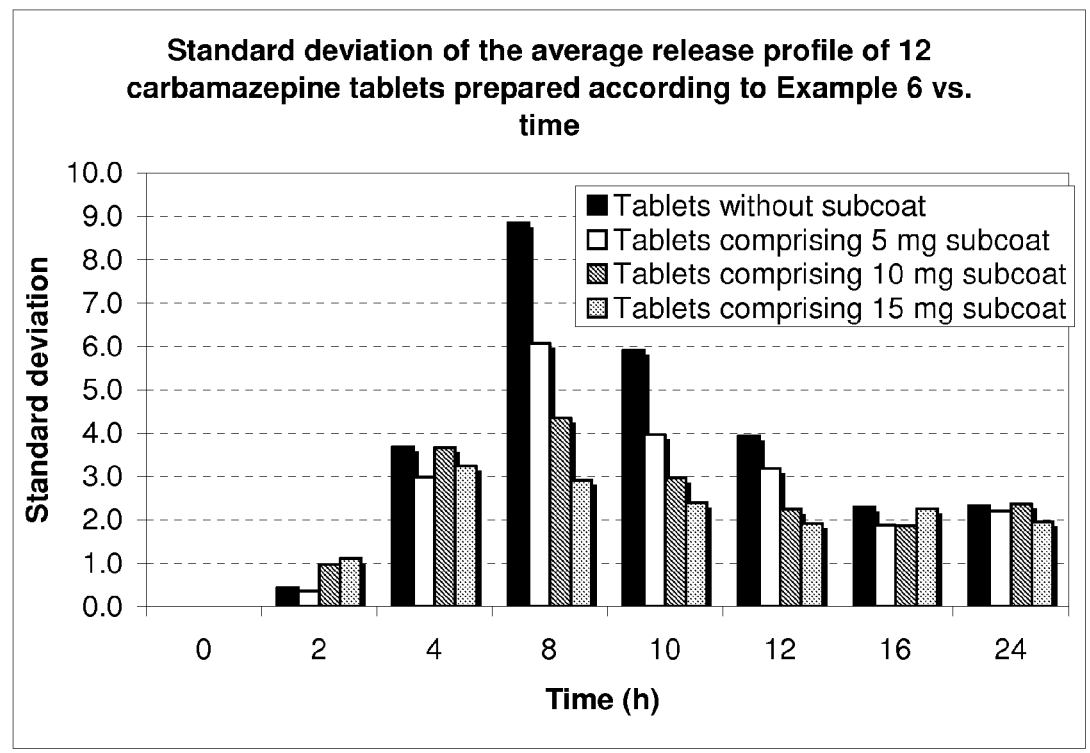
FIG. 16 depicts the standard deviation of the average release profiles of 12 carbamazepine tablets prepared according to Example 6 versus time.
Figure 17:
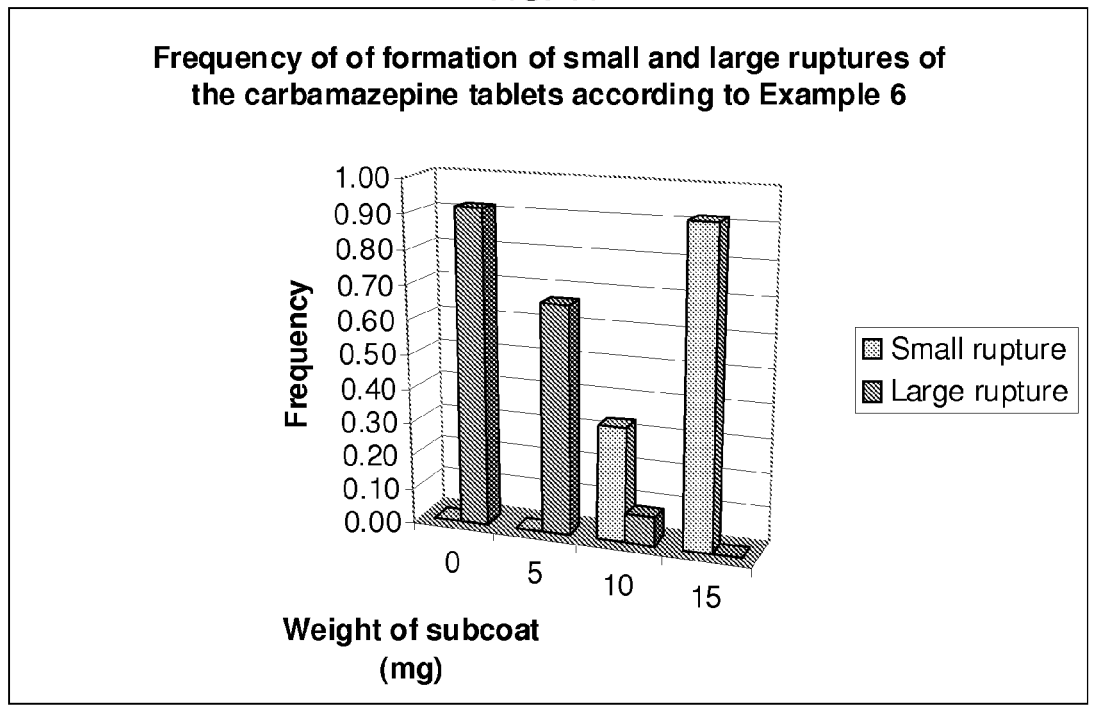
FIG. 17 depicts the frequency of formation of small and large ruptures in the membrane of the carbamazepine tablets prepared according to Example 6.

Example 6 discloses four rupturing controlled release device formulations containing carbamazepine in the core. The formulations only differ in the amount or weight of the subcoat. The drug release data and aperture formation data are summarized in the example. FIG. 15 depicts the average release profiles of carbamazepine tablets prepared according to Example 6. The average release profiles are disclosed in tables I (tablets without subcoat), J (tablets comprising 5 mg subcoat), K (tablets comprising 10 mg subcoat) and L (tablets comprising 15 mg subcoat). Both the extent and the rate of release of carbamazepine over the time depend on the amount or weight of subcoat. A lower amount or weight of subcoat results in a slower release profile and slower rates of release, whereas the overall or final amount of carbamazepine released is the same for different amounts or weights of subcoat. FIG. 16 depicts the standard deviation of the average release profiles of 12 carbamazepine tablets prepared according to Example 6 vs. time. The standard deviation of the release profiles at 8, 10 and 12 hours corresponding to the dosage forms comprising 0, 5, 10 and 15 mg of subcoat indicates the increased reproducibility (lower SD) in the release profiles. FIG. 17 depicts the frequency of small and large ruptures obtained for twelve tablets (#1-#12) of the carbamazepine formulation with different weights of subcoat. The results show that the frequency of formation of large ruptures (those about 3.00 mm or larger) decreases as the amount or weight of subcoat increases, and the frequency of formation of small ruptures (those about 1.49 mm or smaller) increases as the amount or weight of subcoat increases.

Carbamazepine (extended-release tablets) is commercially available under the trademark Tegretol™ XR. Carbamazepine is an anticonvulsant and specific analgesic for trigeminal neuralgia. Its chemical name is 5H-dibenz[b,f]azepine-5-carboxamide. Carbamazepine can be administered alone or in combination with other drugs such as lithium (e.g. lithium carbonate) for the treatment of acute manic episodes in patients with bipolar disorder, or olanzapine for the treatment of patients with bipolar I disorder, manic or mixed episodes.

The extent of rupture formation, i.e. the size of the rupture, can vary according to membrane thickness, membrane brittleness or flexibility, membrane composition, extent of swelling or expansion of the core during use, the thickness or weight of the subcoat. A thick membrane (0.3-1.5 mm) will generally rupture to a lesser extent than a thin membrane (0.075-0.29 mm). A brittle membrane will generally rupture to a greater extent than a flexible membrane. The more a core expands overall during use, the greater the extent of rupture overall. As the amount or weight of the subcoat increases, the overall or final rupture size decreases.

After its initial formation in situ, the rupture can remain the same size or can increase in size during use. The formation of the rupture is abrupt; however, its subsequent increase in size can be gradual or intermittent.

Figure 18:
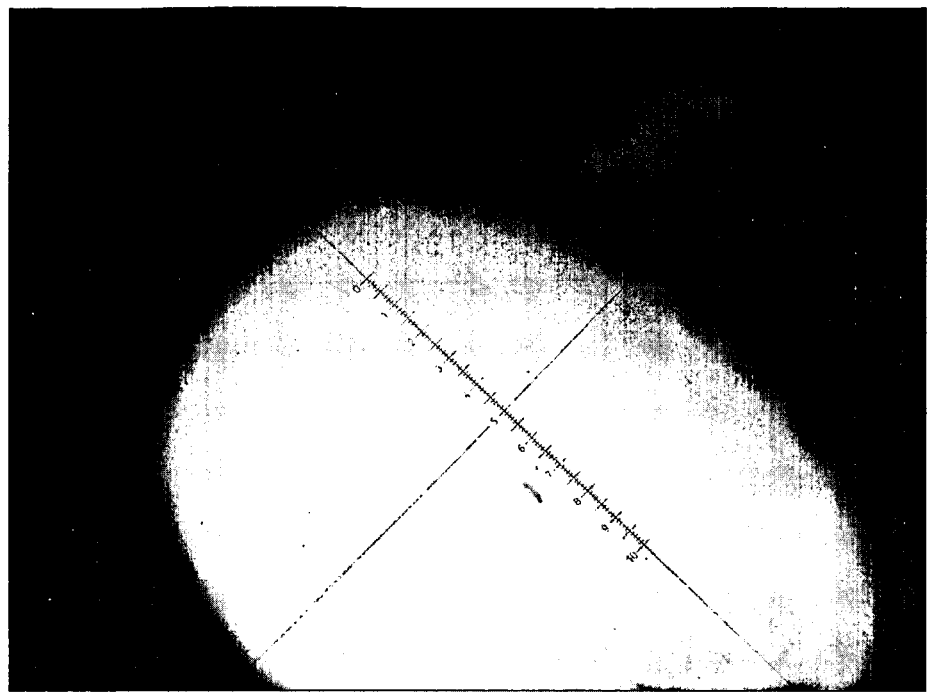
FIG. 18 depicts a 0.46 mm size rupture formed after exposure of an osmotic device of the invention to an aqueous environment. The measurement was taken 24 hours after initial exposure. The photograph corresponds to the carbamazepine tablet #4 with 15 mg subcoat disclosed in Example 6.
Figure 19:
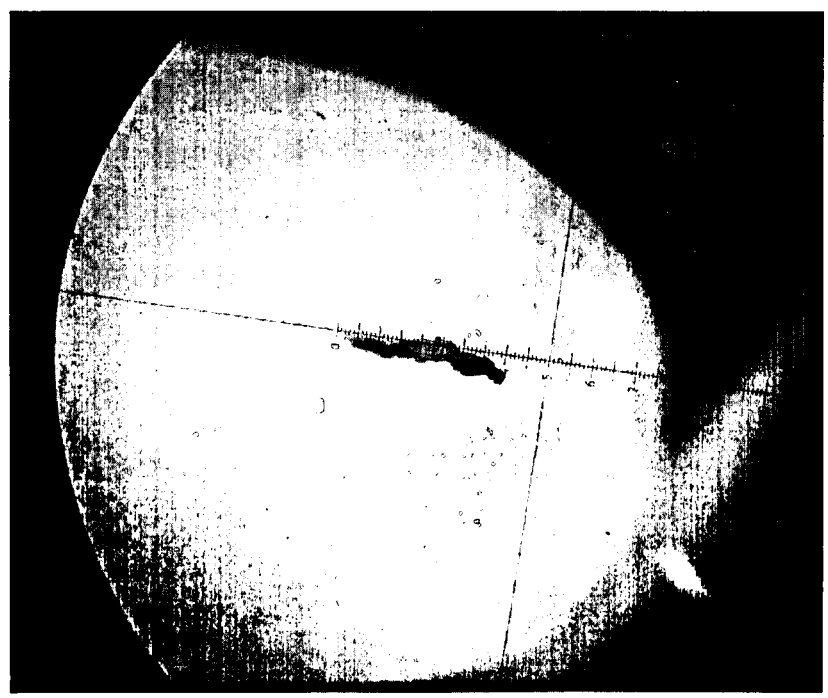
FIG. 19 depicts a 1.68 mm size rupture formed after exposure of an osmotic device of the invention to an aqueous environment. The measurement was taken 24 hours after initial exposure. The photograph corresponds to the carbamazepine tablet #3 with 10 mg subcoat disclosed in Example 6.
Figure 20:
FIG. 20 depicts a 5.91 mm size rupture formed after exposure of an osmotic device of the invention to an aqueous environment. The measurement was taken 24 hours after initial exposure. The photograph corresponds to the carbamazepine tablet #9 without subcoat disclosed in Example 6.

FIGS. 18, 19 and 20 include photographs depicting membrane ruptures of different sizes. Each photo was taken after exposure of a tablet to a release aqueous environment for 24 hours; however, the time at which rupture formation occurred was less than 24 hours. Rupture formation generally begins at about 1 hour, 2 hours, 3 hours, 4 hours, 5 hours, 6 hours, 7 hours, 8 hours, 9 hours, 10 hours, 11 hours up to 12 hours after exposure of an osmotic device of the invention to an aqueous environment. In some embodiments, rupture formation occurs within 1 to 12 hours, within 1.5 to 12 hours, within 2 to 11 hours, within 2 to 10 hours, within 3 to 8 hours, within 3 to 9 hours, within 3 to 10 hours, within 4 to 8 hours, within 4 to 9 hours, or within 4 to 10 hours after exposure of the device to an aqueous environment.

The extent of the membrane rupture was classified as small, medium or large, depending on the tablet diameter. For example, in the case of a 10.5 mm size round and simple radius tablet, the extent of the rupture was classified according to the table below:

| Type of rupture | Size (mm) | Reference |
|---|---|---|
| Small | 0.30-1.49 | S |
| Medium | 1.50-2.99 | M |
| Large | 3.00-6.00 | L |

The tablets of FIGS. 18-20 differed in the extent of rupture after exposure of an osmotic device of the invention to an aqueous environment. The results show that the frequency of large ruptures decreases as the amount or weight of subcoat increases, and the frequency of small ruptures increases as the amount or weight of subcoat increases. The tendency to smaller rupture sizes as the amount or weight of subcoat increases indicates that the subcoat controls the extent of rupture.

The formation of one or more ruptures in the absence of a subcoat was evaluated according to Example 7. Membrane thickness (weight), core composition, and membrane composition can impact the size, reproducibility, and timing of rupture formation. In general, absence of an acidic excipient from the core resulted in reproducible formation of one or more ruptures, primarily at the edge defining the preformed passageway. Addition of an acidic component to the core resulted in less frequent rupture formation and/or more small rupture formation preferentially over large rupture formation. Addition of a swell-reducing agent to the core results in less frequent rupture formation and/or small rupture formation.

As used herein, a "swell-reducing agent" is a compound or combination of one or more compounds that can be added to the core of the osmotic device to reduce the swelling of the core after its exposure to an aqueous environment, e.g. the swelling of the core caused by one or more swellable polymers or osmopolymers disclosed herein. Without being held bound to a particular mechanism of operation, a swell-reducing agent will dissolve after water is absorbed into the device and diffuse out of the device and reduce osmotic pressure, thereby reducing the swelling of the core of the device. By "osmopolymer" is meant a polymer that swells ≥2 times its initial volume in a compressed core. By "swellable polymer" is meant a polymer that swells >1 to <2 times its initial volume in a compressed core. One or more of the types of or specific excipients disclosed herein might also serve as a swell-reducing agent. In some embodiments, the core excludes a swell-reducing agent. In other embodiments, the core includes one or more swell-reducing agents. Suitable swell-reducing agents include: a non-aromatic carboxylic acid; a monocarboxylic acid, such as acetic acid, (+)-L-lactic acid, DL-lactic acid, DL-mandelic acid, gluconic acid, cinnamic acid, salicylic acid, and gentisic acid; a dicarboxylic acid, such as oxalic acid, 2-oxo-glutaric acid, malonic acid, (−)-L-malic acid, mucic acid, (+)-L-tartaric acid, fumaric acid, succinic acid, maleic acid, and terephthalic acid; a hydroxy-carboxylic acid; a hydroxy-dicarboxylic acid; a tricarboxylic acid, such as citric acid, or aromatic carboxylic acid; sulfonic acids, such as methanesulfonic acid, benzenesulfonic acid, toluenesulfonic acid, and napthalene-1,5-disulfonic acid; alpha-hydroxy acids such as tartaric acid, citric acid, ascorbic acid and malic acid; mineral acids such as hydrochloric acid, hydrobromic acid, sulfuric acid, sulfonic acid, sulfamic acid, phosphoric acid and nitric acid.

The extent to which the contents of the core might swell after exposure to an aqueous environment, but in the absence of a subcoat, can be determined according to Example 8. For example, the solid contents of a core (as loose powder or compressed solid) are placed in a volumetric container, i.e. a container that can be used to measure the volume of a solution and/or solid. The initial volume (Vi) of the solids is measured prior to exposure to an aqueous medium. The solids are then exposed to an aqueous medium and the final volume (Vf) of the undissolved solids remaining is measured. The ratio of Vf/Vi is used as an indicator of the extent of swelling that the core contents might undergo. If Vf/Vi≤1, then the core contents did not undergo any swelling. If Vf/Vi is >1 and <1.5, the swelling is considered minimal, and a device of the invention with a minimal swelling core will generally form only small apertures. If Vf/Vi is ≥1.5 and <2, the swelling is considered moderate, and a device of the invention with a moderate swelling core will generally form only small or medium apertures. If Vf/Vi is ≥2, the swelling is considered high, and a device of the invention with a high swelling core will generally form only medium or large apertures.

The subcoat of the invention can then be used to reduce the extent of or frequency of formation of ruptures in the membrane. Accordingly, an osmotic device with a low swelling core surrounded by a subcoat will form fewer and smaller small ruptures than an otherwise similar osmotic device with the no subcoat. An osmotic device with a moderate swelling core surrounded by a subcoat will form fewer and smaller ruptures than an otherwise similar osmotic device with the no subcoat. An osmotic device with a high swelling core surrounded by a subcoat will form fewer and smaller ruptures than an otherwise similar osmotic device with the no subcoat.

The osmotic device of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants, colorant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in tablet granulations. Such compounds include, by way of example and without limitation, acacia, poly(vinylpyrrolidone), compressible sugar (e.g., NuTab™), ethylcellulose, gelatin, liquid glucose, povidone, pregelatinized starch, tragacanth, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, cellulosics in nonaqueous solvents, combinations thereof and other materials known to one of ordinary skill in the art. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet diluents" or "fillers" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to promote the flowability of a granulation. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Such compounds include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present device can also employ one or more commonly known surface active agents or cosolvents that improve wetting or disintegration of the osmotic device core or layers.

It is contemplated that the osmotic device of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, glyceryl monostearate, PLURONIC® line (BASF), and the like; and amphoteric detergents, for example, alkyl aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly(ethylene), poly(vinyl acetate), poly(vinyl chloride), 1,3-butylene-glycoldimethacrylate, ethyleneglycol-dimethacrylate and methacrylate hydrogels.

It should be understood, that compounds used in the art of pharmaceutical formulations generally serve a variety of functions or purposes. Thus, if a compound named herein is mentioned only once or is used to define more than one term herein, its purpose or function should not be construed as being limited solely to that named purpose(s) or function(s).

Active agents include physiological substances or pharmacological active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleansing, confectionery and flavoring applications.

The active agent can be present in its neutral, ionic, salt, basic, acidic, natural, synthetic, diastereomeric, isomeric, enantiomerically pure, racemic, hydrate, solvate, chelate, complex, derivative, analog, pro-drug, amorphous, polymorphous, crude forms, crystalline forms, or other common forms. Unless otherwise specified, when a drug is referred to by name such reference includes all known forms of the drug.

Representative active agents include nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, diagnostic agents, antibacterial substances, antiparasitic compounds, antiviral compounds, analgesic drugs, antihistamines and decongestants, antiasthma drugs, anticoagulants, psychic energizers, anticonvulsants, antidepressants, antidiabetics, steroidal drugs, estrogen antagonist-agonist drugs, antipsychotics, hypnotics and sedatives, antihypertensives, angiotensin converting enzyme inhibitors, tranquilizers, anti-spasmodics and muscle contractants, local anesthetics, muscle relaxants, anti-Parkinson agents, anti-dementia and anti-Alzheimer, sympathomimetics drugs, cardiovascular drugs, diuretics, β-blockers, α-blockers, phosphodiesterase inhibitors, antilipemic agents, electrolytes, drugs that act on α-adrenergic receptors, CNS stimulants, and unclassified therapeutic agents. Exemplary nutrients and nutritional agents include minerals, trace elements, amino acids, lipotropic agents, enzymes and chelating agents. Exemplary hematological agents include hematopoietic agents, antiplatelet agents, anticoagulants, coumarin and indandione derivatives, coagulants, thrombolytic agents, antisickling agents, hemorrheologic agents, antihemophilic agents, hemostatics, plasma expanders and hemin. Exemplary endocrine and metabolic agents include sex hormones, uterine-active agents, bisphosphonates, antidiabetic agents, glucose elevating agents, adrenocortical steroids, parathyroid hormone, thyroid drugs, growth hormones, posterior pituitary hormones, octreotide acetate, imiglucerase, calcitonin-salmon, sodium phenylbutyrate, betaine anhydrous, cysteamine bitartrate, sodium benzoate and sodium phenylacetate, bromocriptine mesylate, cabergoline, agents for gout, and antidotes.

Exemplary cardiovascular agents include nootropic agents, antiarrhythmic agents, calcium channel blocking agents, vasodilators, antiadrenergics/sympatholytics, renin angiotensin system antagonists, antihypertensive combinations, agents for pheochromocytoma, agents for hypertensive emergencies, antihyperlipidemic agents, antihyperlipidemic combination products, vasopressors used in shock, potassium removing resins, edetate disodium, cardioplegic solutions, agents for patent ductus arteriosus, and sclerosing agents. Exemplary renal and genitourinary agents include interstitial cystitis agents, cellulose sodium phosphate, anti-impotence agents, acetohydroxamic acid (aha), genitourinary irrigants, cystine-depleting agents, urinary alkalinizers, urinary acidifiers, anticholinergics, urinary cholinergics, polymeric phosphate binders, vaginal preparations, and diuretics. Exemplary respiratory agents include bronchodilators, leukotriene receptor antagonists, leukotriene formation inhibitors, nasal decongestants, respiratory enzymes, lung surfactants, antihistamines, normarcotic antitussives, and expectorants. Exemplary central nervous system agents include CNS stimulants, narcotic agonist analgesics, narcotic agonist-antagonist analgesics, central analgesics, acetaminophen, salicylates, normarcotic analgesics, nonsteroidal anti-inflammatory agents, agents for migraine, antiemetic/antivertigo agents, antianxiety agents, antidepressants, antipsychotic agents, cholinesterase inhibitors, nonbarbiturate sedatives and hypnotics, nonprescription sleep aids, barbiturate sedatives and hypnotics, general anesthetics, anticonvulsants, muscle relaxants, antiparkinson agents, adenosine phosphate, cholinergic muscle stimulants, disulfuram, smoking deterrents, riluzole, hyaluronic acid derivatives, and botulinum toxins. Exemplary gastrointestinal agents including *H. pylori* agents, histamine H2 antagonists, proton pump inhibitors, sucralfate, prostaglandins, antacids, gastrointestinal anticholinergics/antispasmodics, mesalamine, olsalazine sodium, balsalazide disodium, sulfasalazine, celecoxib, infliximab, esomeprazole, famotidine, lansoprazole, omeprazole, pantoprazole, rabeprazole, tegaserod maleate, laxatives, antidiarrheals, antiflatulents, lipase inhibitors, GI stimulants, digestive enzymes, gastric acidifiers, hydrocholeretics, gallstone solubilizing agents, mouth and throat products, systemic deodorizers, and anorectal preparations. Exemplary anti-infective agents including penicillins, such as amoxicilin, cephalosporins and related antibiotics, carbapenem, monobactams, chloramphenicol, quinolones, fluoroquinolones, tetracyclines, macrolides, such as azithromycin, clarithromycin, and the like, spectinomycin, streptogramins, vancomycin, oxalodinones, lincosamides, oral and parenteral aminoglycosides, colistimethate sodium, polymyxin B sulfate, bacitracin, metronidazole, sulfonamides, nitrofurans, methenamines, folate antagonists, antifungal agents, such as fluconazole, voriconazole, and the like, antimalarial preparations, antituberculosis agents, amebicides, antiviral agents, antiretroviral agents, leprostatics, antiprotozoals, anthelmintics, and CDC anti-infective agents. Exemplary biologic and immunological agents including immune globulins, monoclonal antibodies, antivenins, agents for active immunization, allergenic extracts, immunologic agents, and antirheumatic agents. Exemplary antineoplastic agents include alkylating agents, antimetabolites, antimitotic agents, epipodophyllotoxins, antibiotics, hormones, enzymes, radiopharmaceuticals, platinum coordination complex, anthracenedione, substituted ureas, methylhydrazine derivatives, imidazotetrazine derivatives, cytoprotective agents, DNA topoisomerase inhibitors, biological response modifiers, retinoids, rexinoids, monoclonal antibodies, protein-tyrosine kinase inhibitors, porfimer sodium, mitotane (o, p'-ddd), and arsenic trioxide. Exemplary diagnostic agents include in vivo diagnostic aids, in vivo diagnostic biologicals, and radiopaque agents.

Representative antibacterial substances are beta-lactam antibiotics, tetracyclines, chloramphenicol, neomycin, gramicidin, bacitracin, sulfonamides, aminoglycoside antibiotics, tobramycin, nitrofurazone, nalidixic acid, penicillin, tetracycline, oxytetracycline, chlorotetracycline, erythromycin, cephalosporins and analogs and the antimicrobial combination of fludalanine/pentizidone. Other representative antibacterial agents include of the poorly water-soluble pyrridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof.

Representative antiparasitic compounds are ivermectin, bephenium, hydroxynaphthoate, praziquantel, nifurtimox, benznidazol, dichlorophen and dapsone. Representative antimalarial compounds are 4-aminoquinolines, 8-aminoquinolines and pyrimethamine.

Representative antiviral compounds are protease inhibitors, neuramidinase inhibitors, commercially available compounds, acyclovir and interferon.

Representative anti-inflammatory drugs include rofecoxib, celecoxib, etodolac, flurbiprofen, ibuprofen, ketoprofen, ketorolac, nabumetone, piroxicam, suprofen, tolmetin, zileuton, steroids, cyclooxygenase inhibitors, cortisone, hydrocortisone, betamethasone, dexamethasone, fluocortolone, prednisolone, phenylbutazone, triamcinolone, sulindac, indomethacin, salicylamide, naproxen, colchicine, fenoprofen, diclofenac, indoprofen, dexamethasone, allopurinol, oxyphenbutazone, probenecid and sodium salicylamide.

Representative analgesic drugs are diflunisal, aspirin, ibuprofen, profen-type compounds, morphine, codeine, levorphanol, hydromorphone, oxymorphone, oxycodone, hydrocodone, naloxene, levallorphan, etorphine, fentanyl, bremazocine, meperidine, nalorphine, tramadol, and acetaminophen.

Representative antihistamines and decongestants are acrivastine, astemizole, norastemizol, brompheniramine, cetirizine, clemastine, diphenhydramine, ebastine, famotidine, fexofenadine, meclizine, nizatidine, perilamine, promethazine, ranitidine, terfenadine, chlorpheniramine, cimetidine, tetrahydrozoline, tripolidine, loratadine, desloratadine, antazoline, and pseudoephedrine.

Representative antiasthma drugs are theophylline, ephedrine, beclomethasone dipropionate and epinephrine.

Representative anticoagulants are heparin, bishydroxycoumarin, and warfarin.

Representative psychic energizers are isocoboxazid, nialamide, phenelzine, imipramine, tranycypromine, and pargylene.

Representative anticonvulsants are clonazepam, phenobarbital, mephobarbital, primidone, enitabas, diphenylhydantion, ethltion, pheneturide, ethosuximide, diazepam, phenyloin carbamazepine, lamotrigine, lorazepam, levetiracetam, oxcarbazepine, topiramate, valproic acid, chlorazepate, gabapentin, felbamate, tiagabine and zonisamide Representative antidepressants are amitriptyline, chlordiazepoxide perphenazine, protriptyline, imipramine, doxepin, venlafaxine, o-desmethyl venlafaxine, citalopram, escitalopram, bupropion, clomipramine, desipramine, nefazodone, fluoxetine, fluvoxamine, maprotiline, mirtazapine, nortriptyline, paroxetine, phenelzine, tranylcypromine, sertraline, trazodone, trimipramine, and amoxapine Representative antidiabetics are sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide, repaglinide, insulin, somatostatin and its analogs, chlorpropamide, isophane insulin, protamine zinc insulin suspension, globin zinc insulin, and extended insulin zinc suspension.

Representative antineoplastics are chlorambucil, cyclophosphamide, triethylenemelamine, thiotepa, hexamethylmelamine, busulfan, carmustine, lomustine, dacarbazine, arabinoside cytosine, mercaptopurine, azathiprine, vincristine, vinblastine, taxol, etoposide, actinomycin D, daunorubicin, doxorubicin, bleomycin, mitomycin; cisplatin; hydroxyurea, procarbazine, aminoglutethimide, tamoxifen, adriamycin, fluorouracil, methotrexate, mechlorethamine, uracil mustard, 5-fluorouracil, 6-6-thioguanine and procarbazine asparaginase.

Representative steroidal drugs are prednisone, prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; progestational steroids such as progesterone, 19-norpregn-4-ene-3,20-dione, 17-hydroxy-19-nor-17-α-pregn-5 (10)-ene-20-yn-3-one, 17α-ethynyl-17-hydroxy-5(10)-estren-3-one, and 9β, 10α-pregna-4,6-diene-3,20-dione.

Representative estrogen antagonist-agonist drugs are clomiphene citrate and raloxifene HC1.

Representative antipsychotics are prochlorperazine, lithium carbonate, lithium citrate, thioridazine, molindone, fluphenazine, trifluoperazine, perphenazine, amitriptyline, trifluopromazine, chlorpromazine, clozapine, haloperidol, loxapine, mesoridazine, olanzapine, quetiapine, ziprasidone, risperidone, pimozide, mesoridazine besylate, chlorprothixene, and thiothixene.

Representative hypnotics and sedatives are pentobarbital sodium, phenobarbital, secobarbital, thiopental, heterocyclic hypnotics, dioxopiperidines, imidazopyridines, such as zolpidem tartrate, glutarimides, diethylisovaleramide, α-bromoisovaleryl urea, urethanes, disulfanes.

Representative antihypertensives are nifedipine, verapamil, diltiazem, felodipine, amlodipine, isradipine, nicardipine, nisoldipine, nimodipine, bepridil, enalapril, captopril, lisinopril, benazepril, enalaprilat, espiapril, fosinopril, moexipril, quinapril, ramipril, perindopril, trandolapril, furosemide, bumetanide, ethacrynic acid, torsemide, muzolimide, azosemide, piretanide, tripamide, hydrochlorothiazide, chlorthalidone, indapamide, metozalone, cyclopenthiazide, xipamide, mefruside, dorzolamide, acetazolamide, methazolamide, ethoxzolamide, cyclothiazide, clopamide, dichlorphenamide, hydroflumethiazide, trichlormethiazide, polythiazide, benzothiazide, spironolactone, methyldopa, hydralazine, clonidine, chlorothiazide, deserpidine, timolol, propranolol, metoprolol, pindolol, acebutolol, prazosin hydrochloride, methyl dopa (L-β-3,4-dihydroxyphenylalanine), pivaloyloxyethyl ester of α-methyldopa hydrochloride dihydrate, candesartan cilexetil, eprosartan mesylate, losartan potassium, olmersartan medoxomil, telmisartan, valsartan, reserpine and lercanidipine.

Representative angiotensin converting enzyme inhibitors are enalapril, captopril, lisinopril, benazepril, enalaprilat, espiapril, fosinopril, moexipril, quinapril, ramipril, perindopril, and trandolapril.

Representative tranquilizers are chloropromazine, promazine, fluphenazine, reserpine, deserpidine, meprobamate, and benzodiazepines (anxyiolitic, sedatives, and hypnotics) such as alprazolam, chlordiazepoxide, diazepam, lorazepam, oxazepam, temazepam, and triazolam.

Representative anti-spasmodics and muscle contractants are atropine, scopolamine, methscopolamine, oxyphenonium, papaverine, and prostaglandins such as PGE1 PGE2 PGF1α PGF2α and PGA.

Representative local anesthetics are benzocaine, procaine, lidocaine, maepaine, piperocaine, tetracaine and dibucaine.

Representative muscle relaxants are alcuronium, alosetron, aminophylline, baclofen, carisoprodol, chlorphenesin, chlorphenesin carbamate, chlorzoxazone, chlormezanone, dantrolene, decamethonium, dyphylline, eperisione, ethaverine, gallamine triethiodide, hexafluorenium, metaxalone, metocurine iodide, orphenadrine, pancuronium, pap averine, pipecuronium, theophylline, tizanidine, tolperisone, tub ocurarine, vecuronium, idrocilamide, ligustilide, cnidilide, senkyunolide, succinylcholine-chloride, danbrolene, cyclobenzaprine, methocarbamol, diazepam, mephenesin, methocarbomal, trihexylphenidyl, pridinol (pridinolum), and biperiden.

Representative anti-Parkinson agents are carbidopa, levodopa, ropinirole, pergolide mesylate, rasagiline, pramipexole, entacapone, benzacide, bromocriptine, selegiline, amantadine, trihexylphenidyl, biperiden, pridinol mesylate, and tolcapone.

Representative anti-dementia and anti-Alzheimer disease agents are memantine, donepexil, galantamine, rivastigmine, and tacrine Representative sympathomimetic drugs are albuterol, epinephrine, amphetamine ephedrine and norepinephrine.

Representative cardiovascular drugs are procainamide, procainamide hydrochloride, amyl nitrite, nitroglycerin, dipyredamole, sodium nitrate and mannitol nitrate.

Representative diuretics are chlorothiazide, acetazolamide, methazolamide, triamterene, furosemide, indapamide, flumethiazide, bumetanide, ethacrynic acid, torsemide, muzolimide, azosemide, piretanide, tripamide, hydrochlorothiazide, chlorthalidone, indapamide, metozalone, cyclopenthiazide, amiloride, xipamide, mefruside, dorzolamide, ethoxzolamide, cyclothiazide, clopamide, dichlorphenamide, hydroflumethiazide, trichlormethiazide, polythiazide and benzothiazide.

Representative β-blockers are caravedilol (carvedilol), pindolol, propranolol, practolol, metoprolol, esmolol, oxprenolol, timolol, atenolol, alprenolol, sotalol, carteolol, nadolol, betaxolol, penbutolol, acebutolol, and bisoprolol.

Representative α-blockers are doxazosin, prazosin, terazosin, labetalol, alfuzosin, ergotamine, phenoxybenzamine, methysergide, mirtazapine, tamsulosin, and yohimbine.

Representative phosphodiesterase inhibitors are vardenafil HC1 and sildenafil citrate.

Representative antilipemic agents are atorvastatin, cerivastatin, clofibrate, fluvastatin, gemfibrozil, lovastatin, mevinolinic acid, niacin, pravastatin, and simvastatin.

Representative antigout drugs are colchicine, allopurinol, probenecid, sulfinpyrazone, and benzbromarone.

Representative nutritional agents are ascorbic acid, niacin, nicotinamide, folic acid, choline biotin, panthothenic acid, and vitamin B12, essential amino acids; essential fats.

Representative ophthalmic agents are pilocarpine, pilocarpine salts such as pilocarpine nitrate, pilocarpine hydrochloride, dichlophenamide, atropine, atropine sulfate, scopolamine and eserine salicylate.

Representative electrolytes are calcium gluconate, calcium lactate, potassium chloride, potassium sulfate, sodium chloride, potassium fluoride, ferrous lactate, ferrous gluconate, ferrous sulfate, ferrous fumurate and sodium lactate.

Representative drugs that act on α-adrenergic receptors are clonidine hydrochloride, prazosin, tamsulosin, terazosin, and doxazosin.

Representative mild CNS stimulants are caffeine, modafinil, and methylphenidate hydrochloride.

The formulation of the invention can also be use with unclassified therapeutic agents such as clopidrogel, which is indicated for the reduction of atherosclerotic events (myocardial infarction, stroke, and vascular death) in patients with atherosclerosis documented by recent stroke, recent myocardial infarction, or established peripheral arterial disease.

Particular combinations of active agents that can be provided by the present controlled release device include: 1) a drug in the core from a first therapeutic class and a different drug in the external drug-containing coat from the same therapeutic class; 2) a drug in the core from a first therapeutic class and a different drug in the external drug-containing coat from a different therapeutic class; 3) a drug in the core having a first type of biological activity and a different drug in the external drug-containing coat having about the same biological activity; 4) a drug in the core having a first type of biological activity and a different drug in the external drug-containing coat having a different second type of biological activity, 5) the first active agent is pridinol and the second active agent is a selective or specific COX-II inhibitor agent; 6) the first drug is an analgesic agent and the drug in the external drug-containing coat is and anti-inflammatory agent; 7) the analgesic and anti-inflammatory agents are selected from the group consisting of an non-steroidal anti-inflammatory agent, a steroidal anti-inflammatory agent, an opioid receptor agonist agent, and a selective or specific COX-II inhibitor agent; 8) the drug in the core and the drug in the external drug-containing coat are antihypertensive agents selected from the group consisting of a calcium channel blocker agent, an angiotensin converting enzyme inhibitor agent, a diuretic agent and a beta-adrenergic antagonist agent; 9) the drug in the core and the drug in the external drug-containing coat are diabetic agents selected from the following main groups of oral antidiabetic drugs available: sulphonylureas, such as tolbutamide, chlorpropamide, tolazamide, acetohexamide, glibenclamide, gliclazide, 1-butyl-3-metanilylurea, carbutamide, glibonuride, glipizide, glyburide, gliquidone, glisoxepid, glybuthiazole, glibuzole, glyhexamide, glymidine, glypinamide, phenbutamide, and tolcyclamide; thiazolidinediones (glitazones), such as rosiglitazone, pioglitazone, and troglitazone; biguanidines, such as metformin; and other antidiabetic agents, such as nateglinide and repaglinide; 10) the drug in the core is a decongestant and the drug in the external drug-containing coat is an antihistamine; 11) the drug in the core and the drug in the external drug-containing coat are anti-incontinence drugs; 12) the anti-incontinence drugs are selected from the group consisting of oxybutynin, tolterodine, and darifenacin; 13) the drug in the core is an antidepressant and the drug in the external drug-containing coat is for the treatment of Dementia; 14) the drug in the core is an antidepressant and the drug in the external drug-containing coat is an antianxiety drug; 15) the drug in the core is an antidepressant and the drug in the external drug-containing coat is an antipsychotic drug; 16) the drug in the core is an antianxiety drug and the drug in the external drug-containing coat is for the treatment of Dementia; 17) the drug in the core is an antianxiety drug and the drug in the external drug-containing coat is an antipsychotic drug; 18) the drug in the core is an antianxiety drug and the drug in the external drug-containing coat is an antimanic drug; 19) the drug in the core is an antipsychotic drug and the drug in the external drug-containing coat is an antimanic drug; 20) the drug in the core and the drug in the external drug-containing coat are for the treatment of Dementia; 21) the drug in the core is for the treatment of Dementia and the drug in the external drug-containing coat is an antianxiety drug; 22) the drug in the core is an anticonvulsant drug and the drug in the external drug-containing coat is an antianxiety drug; 23) the drug in the core is an anticonvulsant drug and the drug in the external drug-containing coat is an antipsychotic drug; 24) the drug in the core is an anticonvulsant drug and the drug in the external drug-containing coat is for the treatment of Dementia; 25) the drug in the core is anticonvulsant and the drug in the external drug-containing coat is an antimanic drug; 26) the drug in the core is an antiparkinsonian drug and the drug in the external drug-containing coat is an antidepressant; 27) the drug in the core is an antiparkinsonian drug and the drug in the external drug-containing coat is for the treatment of Dementia; 28) the drug in the core and the drug in the external drug-containing coat are antiparkinsonian drugs; 29) the drug in the core and the drug in the external drug-containing coat are mild CNS stimulants; 30) the drug in the core and the drug in the external drug-containing coat are opioid analgesics; 31) the drug in the core is an opioid analgesic and the drug in the external drug-containing coat is a non steroidal anti-inflammatory drug; 32) the drug in the core and the drug in the external drug-containing coat are non steroidal anti-inflammatory drugs; 33) the drug in the core is a non steroidal anti-inflammatory drug and the drug in the external drug-containing coat is a steroidal drug; 34) the drug in the core and the drug in the external drug-containing coat are antigout drugs; 35) the drug in the core and the drug in the external drug-containing coat are antilipemic drugs; and 36) the drug in the core is carisoprodol and the drug in the external drug-containing coat is diclofenac; 37) the drug in the external drug containing-coating is different than the drug in the subcoat; 38) the drug in the external drug containing-coat is different than the drug in the subcoat and the drug in the core; 39) the drug in the external drug containing-coat is different than the drug in the subcoat and the drug in the subcoat is different than the drug in the core; 40) the drug in the external drug-containing coat is the same as the drug in the core; 41) the drug in the external drug-containing coat is the same as the drug in the subcoat; 42) the drug in the external drug-containing coat is the same as the drug in the subcoat and the drug in the subcoat is the same as the drug in the core; 43) the drug in the external drug-containing coat is the same as the drug in the core; and the drug in the subcoat is different than the drug in the core;

44) the external drug-containing coat comprises carbidopa and optionally levodopa; the subcoat comprises levodopa, and the core comprises amantadine; 45) the external drug-containing coat comprises ondansetron, the subcoat comprises alprazolam; and the core comprises venlafaxine; 46) the external drug-containing coat comprises carbidopa and optionally levodopa, the subcoat comprises levodopa, and the core comprises ropinirole; 47) the external drug-containing coat comprises ondansetron, the subcoat comprises quetiapine, and the core comprises venlafaxine; 48) the external drug-containing coat comprises quetiapine, the subcoat comprises divalproex sodium, and the core comprises lithium; 49) the external drug-containing coat comprises carbidopa and optionally levodopa, the subcoat comprises amantadine, and the core comprises levodopa; 50) the external drug-containing coat comprises carbidopa and optionally levodopa, the subcoat comprises entacapone, and the core comprises levodopa; 51) the external drug-containing coat comprises ergotamine, the subcoat comprises naproxen; and the core comprises domperidone; and 52) the external drug-containing coat comprises carbidopa, the subcoat comprises levodopa, and the core comprises sildenafil.

The above-mentioned list should not be considered exhaustive and is merely exemplary of the many embodiments considered within the scope of the invention. Many other active agents can be administered with the formulation of the present invention.

The therapeutic compound(s) contained within the present osmotic device can be formulated as its pharmaceutically acceptable salts. As used herein, "pharmaceutically acceptable salts" refer to derivatives of the disclosed compounds wherein the therapeutic compound is modified by making an acid or base salt thereof. Examples of pharmaceutically acceptable salts include, but are not limited to, mineral or organic acid salts of basic residues such as amines; alkali or organic salts of acidic residues such as carboxylic acids; and others known to those of ordinary skill. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfonic, sulfamic, phosphoric, nitric and others known to those of ordinary skill; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill. The pharmaceutically acceptable salts of the present invention can be synthesized from the parent therapeutic compound which contains a basic or acidic moiety by conventional chemical methods. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamine pyrophosphates (TPP), flavin mononucleotide (FMN), flavin adenine dinucleotide (FAD), Nicotinamide adenine dinucleotide (NAD), Nicotinamide adenine dinucleotide phosphate (NADP), Coenzyme A (CoA), pyridoxal phosphate, biocytin, tetrahydrofolic acid, coenzyme B12, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and others known to those of ordinary skill required in the human diet. Thus, the term "mineral" as used herein includes, without limitation, calcium, iron, zinc, selenium, copper, iodine, magnesium, phosphorus, chromium and others known to those of ordinary skill, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill. As will be appreciated, essentially any dietary supplement may be incorporated into the present osmotic device.

The amount of therapeutic compound incorporated in each device will be at least one or more unit dose and can be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. A dosage form according to the invention that comprises two or more active agents can include subtherapeutic amounts of one or more of those active agents such that an improved, additive or synergistic clinical benefit is provided by the dosage form. By subtherapeutic amount is meant an amount less than that typically recognized as being therapeutic on its own in a subject to which the dosage form is administered. Therefore, a dosage form can comprise a subtherapeutic amount of a first drug and a therapeutic amount of a second drug. Alternatively, a dosage form can comprise a subtherapeutic amount of a first drug and a subtherapeutic amount of a second drug.

As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, generally about 100% or more of the applicable RDA.

For nasal, oral, buccal, and sublingual administration, the device may be in the form of a caplet, tablet or pill. For rectal administration, the device can be included in a suppository, tablet, implant or patch for release of a therapeutic compound into the intestines, sigmoid flexure and/or rectum.

The term "unit dosage form" is used herein to mean a device containing a quantity of the therapeutic compound, said quantity being such that one or more predetermined units may be provided as a single therapeutic administration.

If desired, the device of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The following examples should not be considered exhaustive, but merely illustrative of only a few of the many embodiments contemplated by the present invention. The methods described herein can be followed to prepare osmotic devices according to the invention.

EXAMPLE 1

The following procedure is used to prepare a rupturing controlled release device containing alprazolam (1, 2, and 4 mg strength) in the core. The osmotic device tablets contain the following ingredients in the amounts indicated:

| INGREDIENT | AMOUNT (MG) Alprazolam Strength⇒ | | |
|---|---|---|---|
| | 1 | 2 | 4 |
| CORE | | | |
| Alprazolam | 1.00 | 2.00 | 4.00 |
| Polysorbate 20 (Surfactant) | 2.10 | 4.20 | 8.40 |
| Microcrystalline Cellulose PH 101 (Diluent) | 11.25 | 22.50 | 45.00 |
| Sodium Chloride (Osmagent) | 21.00 | 42.00 | 84.00 |
| Povidone K30 (Binder) | 2.10 | 4.20 | 8.40 |
| Polyethylene Oxide WSR 205 (Osmopolymer 1) | 21.00 | 42.00 | 84.00 |
| HPMC K4M (Osmopolymer 2) | 10.50 | 21.00 | 42.00 |
| Colloidal Silicon Dioxide (Glidant) | 0.35 | 0.70 | 1.40 |
| Magnesium Stearate (Lubricant) | 0.70 | 1.40 | 2.80 |
| Purified water* | 25.00 | 50.00 | 100.00 |
| COATING A | | | |
| Cellulose Acetate 320-S (Water insoluble polymer) | 5.00 | 10.00 | 20.00 |
| Cellulose Acetate 398-10 (Water insoluble polymer) | 5.00 | 10.00 | 20.00 |
| Polyethylene glycol 400 (Plasticizer) | 0.50 | 1.00 | 2.00 |
| Acetone* (organic solvent) | 178.5 | 357.00 | 714.00 |
| Purified water* | 31.50 | 63.00 | 126.00 |
| COATING B | | | |
| Opadry Y 30 18084-A (aqueous film-coating) | 2.50 | 5.00 | 10.00 |
| Colorant | 0.01 | 0.02 | 0.04 |
| Purified Water* | 25.00 | 50.00 | 100.00 |

*denotes a component used during manufacture of the osmotic device but which is substantially absent (present in an amount of less than about 10% or less than 5% by wt.) in the final dosage form First, the core composition is prepared by placing alprazolam, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores.

A first composition (coating A) to cover the core is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A finish coat (coating B) comprising Opadry and a colorant in purified water is applied onto the film-coated tablets to obtain the osmotic device tablets.

EXAMPLE 2

The following procedure is used to prepare a rupturing controlled release device containing alprazolam (1, 2, and 4 mg strength) in the core. The osmotic device tablets contain the following ingredients in the amounts indicated:

| INGREDIENT | AMOUNT (mg) Alprazolam Strength⇒ | | |
|---|---|---|---|
| | 1 | 2 | 4 |
| CORE | | | |
| Alprazolam | 1.00 | 2.00 | 4.00 |
| Polysorbate 20 (Surfactant) | 2.10 | 4.20 | 8.40 |
| Microcrystalline Cellulose PH 101 (Diluent) | 11.25 | 22.50 | 45.00 |
| Sodium Chloride (Osmagent) | 21.00 | 42.00 | 84.00 |
| Povidone K30 (Binder) | 2.10 | 4.20 | 8.40 |
| Polyethylene Oxide WSR 205 (Osmopolymer 1) | 21.00 | 42.00 | 84.00 |
| HPMC K4M (Osmopolymer 2) | 10.50 | 21.00 | 42.00 |
| Colloidal Silicon Dioxide (Glidant) | 0.35 | 0.70 | 1.40 |
| Magnesium Stearate (Lubricant) | 0.70 | 1.40 | 2.80 |
| Purified water* | 25.00 | 50.00 | 100.00 |
| SUBCOAT | | | |
| HPMC E5 (film forming polymer) | 10.50 | 21.00 | 42.00 |
| PEG 400 (Plasticizer) | 0.21 | 0.42 | 0.84 |
| Purified water* | 105.00 | 210.00 | 420.00 |
| COATING A | | | |
| Cellulose Acetate 320-S (Water insoluble polymer) | 5.00 | 10.00 | 20.00 |
| Cellulose Acetate 398-10 (Water insoluble polymer) | 5.00 | 10.00 | 20.00 |
| Polyethylene glycol 400 (Plasticizer) | 0.50 | 1.00 | 2.00 |
| Acetone* (organic solvent) | 178.5 | 357.00 | 714.00 |
| Purified water* | 31.50 | 63.00 | 126.00 |
| COATING B | | | |
| Opadry Y 30 18084-A (aqueous film-coating) | 2.50 | 5.00 | 10.00 |

-continued

| INGREDIENT | AMOUNT (mg) Alprazolam Strength⇒ | | |
|---|---|---|---|
| | 1 | 2 | 4 |
| Colorant | 0.01 | 0.02 | 0.04 |
| Purified Water* | 25.00 | 50.00 | 100.00 |

*denotes a component used during manufacture of the osmotic device but which is substantially absent (present in an amount of less than about 10% or less than 5% by wt.) in the final dosage form.

First, the drug-containing core composition is prepared by placing alprazolam, two osmopolymers, a diluent, an osmagent, and a binder in a high shear mixer and mix for 5 minutes. The granulation process is initiated by the gradual addition of a granulating solution containing a surfactant and purified water to the high shear with continuous blending to produce a wet blend. Next, the wet blend is granulated and dried at 40-50° C. for 20 minutes in a fluid bed to remove the water. Then, the dry granules are screened through a 30 USP mesh screen for size reduction. Next, the screened granules are mixed with a glidant and a lubricant, that have been previously passed through a 60 mesh screen, in a V-Blender during 5 minutes. This final blend is tabletted to provide the cores.

A subcoat composition to cover the drug-containing core is prepared as follows: HPMC E5 and PEG 400 are dissolved in purified water and the solution is applied onto the drug-containing core.

A second composition (coating A) to cover the first composition is prepared as follows: two cellulose esters and a plasticizer are added to organic solvent and purified water, and mixed thoroughly to form a polymer solution. This solution is sprayed onto the tablets in a perforated pan coater to form film-coated cores. A 0.5 mm hole is drilled through the coating to provide perforated film-coated tablets.

A finish coat (coating B) comprising Opadry and a colorant in purified water is applied onto the film-coated tablets to obtain the osmotic device tablets.

EXAMPLE 3

The following procedure is used to prepare a rupturing controlled release device containing sildenafil (50 and 100 mg strengths) in the core and levodopa (100 and 200 mg strengths) in the subcoat, and carbidopa (25 and 50 mg strengths) in an immediate or rapid release external coat. The osmotic device tablets contain the following ingredients in the amounts indicated:

| INGREDIENT/FUNCTIONAL CATEGORY | AMOUNT (mg) | | |
|---|---|---|---|
| Sildenafil CR Strength⇒ | 50 | 50 | 100 |
| Levodopa ER Strength⇒ | 100 | 200 | 200 |
| Carbidopa IR Strength⇒ | 25 | 50 | 50 |
| CORE | | | |
| Sildenafil | 50 | 50 | 100 |
| Osmopolymer 1 | 20-50 | 20-50 | 20-100 |
| Osmopolymer 2 | 0-50 | 0-50 | 0-100 |
| Diluent | 10-50 | 10-50 | 10-100 |
| Binder | 1-20 | 1-20 | 1-40 |
| Osmagent | 2-40 | 2-40 | 2-80 |
| Glidant | 0.1-5 | 0.1-5 | 0.1-10 |
| Lubricant | 0.1-5 | 0.1-5 | 0.1-10 |

-continued

| INGREDIENT/FUNCTIONAL CATEGORY | AMOUNT (mg) | | |
|---|---|---|---|
| Sildenafil CR Strength⇒ | 50 | 50 | 100 |
| Levodopa ER Strength⇒ | 100 | 200 | 200 |
| Carbidopa IR Strength⇒ | 25 | 50 | 50 |
| SUBCOAT | | | |
| Levodopa | 100 | 200 | 200 |
| Film forming polymer | 20-100 | 20-200 | 20-200 |
| Plasticizer | 5-50 | 5-80 | 5-80 |
| Disintegrant or water soluble polymer | 5-50 | 5-80 | 5-80 |
| COATING A | | | |
| Cellulose Ester 1 | 20-50 | 20-50 | 20-50 |
| Cellulose Ester 2 | 0-50 | 0-50 | 0-50 |
| Plasticizer | 1-10 | 1-10 | 1-10 |
| COATING B | | | |
| Carbidopa | 25 | 50 | 50 |
| Film forming polymer | 20-80 | 20-160 | 20-160 |
| Plasticizer | 1-25 | 1-50 | 1-50 |
| Disintegrant or water soluble polymer | 5-30 | 5-60 | 5-60 |
| COATING C | | | |
| Film forming polymer | 10-25 | 10-25 | 10-25 |
| Opaquant | 1-10 | 1-10 | 1-10 |
| Plasticizer | 1-5 | 1-5 | 1-5 |

The sildenafil composition of the core is prepared as follows: the osmopolymer 1 and 2 and the filler are first individually screened in a rotary mill with a 991 μm screen at less than 300 rpm for size reduction, and mix with the osmagent (previously milled using a hammer mill with a 0033 screen). Then, the sildenafil and the binder are added and mix in a mixer granulator for 5 minutes to form a homogenous powder blend. The granulation process is initiated by the gradual addition of purified water to the powder blend, with continuous mixing, to change the consistency of the dry powder ingredients to granules. The wet granulation is dried in a static bed at 40-50° C. or in a fluid bed at 40-50° C. for humidity reduction. Next, the dry granules are milled using a rotary mill with a 1575 μm screen at less than 1200 rpm for size reduction. Next, the glidant and the lubricant (previously sieved through a 30-mesh screen) are added and mixed for about 5 minutes. The resulting mixture is compressed in a compressor with 6-11 mm diameter punches to form the sildenafil tablet.

The subcoat composition is prepared as follows: levodopa, the film forming polymer, the plasticizer and the disintegrant are mixed in purified water. This polymer mixture is sprayed onto the sildenafil tablets in a perforated pan coater to obtain the core surrounded by the subcoat.

A semipermeable membrane composition is prepared as follows: cellulose ester 1, cellulose ester 2, and a plasticizer of low molecular weight are dissolved in acetone and purified water. The solution is sprayed onto the cores to obtain coated cores. The semipermeable membrane weight range is approximately between 21 and 110 mg. The coated cores are then perforated with a laser equipment to form at least one passageway of 0.2-1.5 mm of diameter.

Coating B is prepared by mixing carbidopa, film forming polymer, plasticizer, and disintegrant in purified water. This polymer mixture is sprayed onto the tablets in a pan coater to obtain film coated cores.

The final coating is prepared by mixing film forming polymer, plasticizer and opaquant in a solvent. This composition is sprayed onto the film coated cores in a pan coater.

The in vitro testing is performed with USP Type 2, in 900 ml of 0.1 N HCl, at 37° C. during 24 hours. The samples were tested by RP-HPLC.

| Sildenafil | | | Levodopa | | | Carbidopa | | |
|---|---|---|---|---|---|---|---|---|
| Time | Range (%) | | Time | Range (%) | | Time | Range (%) | |
| (h) | Min | Max | (h) | Min | Max | (min) | Min | Max |
| 0 | 0 | 0 | 0 | 0 | 0 | 0 | 0 | 0 |
| 0.5 | 0 | 0 | 1 | 5 | 28 | 0.25 | 82 | 95 |
| 1 | 0.5 | 2.5 | 2 | 20 | 66 | 0.5 | 83 | 98 |
| 3 | 4.5 | 12 | 3 | 40 | 95 | 1 | 85 | 100 |
| 9 | 35 | 65 | 4 | 60 | 97 | | | |

-continued

| Sildenafil | | | Levodopa | | | Carbidopa | | |
|---|---|---|---|---|---|---|---|---|
| Time | Range (%) | | Time | Range (%) | | Time | Range (%) | |
| (h) | Min | Max | (h) | Min | Max | (min) | Min | Max |
| 15 | 60 | 91 | 5 | 70 | 100 | | | |
| 24 | 80 | 100 | 6 | 80 | 100 | | | |

Figure 8:
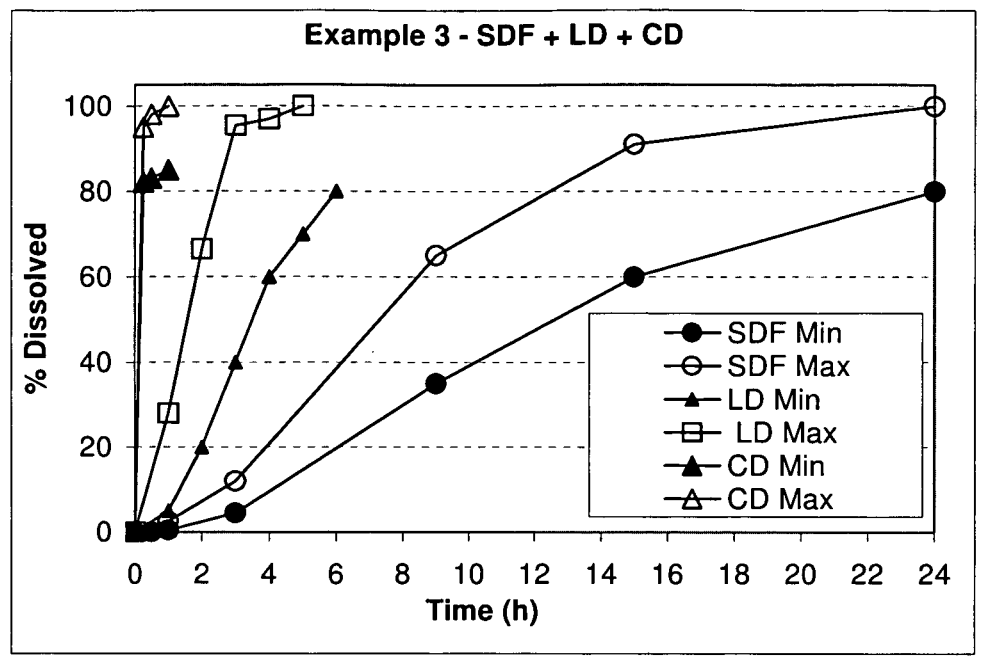
FIG. 8 depicts the expected release profiles of sildenafil (SDF), levodopa (LD) and carbidopa (CD) from the rupturing controlled release device according to Example 3.

FIG. 8 depicts the expected release profiles of sildenafil (SDF), levodopa (LD) and carbidopa (CD) from the rupturing controlled release device according to this example.

EXAMPLE 4

The following procedure was used to prepare osmotic device tablets containing nifedipine 60 mg strength in the core. The osmotic device tablets contained the following ingredients in the amounts indicated:

| | AMOUNT (mg) | | | |
|---|---|---|---|---|
| | Nifedipine Strength⇒ | | | |
| INGREDIENT | 60.0 | 60.0 | 60.0 | 60.0 |
| CORE | | | | |
| Nifedipine | 66.00 | 66.00 | 66.00 | 66.00 |
| Polysorbate 20 (Surfactant) | 0.20-5.00 | 0.20-5.00 | 0.20-5.00 | 0.20-5.00 |
| Microcrystalline cellulose PH 101 (Diluent) | 40.00-180.00 | 40.00-180.00 | 40.00-180.00 | 40.00-180.00 |
| Sodium chloride (Osmagent) | 90.00-425.00 | 90.00-425.00 | 90.00-425.00 | 90.00-425.00 |
| Povidone K30 (Binder) | 20.00-100.00 | 20.00-100.00 | 20.00-100.00 | 20.00-100.00 |
| Polyethylene oxide WSR 205 (Osmopolymer 1) | 70.00-230.00 | 70.00-230.00 | 70.00-230.00 | 70.00-230.00 |
| HPMC K4M (Osmopolymer 2) | 6.00-21.00 | 6.00-21.00 | 6.00-21.00 | 6.00-21.00 |
| Colloidal silicon dioxide (Glidant) | 0.20-12.00 | 0.20-12.00 | 0.20-12.00 | 0.20-12.00 |
| Magnesium stearate (Lubricant) | 0.20-12.00 | 0.20-12.00 | 0.20-12.00 | 0.20-12.00 |
| Purified water* | 40.00-100.00 | 40.00-100.00 | 40.00-100.00 | 40.00-100.00 |
| SUBCOAT | | | | |
| Opadry YS I 7006 | — | 2.00-5.00 | 5.00-10.00 | 10.00-15.00 |
| Purified water* | — | 20.00-50.00 | 50.00-100.00 | 100.00-150.00 |
| COATING A | | | | |
| Cellulose acetate 320-S (Water insoluble polymer) | 20.00-45.00 | 20.00-45.00 | 20.00-45.00 | 20.00-45.00 |
| Cellulose acetate 398-10 (Water insoluble polymer) | 19.50-35.00 | 19.50-35.00 | 19.50-35.00 | 19.50-35.00 |
| Polyethylene glycol 400 (Plasticizer) | 0.50-5.00 | 0.50-5.00 | 0.50-5.00 | 0.50-5.00 |
| Acetone* (organic solvent) | 500.00-1650.00 | 500.00-1650.00 | 500.00-1650.00 | 500.00-1650.00 |
| Purified water* | 89.00-370.00 | 89.00-370.00 | 89.00-370.00 | 89.00-370.00 |
| COATING B | | | | |
| Opadry Y 30 18084-A | 7.90-48.80 | 7.90-48.80 | 7.90-48.80 | 7.90-48.80 |
| Colorant | 0.10-1.20 | 0.10-1.20 | 0.10-1.20 | 0.10-1.20 |
| Purified water* | 128.00-530.00 | 128.00-530.00 | 128.00-530.00 | 128.00-530.00 |

*denotes a component used during manufacture of the osmotic device but which is substantially absent in the final dosage form.

First, the core composition was prepared by placing nifedipine, two osmopolymers, a diluent, an osmagent, and a binder in a high shear mixer and mix for 5 minutes. The granulation process was initiated by the gradual addition of a granulating solution containing a surfactant and purified water to the high shear with continuous blending to produce a wet blend. Next, the wet blend was granulated and dried at 40-50° C. for 20 minutes in a fluid bed to remove the water. Then, the dry granules were screened through a 30 USP mesh screen for size reduction. Next, the screened granules were mixed with a glidant and a lubricant, that have been previously passed through a 60 mesh screen, in a V-Blender during 5 minutes. This final blend was tabletted to provide the cores.

A subcoat comprising Opadry in purified water was applied onto the drug-containing cores to obtain cores surrounded by the subcoat.

A semipermeable composition was prepared as follows: two cellulose esters and a plasticizer were added to organic solvent and purified water, and mixed thoroughly to form a polymer solution. This solution was sprayed onto the tablets in a perforated pan coater to form film-coated tablets. A 0.5 mm hole was drilled through the coating to provide perforated film-coated tablets.

A finish coat comprising Opadry and a colorant in purified water was applied onto the film-coated tablets to obtain the osmotic device tablets.

The tablets were subjected to dissolution assays as described herein. The in vitro testing was performed with USP Type 7 apparatus, in 50 ml of water, at 37° C. during 24 hours. The samples were tested by UV spectrophotometry. The amount of nifedipine released and the extent of the rupture at the indicated time points is summarized below. The data details the amount of nifedipine released and the extent of the rupture at the indicated time points.

The release profiles obtained for twelve tablets (#1-#12) of the nifedipine formulation without subcoat are summarized below.

| Time (h) | Amount Released (%) | | | | | |
|---|---|---|---|---|---|---|
| | #1 | #2 | #3 | #4 | #5 | #6 |
| 0 | 0.0 | 0.0 | 0.0 | 0.0 | 0.0 | 0.0 |
| 2 | 7.6 | 10.1 | 8.5 | 9.0 | 9.3 | 7.5 |
| 4 | 18.0 | 23.3 | 20.2 | 19.6 | 27.1 | 19.9 |
| 8 | 49.9 | 53.1 | 57.1 | 52.9 | 55.1 | 45.3 |
| 10 | 59.1 | 66.8 | 70.0 | 72.1 | 60.3 | 55.0 |
| 12 | 69.3 | 72.6 | 79.4 | 84.0 | 70.0 | 62.8 |
| 24 | 86.5 | 85.7 | 87.0 | 89.5 | 84.0 | 85.0 |
| Size of rupture at 24 h | L | L | L | L | L | L |

| Time (h) | Amount Released (%) | | | | | |
|---|---|---|---|---|---|---|
| | #7 | #8 | #9 | #10 | #11 | #12 |
| 0 | 0.0 | 0.0 | 0.0 | 0.0 | 0.0 | 0.0 |
| 2 | 8.9 | 8.9 | 10.0 | 11.0 | 8.6 | 10.6 |
| 4 | 23.6 | 17.8 | 25.4 | 23.2 | 20.1 | 18.6 |
| 8 | 49.7 | 45.1 | 52.1 | 63.0 | 46.9 | 37.4 |
| 10 | 59.1 | 58.2 | 59.0 | 71.6 | 63.6 | 44.6 |
| 12 | 71.5 | 68.5 | 70.0 | 85.0 | 79.7 | 56.8 |
| 24 | 88.0 | 83.2 | 83.3 | 85.7 | 86.9 | 81.3 |
| Size of rupture at 24 h | L | L | L | L | L | M |

TABLE A

| Time (h) | Average Amount Released (%) | SD (n = 12) |
|---|---|---|
| 0 | 0.0 | |
| 2 | 9.2 | 1.1 |
| 4 | 21.4 | 3.0 |
| 8 | 50.6 | 6.6 |
| 10 | 61.6 | 7.8 |
| 12 | 72.5 | 8.4 |
| 24 | 85.5 | 2.3 |

The release profiles obtained for twelve tablets (#1-#12) of the nifedipine formulation with a 5 mg subcoat are disclosed in the table below.

| Time (h) | Amount Released (%) | | | | | |
|---|---|---|---|---|---|---|
| | #1 | #2 | #3 | #4 | #5 | #6 |
| 0 | 0.0 | 0.0 | 0.0 | 0.0 | 0.0 | 0.0 |
| 2 | 9.5 | 10.5 | 7.5 | 7.8 | 8.9 | 10.0 |
| 4 | 15.0 | 16.0 | 21.5 | 19.5 | 14.9 | 17.2 |
| 8 | 36.0 | 39.2 | 48.0 | 53.1 | 44.6 | 49.8 |
| 10 | 45.2 | 47.8 | 58.9 | 63.2 | 60.4 | 64.0 |
| 12 | 56.4 | 62.0 | 68.5 | 68.0 | 75.4 | 74.0 |
| 24 | 80.8 | 85.1 | 85.4 | 86.2 | 86.0 | 88.4 |
| Size of rupture at 24 h | M | L | L | L | M | L |

| Time (h) | Amount Released (%) | | | | | |
|---|---|---|---|---|---|---|
| | #7 | #8 | #9 | #10 | #11 | #12 |
| 0 | 0.0 | 0.0 | 0.0 | 0.0 | 0.0 | 0.0 |
| 2 | 9.5 | 10.5 | 7.5 | 7.8 | 8.9 | 10.0 |
| 4 | 15.0 | 16.0 | 18.0 | 19.5 | 14.9 | 19.5 |
| 8 | 39.4 | 38.2 | 48.0 | 49.2 | 42.6 | 43.0 |
| 10 | 54.8 | 49.2 | 56.9 | 59.8 | 63.5 | 56.9 |
| 12 | 70.3 | 65.3 | 65.1 | 68.0 | 78.0 | 61.8 |
| 24 | 80.8 | 85.1 | 85.4 | 86.2 | 86.0 | 89.0 |
| Size of rupture at 24 h | L | L | L | L | L | L |

TABLE B

| Time (h) | Average Amount Released (%) | SD (n = 12) |
|---|---|---|
| 0 | 0.0 | |
| 2 | 9.0 | 1.1 |
| 4 | 17.3 | 2.3 |
| 8 | 44.3 | 5.4 |
| 10 | 56.7 | 6.3 |
| 12 | 67.7 | 6.2 |
| 24 | 85.4 | 2.5 |

The release profiles obtained for twelve tablets (#1-#12) of the nifedipine formulation with a 10 mg subcoat are disclosed in the table below.

| Time (h) | Amount Released (%) | | | | | |
|---|---|---|---|---|---|---|
| | #1 | #2 | #3 | #4 | #5 | #6 |
| 0 | 0.0 | 0.0 | 0.0 | 0.0 | 0.0 | 0.0 |
| 2 | 5.0 | 3.8 | 3.9 | 4.0 | 4.9 | 7.0 |
| 4 | 17.5 | 12.8 | 9.5 | 9.0 | 15.5 | 12.5 |
| 8 | 35.9 | 32.8 | 41.0 | 41.6 | 37.1 | 32.2 |
| 10 | 50.0 | 44.0 | 53.3 | 56.9 | 48.0 | 45.3 |
| 12 | 61.8 | 52.4 | 63.2 | 66.9 | 62.6 | 58.2 |
| 24 | 86.4 | 81.3 | 83.0 | 81.5 | 84.8 | 86.0 |

-continued

| Size of Rupture at 24 h | S | M | S | S | S | M |
|---|---|---|---|---|---|---|
| Time | Amount Released (%) | | | | | |
| (h) | #7 | #8 | #9 | #10 | #11 | #12 |
| 0 | 0.0 | 0.0 | 0.0 | 0.0 | 0.0 | 0.0 |
| 2 | 5.2 | 4.0 | 3.5 | 3.9 | 4.0 | 8.0 |
| 4 | 13.8 | 13.0 | 13.1 | 12.9 | 14.8 | 11.8 |
| 8 | 38.3 | 32.5 | 36.2 | 37.3 | 43.5 | 30.6 |
| 10 | 50.2 | 44.4 | 50.9 | 47.7 | 54.6 | 43.5 |
| 12 | 58.0 | 52.3 | 60.9 | 59.2 | 62.9 | 54.3 |
| 24 | 87.3 | 82.7 | 85.0 | 82.4 | 88.0 | 86.7 |
| Size of rupture at 24 h | L | S | S | S | M | M |

TABLE C

| Time (h) | Average Amount Released (%) | SD (n = 12) |
|---|---|---|
| 0 | 0.0 | |
| 2 | 4.8 | 1.4 |
| 4 | 13.0 | 2.3 |
| 8 | 36.6 | 4.1 |
| 10 | 49.1 | 4.4 |
| 12 | 59.4 | 4.6 |
| 24 | 84.6 | 2.3 |

The release profiles obtained for twelve tablets (#1-#12) of the nifedipine formulation with a 15 mg subcoat are disclosed in the table below.

| Time | Amount Released (%) | | | | | |
|---|---|---|---|---|---|---|
| (h) | #1 | #2 | #3 | #4 | #5 | #6 |
| 0 | 0.0 | 0.0 | 0.0 | 0.0 | 0.0 | 0.0 |
| 2 | 5.2 | 4.0 | 2.5 | 2.9 | 3.9 | 3.6 |
| 4 | 11.0 | 9.1 | 9.3 | 8.8 | 8.9 | 10.0 |
| 8 | 30.4 | 29.5 | 27.1 | 34.1 | 24.0 | 30.6 |
| 10 | 41.1 | 40.2 | 38.6 | 41.3 | 35.4 | 40.7 |
| 12 | 54.0 | 50.5 | 53.3 | 51.6 | 45.7 | 49.4 |
| 24 | 84.0 | 82.9 | 88.2 | 84.6 | 85.0 | 86.7 |
| Size of rupture at 24 h | S | S | S | S | S | M |

| Time | Amount Released (%) | | | | | |
|---|---|---|---|---|---|---|
| (h) | #7 | #8 | #9 | #10 | #11 | #12 |
| 0 | 0.0 | 0.0 | 0.0 | 0.0 | 0.0 | 0.0 |
| 2 | 5.2 | 4.0 | 3.5 | 3.9 | 4.0 | 8.0 |
| 4 | 13.8 | 13.0 | 13.1 | 14.0 | 14.8 | 16.4 |
| 8 | 29.5 | 27.5 | 29.0 | 29.6 | 27.0 | 25.3 |
| 10 | 37.7 | 39.9 | 41.7 | 40.0 | 33.2 | 34.0 |
| 12 | 51.0 | 49.2 | 49.6 | 50.0 | 44.5 | 48.5 |
| 24 | 83.9 | 84.9 | 83.4 | 81.6 | 81.6 | 82.0 |
| Size of rupture at 24 h | S | S | S | M | S | S |

TABLE D

| Time (h) | Average Amount Released (%) | SD (n = 12) |
|---|---|---|
| 0 | 0.0 | |
| 2 | 4.2 | 1.4 |
| 4 | 11.8 | 2.6 |
| 8 | 28.6 | 2.7 |
| 10 | 38.7 | 2.9 |
| 12 | 49.8 | 2.7 |
| 24 | 84.1 | 2.0 |

The frequency of formation of small and large ruptures obtained for twelve tablets (#1-#12) of the nifedipine formulation with different weights of subcoat is disclosed in the table below.

| Weight of subcoat (mg) | Frequency of small and large ruptures | |
|---|---|---|
| | Small | Large |
| 0 | 0.00 | 0.92 |
| 5 | 0.00 | 0.83 |
| 10 | 0.58 | 0.08 |
| 15 | 0.92 | 0.00 |

EXAMPLE 5

The following procedure was used to prepare osmotic device tablets containing carvedilol 80 mg strength in the core. The osmotic device tablets contained the following ingredients in the amounts indicated:

| | AMOUNT (mg) Carvedilol Strength⇒ | | | |
|---|---|---|---|---|
| INGREDIENT | 80.00 | 80.00 | 80.00 | 80.00 |
| CORE | | | | |
| Carvedilol phosphate ethanolate | 82.40 | 82.40 | 82.40 | 82.40 |
| Polysorbate 80 (Surfactant) | 0.27-7.00 | 0.27-7.00 | 0.27-7.00 | 0.27-7.00 |
| Microcrystalline cellulose PH 200 (Diluent) | 55.00-250.00 | 55.00-250.00 | 55.00-250.00 | 55.00-250.00 |
| Mannitol (Osmagent) | 124.00-584.00 | 124.00-584.00 | 124.00-584.00 | 124.00-584.00 |
| Povidone K90 (Binder) | 27.00-140.00 | 27.00-140.00 | 27.00-140.00 | 27.00-140.00 |
| Polyethylene oxide WSR 205 (Osmopolymer 1) | 95.00-316.00 | 95.00-316.00 | 95.00-316.00 | 95.00-316.00 |

-continued

| INGREDIENT | AMOUNT (mg) Carvedilol Strength→ | | | |
|---|---|---|---|---|
| | 80.00 | 80.00 | 80.00 | 80.00 |
| HPMC K4M (Osmopolymer 2) | 8.00-30.00 | 8.00-30.00 | 8.00-30.00 | 8.00-30.00 |
| Colloidal silicon dioxide (Glidant) | 0.25-17.00 | 0.25-17.00 | 0.25-17.00 | 0.25-17.00 |
| Magnesium stearate (Lubricant) | 0.25-17.00 | 0.25-17.00 | 0.25-17.00 | 0.25-17.00 |
| Purified water* | 55.00-140.00 | 55.00-140.00 | 55.00-140.00 | 55.00-140.00 |
| SUBCOAT | | | | |
| Opadry YS I 7006 | — | 2.00-6.00 | 5.00-12.00 | 10.00-17.00 |
| Purified water* | — | 20.00-60.00 | 50.00-120.00 | 100.00-170.00 |
| COATING A | | | | |
| Cellulose acetate 320-S (Water insoluble polymer) | 20.00-45.00 | 20.00-45.00 | 20.00-45.00 | 20.00-45.00 |
| Cellulose acetate 398-10 (Water insoluble polymer) | 19.50-35.00 | 19.50-35.00 | 19.50-35.00 | 19.50-35.00 |
| Polyethylene glycol 400 (Plasticizer) | 0.50-5.00 | 0.50-5.00 | 0.50-5.00 | 0.50-5.00 |
| Acetone* (organic solvent) | 500.00-1650.00 | 500.00-1650.00 | 500.00-1650.00 | 500.00-1650.00 |
| Purified water* | 89.00-370.00 | 89.00-370.00 | 89.00-370.00 | 89.00-370.00 |
| COATING B | | | | |
| Opadry Y 30 18084-A | 10.00-60.00 | 10.00-60.00 | 10.00-60.00 | 10.00-60.00 |
| Colorant | 0.50-1.20 | 0.50-1.20 | 0.50-1.20 | 0.50-1.20 |
| Purified water* | 150.00-550.00 | 150.00-550.00 | 150.00-550.00 | 150.00-550.00 |

*denotes a component used during manufacture of the osmotic device but which is substantially absent in the final dosage form.

First, the core composition was prepared by placing carvedilol phosphate ethanolate, two osmopolymers, a diluent, an osmagent, and a binder in a high shear mixer and mix for 5 minutes. The granulation process was initiated by the gradual addition of a granulating solution containing a surfactant and purified water to the high shear with continuous blending to produce a wet blend. Next, the wet blend was granulated and dried at 40-50° C. for 20 minutes in a fluid bed to remove the water. Then, the dry granules were screened through a 30 USP mesh screen for size reduction. Next, the screened granules were mixed with a glidant and a lubricant, that have been previously passed through a 60 mesh screen, in a V-Blender during 5 minutes. This final blend was tabletted to provide the cores.

A subcoat comprising Opadry in purified water was applied onto the drug-containing cores to obtain cores surrounded by the subcoat.

A semipermeable composition was prepared as follows: two cellulose esters and a plasticizer were added to organic solvent and purified water, and mixed thoroughly to form a polymer solution. This solution was sprayed onto the tablets in a perforated pan coater to form film-coated tablets. A 0.5 mm hole was drilled through the coating to provide perforated film-coated tablets.

A finish coat comprising Opadry and a colorant in purified water was applied onto the film-coated tablets to obtain the osmotic device tablets.

The tablets were subjected to dissolution assays as described herein. The in vitro testing was performed with USP Type 2, in 900 ml of 0.01 N HCl, at 37° C. during 24 hours. The samples were tested by RP-HPLC. The amount of carvedilol released and the extent of the rupture at the indicated time points is summarized below. The data details the amount of carvedilol released and the extent of the rupture at the indicated time points.

The release profiles obtained for twelve tablets (#1-#12) of the carvedilol formulation without subcoat are disclosed in the table below.

| Time (h) | Amount Released (%) | | | | | |
|---|---|---|---|---|---|---|
| | #1 | #2 | #3 | #4 | #5 | #6 |
| 0 | 0.0 | 0.0 | 0.0 | 0.0 | 0.0 | 0.0 |
| 0.5 | 9.9 | 8.9 | 7.6 | 10.1 | 10.9 | 8.5 |
| 1 | 10.7 | 14.5 | 10.6 | 14.1 | 14.3 | 13.7 |
| 2 | 40.9 | 30.6 | 18.5 | 30.4 | 29.5 | 29.4 |
| 4 | 92.0 | 74.7 | 72.6 | 64.2 | 54.1 | 72.0 |
| 8 | 98.6 | 97.0 | 96.0 | 81.5 | 95.1 | 95.2 |
| 12 | 99.5 | 97.4 | 99.1 | 93.2 | 97.9 | 97.1 |
| 24 | 101.3 | 99.4 | 100.9 | 101.3 | 98.9 | 99.1 |
| Size of rupture at 24 h | L | M | M | L | L | L |

| Time (h) | Amount Released (%) | | | | | |
|---|---|---|---|---|---|---|
| | #7 | #8 | #9 | #10 | #11 | #12 |
| 0 | 0.0 | 0.0 | 0.0 | 0.0 | 0.0 | 0.0 |
| 0.5 | 7.7 | 9.1 | 9.8 | 8.6 | 10.8 | 8.6 |
| 1 | 18.5 | 18.6 | 14.0 | 14.3 | 14.4 | 13.7 |
| 2 | 41.0 | 30.7 | 18.6 | 31.0 | 29.3 | 29.5 |
| 4 | 54.3 | 73.0 | 91.9 | 73.0 | 71.6 | 73.0 |
| 8 | 94.5 | 94.7 | 97.0 | 81.4 | 98.5 | 94.3 |
| 12 | 97.3 | 99.4 | 98.6 | 93.3 | 97.2 | 99.4 |
| 24 | 98.7 | 100.6 | 98.9 | 98.9 | 99.8 | 99.1 |
| Size of Rupture at 24 h | L | L | M | L | L | L |

TABLE E

| Time (h) | Average Amount Released (%) | SD (n = 12) |
|---|---|---|
| 0 | 0.0 | |
| 0.5 | 9.2 | 1.1 |
| 1 | 14.3 | 2.4 |
| 2 | 30.0 | 6.8 |
| 4 | 72.2 | 11.7 |
| 8 | 93.7 | 5.9 |

TABLE E-continued

| Time (h) | Average Amount Released (%) | SD (n = 12) |
|---|---|---|
| 12 | 97.4 | 2.2 |
| 24 | 99.7 | 1.0 |

The release profiles obtained for twelve tablets (#1-#12) of the carvedilol formulation with a 5 mg subcoat are disclosed in the table below.

| Time (h) | Amount Released (%) | | | | | |
|---|---|---|---|---|---|---|
|  | #1 | #2 | #3 | #4 | #5 | #6 |
| 0 | 0.0 | 0.0 | 0.0 | 0.0 | 0.0 | 0.0 |
| 0.5 | 9.5 | 5.1 | 10.5 | 11.7 | 8.6 | 10.1 |
| 1 | 14.8 | 10.3 | 17.2 | 15.0 | 15.1 | 15.1 |
| 2 | 27.6 | 15.7 | 24.3 | 22.9 | 28.2 | 22.7 |
| 4 | 61.5 | 72.1 | 60.4 | 68.9 | 65.4 | 51.1 |
| 8 | 91.4 | 91.6 | 92.7 | 98.0 | 93.8 | 83.8 |
| 12 | 96.7 | 96.0 | 99.3 | 100.4 | 98.7 | 96.3 |
| 24 | 102.0 | 101.7 | 101.6 | 102.9 | 102.4 | 99.0 |
| Size of rupture at 24 h | L | L | L | M | L | L |

| Time (h) | Amount Released (%) | | | | | |
|---|---|---|---|---|---|---|
|  | #7 | #8 | #9 | #10 | #11 | #12 |
| 0 | 0.0 | 0.0 | 0.0 | 0.0 | 0.0 | 0.0 |
| 0.5 | 9.6 | 5.6 | 9.5 | 11.5 | 9.1 | 10.0 |
| 1 | 14.9 | 10.4 | 15.4 | 16.9 | 15.7 | 14.7 |
| 2 | 27.5 | 15.6 | 18.6 | 28.2 | 25.9 | 25.6 |
| 4 | 65.3 | 55.2 | 64.8 | 51.0 | 74.1 | 61.4 |
| 8 | 84.2 | 91.4 | 92.0 | 98.1 | 92.6 | 93.4 |
| 12 | 99.2 | 98.7 | 96.1 | 100.2 | 96.2 | 97.5 |
| 24 | 102.0 | 101.7 | 101.8 | 102.8 | 98.9 | 102.5 |
| Size of rupture at 24 h | L | L | M | M | M | L |

TABLE F

| Time (h) | Average Amount Released (%) | SD (n = 12) |
|---|---|---|
| 0 | 0.0 |  |
| 0.5 | 9.2 | 2.0 |
| 1 | 14.6 | 2.2 |
| 2 | 23.6 | 4.6 |
| 4 | 62.6 | 7.5 |
| 8 | 91.9 | 4.3 |
| 12 | 97.9 | 1.7 |
| 24 | 101.6 | 1.3 |

The release profiles obtained for twelve tablets (#1-#12) of the carvedilol formulation with a 10 mg subcoat are disclosed in the table below.

| Time (h) | Amount Released (%) | | | | | |
|---|---|---|---|---|---|---|
|  | #1 | #2 | #3 | #4 | #5 | #6 |
| 0 | 0.0 | 0.0 | 0.0 | 0.0 | 0.0 | 0.0 |
| 0.5 | 5.6 | 10.1 | 7.5 | 7.9 | 7.8 | 7.1 |
| 1 | 11.9 | 16.1 | 13.6 | 10.2 | 13.3 | 11.4 |
| 2 | 16.0 | 25.7 | 21.6 | 20.3 | 20.9 | 20.2 |
| 4 | 48.5 | 50.9 | 61.6 | 54.6 | 54.0 | 56.9 |
| 8 | 85.0 | 84.4 | 87.4 | 83.0 | 80.2 | 84.6 |
| 12 | 98.0 | 96.3 | 96.8 | 97.1 | 93.7 | 95.1 |
| 24 | 99.3 | 102.9 | 100.0 | 98.9 | 97.5 | 100.4 |
| Size of rupture at 24 h | M | S | M | M | S | M |

| Time (h) | Amount Released (%) | | | | | |
|---|---|---|---|---|---|---|
|  | #7 | #8 | #9 | #10 | #11 | #12 |
| 0 | 0.0 | 0.0 | 0.0 | 0.0 | 0.0 | 0.0 |
| 0.5 | 6.0 | 9.1 | 7.8 | 7.9 | 7.5 | 6.9 |
| 1 | 12.4 | 16.3 | 12.1 | 9.9 | 12.8 | 12.1 |
| 2 | 25.4 | 20.6 | 16.8 | 19.2 | 18.9 | 24.0 |
| 4 | 52.5 | 48.6 | 59.6 | 48.9 | 57.8 | 61.0 |
| 8 | 85.5 | 87.9 | 84.1 | 81.2 | 84.9 | 86.4 |
| 12 | 94.9 | 94.0 | 99.1 | 97.1 | 96.0 | 96.1 |
| 24 | 103.1 | 99.2 | 100.4 | 99.9 | 97.4 | 98.6 |
| Size of rupture at 24 h | M | S | M | S | M | S |

TABLE G

| Time (h) | Average Amount Released (%) | SD (n = 12) |
|---|---|---|
| 0 | 0.0 |  |
| 0.5 | 7.6 | 1.2 |
| 1 | 12.7 | 2.0 |
| 2 | 20.8 | 3.0 |
| 4 | 54.6 | 4.8 |
| 8 | 84.6 | 2.3 |
| 12 | 96.2 | 1.6 |
| 24 | 99.8 | 1.8 |

The release profiles obtained for twelve tablets (#1-#12) of the carvedilol formulation with a 15 mg subcoat are disclosed in the table below.

| Time (h) | Amount Released (%) | | | | | |
|---|---|---|---|---|---|---|
|  | #1 | #2 | #3 | #4 | #5 | #6 |
| 0 | 0.0 | 0.0 | 0.0 | 0.0 | 0.0 | 0.0 |
| 0.5 | 7.2 | 1.1 | 5.5 | 2.2 | 4.2 | 4.8 |
| 1 | 5.2 | 11.6 | 8.5 | 9.8 | 13.8 | 8.3 |
| 2 | 19.0 | 17.8 | 16.4 | 17.9 | 18.9 | 16.5 |
| 4 | 51.1 | 46.1 | 51.6 | 46.2 | 46.5 | 50.2 |
| 8 | 79.7 | 76.9 | 80.4 | 81.0 | 83.4 | 77.5 |
| 12 | 96.0 | 91.7 | 93.8 | 93.6 | 95.1 | 95.1 |
| 24 | 100.3 | 96.7 | 97.0 | 99.6 | 99.4 | 99.9 |
| Size of rupture at 24 h | S | M | S | S | S | S |

| Time (h) | Amount Released (%) | | | | | |
|---|---|---|---|---|---|---|
|  | #7 | #8 | #9 | #10 | #11 | #12 |
| 0 | 0.0 | 0.0 | 0.0 | 0.0 | 0.0 | 0.0 |
| 0.5 | 7.0 | 2.5 | 5.4 | 3.2 | 3.8 | 4.5 |
| 1 | 13.4 | 5.7 | 12.0 | 7.9 | 8.1 | 11.4 |
| 2 | 15.0 | 20.7 | 18.6 | 17.3 | 17.9 | 17.2 |
| 4 | 51.4 | 51.2 | 46.3 | 47.3 | 50.9 | 46.2 |
| 8 | 77.2 | 79.7 | 83.0 | 81.8 | 77.7 | 79.8 |
| 12 | 92.0 | 93.2 | 95.8 | 95.6 | 94.9 | 94.0 |
| 24 | 97.5 | 99.9 | 99.8 | 98.7 | 100.4 | 96.0 |
| Size of rupture at 24 h | S | M | S | S | S | S |

TABLE H

| Time (h) | Average Amount Released (%) | SD (n = 12) |
|---|---|---|
| 0 | 0.0 |  |
| 0.5 | 4.3 | 1.9 |
| 1 | 9.6 | 2.8 |
| 2 | 17.8 | 1.5 |
| 4 | 48.7 | 2.5 |
| 8 | 79.8 | 2.2 |

TABLE H-continued

| Time (h) | Average Amount Released (%) | SD (n = 12) |
|---|---|---|
| 12 | 94.2 | 1.4 |
| 24 | 98.7 | 1.3 |

The frequency of formation of small and large ruptures obtained for twelve tablets (#1-#12) of the carvedilol formulation with different weights of subcoat is disclosed in the table below.

| Weight of subcoat (mg) | Frequency of small and large ruptures | |
|---|---|---|
| | Small | Large |
| 0 | 0.00 | 0.75 |
| 5 | 0.00 | 0.67 |
| 10 | 0.42 | 0.00 |
| 15 | 0.83 | 0.00 |

EXAMPLE 6

The following procedure was used to prepare osmotic device tablets containing carbamazepine 200 mg strength in the core. The osmotic device tablets contained the following ingredients in the amounts indicated:

| INGREDIENT | AMOUNT (mg) Carbamazepine Strength⇒ | | | |
|---|---|---|---|---|
| | 200.00 | 200.00 | 200.00 | 200.00 |
| CORE | | | | |
| Carbamazepine | 200.00 | 200.00 | 200.00 | 200.00 |
| Polysorbate 80 (Surfactant) | 0.70-17.00 | 0.70-17.00 | 0.70-17.00 | 0.70-17.00 |
| Microcrystalline cellulose PH 200 (Diluent) | 130.00-600.00 | 130.00-600.00 | 130.00-600.00 | 130.00-600.00 |
| Mannitol (Osmagent) | 300.00-900.00 | 300.00-900.00 | 300.00-900.00 | 300.00-900.00 |
| Povidone K90 (Binder) | 66.00-340.00 | 66.00-340.00 | 66.00-340.00 | 66.00-340.00 |
| Polyethylene oxide WSR 205 (Osmopolymer 1) | 230.00-780.00 | 230.00-780.00 | 230.00-780.00 | 230.00-780.00 |
| HPMC K4M (Osmopolymer 2) | 20.00-75.00 | 20.00-75.00 | 20.00-75.00 | 20.00-75.00 |
| Colloidal silicon dioxide (Glidant) | 0.60-41.00 | 0.60-41.00 | 0.60-41.00 | 0.60-41.00 |
| Magnesium stearate (Lubricant) | 0.60-41.00 | 0.60-41.00 | 0.60-41.00 | 0.60-41.00 |
| Purified water* | 130.00-340.00 | 130.00-340.00 | 130.00-340.00 | 130.00-340.00 |
| SUBCOAT | | | | |
| Opadry YS I 7006 | — | 5.00-10.00 | 10.00-15.00 | 15.00-20.00 |
| Purified water* | — | 50.00-100.00 | 100.00-150.00 | 150.00-200.00 |
| COATING A | | | | |
| Cellulose acetate 320-S (Water insoluble polymer) | 20.00-45.00 | 20.00-45.00 | 20.00-45.00 | 20.00-45.00 |
| Cellulose acetate 398-10 (Water insoluble polymer) | 19.50-35.00 | 19.50-35.00 | 19.50-35.00 | 19.50-35.00 |
| Polyethylene glycol 400 (Plasticizer) | 0.50-5.00 | 0.50-5.00 | 0.50-5.00 | 0.50-5.00 |
| Acetone* (organic solvent) | 500.00-1650.00 | 500.00-1650.00 | 500.00-1650.00 | 500.00-1650.00 |
| Purified water* | 89.00-370.00 | 89.00-370.00 | 89.00-370.00 | 89.00-370.00 |
| COATING B | | | | |
| Opadry Y 30 18084-A | 10.00-60.00 | 10.00-60.00 | 10.00-60.00 | 10.00-60.00 |
| Colorant | 0.50-1.20 | 0.50-1.20 | 0.50-1.20 | 0.50-1.20 |
| Purified water* | 150.00-550.00 | 150.00-550.00 | 150.00-550.00 | 150.00-550.00 |

*denotes a component used during manufacture of the osmotic device but which is substantially absent in the final dosage form.

First, the core composition was prepared by placing carbamazepine, two osmopolymers, a diluent, an osmagent, and a binder in a high shear mixer and mix for 5 minutes. The granulation process was initiated by the gradual addition of a granulating solution containing a surfactant and purified water to the high shear with continuous blending to produce a wet blend. Next, the wet blend was granulated and dried at 40-50° C. for 20 minutes in a fluid bed to remove the water. Then, the dry granules were screened through a 30 USP mesh screen for size reduction. Next, the screened granules were mixed with a glidant and a lubricant, that have been previously passed through a 60 mesh screen, in a V-Blender during 5 minutes. This final blend was tabletted to provide the cores.

A subcoat comprising Opadry in purified water was applied onto the drug-containing cores to obtain cores surrounded by the subcoat.

A semipermeable composition was prepared as follows: two cellulose esters and a plasticizer were added to organic solvent and purified water, and mixed thoroughly to form a polymer solution. This solution was sprayed onto the tablets in a perforated pan coater to form film-coated tablets. A 0.5 mm hole was drilled through the coating to provide perforated film-coated tablets.

A finish coat comprising Opadry and a colorant in purified water was applied onto the film-coated tablets to obtain the osmotic device tablets.

The tablets were subjected to dissolution assays as described herein. The in vitro testing was performed with USP Type 2 apparatus, in 900 ml of sodium lauryl sufate 1%, at 37° C. during 24 hours. The samples were tested by UV spectrophotometry. The amount of carbamazepine released and the extent of the rupture at the indicated time points is summarized below. The data details the amount of carbamazepine released and the extent of the rupture at the indicated time points.

The release profiles obtained for twelve tablets (#1-#12) of the carbamazepine formulation without subcoat are disclosed in the table below.

| Time | Amount Released (%) | | | | | |
|---|---|---|---|---|---|---|
| (h) | #1 | #2 | #3 | #4 | #5 | #6 |
| 0 | 0.0 | 0.0 | 0.0 | 0.0 | 0.0 | 0.0 |
| 2 | 1.4 | 1.0 | 1.8 | 2.3 | 1.7 | 1.8 |
| 4 | 21.4 | 21.1 | 27.5 | 15.9 | 21.9 | 24.3 |
| 8 | 56.0 | 44.0 | 58.4 | 51.0 | 70.1 | 63.0 |
| 10 | 72.3 | 63.0 | 77.7 | 75.0 | 80.7 | 76.5 |
| 12 | 77.5 | 74.1 | 84.5 | 77.9 | 80.7 | 84.8 |
| 16 | 81.8 | 83.7 | 86.1 | 80.0 | 81.1 | 85.9 |
| 24 | 84.6 | 84.6 | 89.7 | 84.6 | 85.5 | 89.9 |
| Size of Rupture at 24 h | L | L | L | L | L | L |

| Time | Amount Released (%) | | | | | |
|---|---|---|---|---|---|---|
| (h) | #7 | #8 | #9 | #10 | #11 | #12 |
| 0 | 0.0 | 0.0 | 0.0 | 0.0 | 0.0 | 0.0 |
| 2 | 1.3 | 0.9 | 1.8 | 2.2 | 2.0 | 1.9 |
| 4 | 21.3 | 20.9 | 22.1 | 15.8 | 27.6 | 24.0 |
| 8 | 63.0 | 58.1 | 71.4 | 45.2 | 66.3 | 62.1 |
| 10 | 77.6 | 71.1 | 80.1 | 63.1 | 77.6 | 76.4 |
| 12 | 79.5 | 84.1 | 81.2 | 74.5 | 79.9 | 85.9 |
| 16 | 81.8 | 84.5 | 82.1 | 81.2 | 80.3 | 86.2 |
| 24 | 84.7 | 85.0 | 85.8 | 84.5 | 88.9 | 89.8 |
| Size of Rupture at 24 h | M | L | L | L | L | L |

TABLE I

| Time (h) | Average Amount Released (%) | SD (n = 12) |
|---|---|---|
| 0 | 0.0 | |
| 2 | 1.7 | 0.4 |
| 4 | 22.0 | 3.7 |
| 8 | 59.0 | 8.9 |
| 10 | 74.3 | 5.9 |
| 12 | 80.4 | 3.9 |
| 16 | 82.9 | 2.3 |
| 24 | 86.5 | 2.3 |

The release profiles obtained for twelve tablets (#1-#12) of the carbamazepine formulation with a 5 mg subcoat are disclosed in the table below.

| Time | Amount Released (%) | | | | | |
|---|---|---|---|---|---|---|
| (h) | #1 | #2 | #3 | #4 | #5 | #6 |
| 0 | 0.0 | 0.0 | 0.0 | 0.0 | 0.0 | 0.0 |
| 2 | 0.7 | 1.1 | 0.6 | 1.2 | 0.9 | 0.6 |
| 4 | 22.7 | 16.3 | 25.4 | 19.9 | 20.0 | 18.4 |
| 8 | 49.0 | 53.0 | 38.5 | 54.6 | 40.9 | 47.6 |
| 10 | 59.1 | 66.7 | 57.1 | 66.7 | 64.1 | 61.6 |
| 12 | 82.0 | 75.5 | 75.5 | 80.7 | 74.9 | 74.1 |
| 16 | 83.8 | 83.6 | 80.2 | 84.5 | 84.3 | 86.4 |
| 24 | 86.1 | 85.3 | 85.9 | 90.0 | 85.5 | 89.9 |
| Size of Rupture at 24 h | M | L | M | L | M | L |

| Time | Amount Released (%) | | | | | |
|---|---|---|---|---|---|---|
| (h) | #7 | #8 | #9 | #10 | #11 | #12 |
| 0 | 0.0 | 0.0 | 0.0 | 0.0 | 0.0 | 0.0 |
| 2 | 1.3 | 0.5 | 0.7 | 0.8 | 0.3 | 1.5 |
| 4 | 16.5 | 22.5 | 18.8 | 20.2 | 25.3 | 20.5 |
| 8 | 52.5 | 45.1 | 49.1 | 43.0 | 38.1 | 55.0 |
| 10 | 66.5 | 58.5 | 61.9 | 63.7 | 56.2 | 67.0 |
| 12 | 76.1 | 82.0 | 74.7 | 74.7 | 75.0 | 81.1 |
| 16 | 83.8 | 83.2 | 84.5 | 83.7 | 79.6 | 84.6 |
| 24 | 85.8 | 85.8 | 90.3 | 85.1 | 85.8 | 90.2 |
| Size of Rupture at 24 h | M | L | L | L | L | L |

TABLE J

| Time (h) | Average Amount Released (%) | SD (n = 12) |
|---|---|---|
| 0 | 0.0 | |
| 2 | 0.9 | 0.4 |
| 4 | 20.5 | 3.0 |
| 8 | 47.2 | 6.1 |
| 10 | 62.4 | 4.0 |
| 12 | 77.2 | 3.2 |
| 16 | 83.5 | 1.9 |
| 24 | 87.1 | 2.2 |

The release profiles obtained for twelve tablets (#1-#12) of the carbamazepine formulation with a 10 mg subcoat are disclosed in the table below.

| Time | Amount Released (%) | | | | | |
|---|---|---|---|---|---|---|
| (h) | #1 | #2 | #3 | #4 | #5 | #6 |
| 0 | 0.0 | 0.0 | 0.0 | 0.0 | 0.0 | 0.0 |
| 2 | 4.5 | 2.7 | 4.1 | 2.3 | 3.9 | 2.1 |
| 4 | 14.2 | 9.9 | 15.2 | 16.2 | 19.9 | 20.2 |
| 8 | 42.6 | 38.6 | 39.8 | 40.3 | 46.1 | 32.3 |
| 10 | 53.1 | 52.9 | 57.8 | 58.1 | 52.2 | 59.2 |
| 12 | 66.5 | 66.8 | 66.6 | 71.0 | 67.2 | 71.4 |
| 16 | 79.9 | 78.4 | 76.9 | 75.2 | 77.1 | 80.8 |
| 24 | 82.9 | 82.7 | 87.6 | 81.7 | 86.8 | 84.1 |
| Size of Rupture at 24 h | S | S | M | M | M | M |

| Time | Amount Released (%) | | | | | |
|---|---|---|---|---|---|---|
| (h) | #7 | #8 | #9 | #10 | #11 | #12 |
| 0 | 0.0 | 0.0 | 0.0 | 0.0 | 0.0 | 0.0 |
| 2 | 4.7 | 1.9 | 2.5 | 3.8 | 3.1 | 2.7 |
| 4 | 14.6 | 8.6 | 16.9 | 16.7 | 15.0 | 20.1 |
| 8 | 43.0 | 39.0 | 40.1 | 46.0 | 39.5 | 32.5 |
| 10 | 52.1 | 55.9 | 58.6 | 52.1 | 54.9 | 59.3 |
| 12 | 66.6 | 66.8 | 71.5 | 67.0 | 66.8 | 71.5 |

-continued

| | | | | | | |
|---|---|---|---|---|---|---|
| 16 | 74.9 | 77.9 | 79.2 | 78.3 | 77.9 | 80.4 |
| 24 | 83.0 | 87.3 | 81.6 | 82.2 | 87.4 | 83.2 |
| Size of Rupture at 24 h | S | L | M | M | M | S |

TABLE K

| Time (h) | Average Amount Released (%) | SD (n = 12) |
|---|---|---|
| 0 | 0.0 | |
| 2 | 3.2 | 1.0 |
| 4 | 15.6 | 3.7 |
| 8 | 40.0 | 4.3 |
| 10 | 55.5 | 3.0 |
| 12 | 68.3 | 2.3 |
| 16 | 78.1 | 1.9 |
| 24 | 84.2 | 2.4 |

The release profiles obtained for twelve tablets (#1-#12) of the carbamazepine formulation with a 15 mg subcoat are disclosed in the table below.

| Time (h) | Amount Released (%) | | | | | |
|---|---|---|---|---|---|---|
| | #1 | #2 | #3 | #4 | #5 | #6 |
| 0 | 0.0 | 0.0 | 0.0 | 0.0 | 0.0 | 0.0 |
| 2 | 2.0 | 1.7 | 2.5 | 2.7 | 1.2 | 4.3 |
| 4 | 12.9 | 20.7 | 18.1 | 14.1 | 17.1 | 11.6 |
| 8 | 31.5 | 40.2 | 34.2 | 31.5 | 33.5 | 35.9 |
| 10 | 45.8 | 47.1 | 50.2 | 50.6 | 46.0 | 51.2 |
| 12 | 59.9 | 59.6 | 64.2 | 64.0 | 63.2 | 63.1 |
| 16 | 74.2 | 74.6 | 78.7 | 74.0 | 78.1 | 79.1 |
| 24 | 81.2 | 80.5 | 82.9 | 81.8 | 85.5 | 85.5 |
| Size of Rupture at 24 h | S | S | S | S | M | S |

| Time (h) | Amount Released (%) | | | | | |
|---|---|---|---|---|---|---|
| | #7 | #8 | #9 | #10 | #11 | #12 |
| 0 | 0.0 | 0.0 | 0.0 | 0.0 | 0.0 | 0.0 |
| 2 | 1.4 | 4.5 | 1.2 | 1.7 | 3.0 | 2.4 |
| 4 | 20.5 | 11.3 | 16.9 | 13.3 | 14.3 | 17.7 |
| 8 | 32.9 | 36.2 | 33.0 | 31.3 | 39.2 | 33.9 |
| 10 | 46.4 | 51.3 | 45.5 | 46.6 | 51.0 | 50.1 |
| 12 | 59.9 | 64.1 | 61.2 | 59.8 | 63.2 | 63.9 |
| 16 | 75.0 | 79.9 | 75.4 | 77.3 | 74.3 | 79.1 |
| 24 | 80.5 | 85.6 | 81.2 | 81.4 | 81.6 | 83.4 |
| Size of Rupture at 24 h | S | S | S | S | S | S |

TABLE L

| Time (h) | Average Amount Released (%) | SD (n = 12) |
|---|---|---|
| 0 | 0.0 | |
| 2 | 2.4 | 1.1 |
| 4 | 15.7 | 3.2 |
| 8 | 34.4 | 2.9 |
| 10 | 48.5 | 2.4 |
| 12 | 62.2 | 1.9 |
| 16 | 76.6 | 2.3 |
| 24 | 82.6 | 2.0 |

The frequency of formation of small and large ruptures obtained for twelve tablets (#1-#12) of the carbamazepine formulation with different weights of subcoat is disclosed in the table below.

| Weight of subcoat (mg) | Frequency of small and large ruptures | |
|---|---|---|
| | Small | Large |
| 0 | 0.00 | 0.92 |
| 5 | 0.00 | 0.67 |
| 10 | 0.33 | 0.08 |
| 15 | 0.92 | 0.00 |

EXAMPLE 7

The procedures herein were followed to prepare osmotic device tablets comprising a drug in the core, the specified excipients in the core, membranes having the specified weight as detailed in the table below. The tablets did not comprise respective subcoats. The tablets were then exposed to aqueous medium and the size and frequency of occurrence of ruptures in the membrane were determined visually.

| Drug | Composition | Membrane weight(mg) | Rupture (*) |
|---|---|---|---|
| Lercanidipine 30 mg (only 1 passageway) | NaCl 100 mg/PEO 205 75/PEO NK 60 25 mg/HPMC 100LV 1.4 mg/ HPMC K4M 4.3 mg | 33 | 6/6 (6 tablets out of 6 tablets) small rupture |
| | citric 7 mg/NaCl 100 mg/PEO 205 99.8/HPMC 100LV 4.3/ HPMC K4M 4.3 mg | 45 | 3/6 no rupture-3/6 small rupture |
| | citric 7 mg/NaCl 100 mg/PEO 205 99.8/HPMC 100LV 4.3/ HPMC K4M 4.3 mg | 68 | 3/6 no rupture-3/6 small rupture |
| | tartaric 15 mg/NaCl 101.5 mg/ PEO 205 68.2/HPMC K4M 5.7 mg | 50.03 | no rupture |
| | tartaric 10 mg/NaCl 101.5 mg/ PEO 205 68.2/HPMC K4M 5.7 mg | 48.76 | 1/4 small rupture-1/4 small rupture in the pass.-2/4 no rupture |
| | tartaric 5 mg/NaCl 101.5 mg/PEO 205 68.2/HPMC K4M 5.7 mg | 53 | 1/4 small rupture-1/4 small rupture in the pass.-2/4 no rupture |
| | citric 15 mg/NaCl 101.5 mg/PEO 205 68.2/HPMC K4M 5.7 mg | 49.95 | 2/4 small rupture-2/4 no rupture |
| | NaCl 101.5 mg/PEO 205 68.2 mg/ HPMC K4M 5.70 mg | 34.42 | 6/6 big rupture in the pass. |
| | NaCl 101.5 mg/PEO 205 68.2 mg/ HPMC K4M 5.70 mg | 41.13 | 6/6 big rupture in the pass. |

-continued

| Drug | Composition | Membrane weight(mg) | Rupture (*) |
|------|-------------|---------------------|-------------|
| | NaCl 101.5 mg/PEO 205 68.2 mg/ HPMC K4M 5.70 mg | 46.99 | 6/6 big rupture in the pass. |
| | NaCl 101.5 mg/PEO 205 68.2 mg/ HPMC K4M 5.70 mg | 50.36 | 6/6 big rupture in the pass. |
| | NaCl 101.5 mg/PEO 205 68.2 mg/ HPMC K4M 5.70 mg | 57.74 | 6/6 big rupture in the pass. |
| | NaCl 51 mg/PEO 205 68.2 mg/ HPMC K4M 5.70 mg | 49.64 | 6/6 big rupture in the pass. |
| | citric 7 mg/NaCl 101.5 mg/PEO 205 68 mg/HPMC K4M 5.7 mg | 29.6 | 2/4 small rupture-2/4 no rupture |
| | citric 7 mg/NaCl 101.5 mg/PEO 205 68 mg/HPMC K4M 5.7 mg | 35.3 | 2/4 small rupture-2/4 no rupture |
| | citric 15 mg/NaCl 100 mg/PEO 205 68 mg/HPMC K4M 5.7 mg | 35.9 | 1/6 small rupture-5/6 no rupture |
| | citric 25 mg/NaCl 100 mg/PEO 205 68 mg/HPMC K4M 5.7 mg | 35 | 2/6 in the pass.-4/6 no rupture |
| | citric 30 mg/NaCl 100 mg/PEO 205 68 mg/HPMC K4M 5.7 mg | 35 | 2/6 big rupture in the pass.-4/6 no rupture |
| | citric 7 mg/NaCl 101.5 mg/PEO 205 99.75/HPMC K4M 5.7 mg | 35 | 4/6 small rupture-2/6 no rupture |
| | citric 7 mg/NaCl 101.5 mg/PEO 205 42.75/HPMC K4M 5.7 mg | 35 | 5/6 small rupture-1/6 no rupture |

(*) the tablets rupture in a location spaced away from the passageway, except in the cases indicated by the expression "in the pass", which means that the tablet ruptures at the edge of the preformed passageway.

EXAMPLE 8

The procedures herein can be used to determine the extent of swelling that the contents of a core (absent a membrane and subcoat) might undergo after exposure thereof to an aqueous medium.

A compressed core is placed in a graduated tube having a perforated bottom and/or water permeable membrane (or filtration medium) covered bottom. The initial volume (Vi) of the core is measured. Water or buffer is placed in contact with the perforated bottom or membrane such that water can wick into graduated tube and contact the compressed core. The core will equilibrate itself with the aqueous medium over a period of minutes to hours during which time it may swell and optionally one or more of its components may dissolve. After equilibration, the core will have finished expanding/swelling. The final volume (Vf) of the solids remaining settled at the bottom of the graduated tube is then measured. The ratio of Vf/Vi is determined.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A rupturing controlled release device comprising: a) a core comprising at least one active agent and at least one excipient; b) a semipermeable membrane enclosing the core and comprising a first cellulose acetate, a second cellulose acetate, a plasticizer, at least one preformed passageway there through, wherein the first cellulose acetate comprises 7-10% by weight of hydroxyl groups and 30-36% by weight of acetyl groups, and the second cellulose acetate comprises 3-5% by weight of hydroxyl groups and 37-43% by weight of acetyl groups, and a weakened region; and c) a rupture-controlling subcoat between the core and the semipermeable membrane and consisting essentially of hydroxypropyl methylcellulose and poly(ethylene glycol), wherein the semipermeable membrane ruptures at the weakened region during use due to the increase of the internal pressure of the device; the rupture-controlling subcoat reduces the size of a rupture initially formed in the semipermeable membrane during use as compared to an otherwise similar osmotic device comprising no rupture-controlling subcoat; the osmotic device continues to provide a controlled release of active agent from the core after rupture of the semipermeable membrane for a period of eight hours up to 12 hours, 16 hours, 18 hours, 20 hours, a day, or more than a day; and the invention does not include embodiments wherein the membrane breaks catastrophically thereby releasing the contents of the core in a burst or rapid manner.

2. The device of claim 1, wherein the membrane ruptures from one to twelve hours after exposure of the device to an environment of use.

3. The device of claim 1, wherein the weakened region is spaced away from the at least one preformed passageway to form a second passageway.

4. The device of claim 3, wherein the second passageway is initially formed from two to twelve hours after exposure of the device to an environment of use.

5. The device of claim 4, wherein
   i. the second passageway is smaller than or approximates the size of the at least one preformed passageway; or
   ii. the second passageway is larger than the at least one preformed passageway; or
   iii. the second passageway increases in size after initial formation.

6. The device of claim 1, wherein the weakened region is adjacent the passageway, and the at least one preformed passageway expands in size by rupture of the edge defining the at least one preformed passageway in the semipermeable membrane.

7. The device of claim 6, wherein the at least one preformed passageway increases in size by at least 10%, at least 25%, at least 50%, at least 75%, or at least 100%.

8. The device of claim 1, wherein the subcoat ranges in thickness from 0.05 mm to 0.5 mm.

9. The device of claim 1, wherein the membrane ranges in thickness from 0.075 mm to 1.5 mm.

10. The device of claim 1, wherein the weakened region is a scored region of the membrane.

11. The device of claim 1, wherein a batch of the devices exhibit a standard deviation in the range of ±0.05% to ±15% in the release profile of active agent from the core on a point-to-point or overall basis.

12. The device of claim 1 further comprising one or more coatings on the exterior of the semipermeable membrane, wherein the one or more coatings are independently selected at each occurrence from the group consisting of a drug-containing coating, a release rate modifying coating, a porous coating, a soluble coating, an insoluble coating, a semipermeable membrane; and a delayed release coating.

13. The device of claim 1 or 12 comprising an inert water soluble or erodible coat composition surrounding the semipermeable membrane.

14. The device of claim 12, wherein the drug-containing coating also comprises at least one preformed passageway.

15. The device of claim 12 wherein the one or more coatings are compression coatings and/or sprayed-on coatings and/or sprayed-on membranes.

16. The device of claim 1 or 12 comprising an optional inert water soluble or erodible coat composition surrounding the semipermeable membrane and comprising two external drug-containing layers in stacked arrangement with respect to and on opposite sides of the device.

17. The device of claim 1 or 12, comprising an optional inert water soluble or erodible coat composition surrounding the semipermeable membrane, wherein the core of the device is selected from the group consisting of a unitary core, a bi-layered core or a multi-layered core.

18. The device of claim 17, wherein the bi-layered core comprises the layers in stacked arrangement, substantially concentric arrangement, or substantially eccentric arrangement.

19. The device of claim 17, wherein the bi-layered core comprises a nucleus comprising an inert composition containing at least one swellable agent and a drug-containing layer surrounding the nucleus, or the bi-layered core comprises a first layer comprising the active agent an and a second layer comprising a swellable agent and an optional osmagent.

20. The device of claim 1, wherein the semipermeable membrane further comprises at least one porosigen agent.

21. The device of claim 1, wherein the release rate of active agent increases over time during use.

22. The device of claim 1, wherein at least 80% of the active agent is released by the end of use.

23. The device of claim 1, wherein the at least one preformed passageway is formed by mechanical means during manufacture of the osmotic device.

24. The device of claim 1, wherein the at least one preformed passageway is plugged with a soluble material that dissolves during use of the osmotic device.

25. The device of claim 1 or 12, comprising an optional inert water soluble or erodible coat composition surrounding the semipermeable membrane, wherein the core of the device is optionally selected from the group consisting of a unitary core, a bi-layered core or a multi-layered core, and wherein the active agent is independently selected at each occurrence from the group consisting of nutrients and nutritional agents, hematological agents, endocrine and metabolic agents, cardiovascular agents, renal and genitourinary agents, respiratory agents, central nervous system agents, gastrointestinal agents, anti-infective agents, biologic and immunological agents, dermatological agents, ophthalmic agents, antineoplastic agents, diagnostic agents, antibacterial substances, antiparasitic compounds, antiviral compounds, analgesic drugs, antihistamines and decongestants, antiasthma drugs, anticoagulants, psychic energizers, anticonvulsants, antidepressants, antidiabetics, steroidal drugs, estrogen antagonist-agonist drugs, antipsychotics, hypnotics and sedatives, anti-hypertensives, angiotensin converting enzyme inhibitors, tranquilizers, anti-spasmodics and muscle contractants, local anesthetics, muscle relaxants, anti-Parkinson, anti-dementia and anti-Alzheimer agent, sympathomimetics drugs, diuretics, β-blockers, α-blockers, phosphodiesterase inhibitors, antilipemic agents, electrolytes, drugs that act on α-adrenergic receptors, CNS stimulants, and unclassified therapeutic agents.

26. The device of claim 25, wherein the active agent is independently selected at each occurrence from the group consisting of albuterol, atenolol, acyclovir, amantadine, amlodipine, amoxicillin, acetaminophen, allopurinol, atorvastatin calcium, aspirin, alprazolam, azithromycin, caffeine, carbidopa, candesartan, carisoprodol, cimetidine, ciprofloxacin, citalopram, carbamazepine, carvedilol, celecoxib, clonazepam, clopidogrel, darifenacin, diazepam, doxazosin, enalapril, esomeprazole, eprosartan, fexofenadine, fluconazole, fluoxetine, galanthamine, gemfibrozil, felodipine, glipizide, glyburide, hydrochlorothiazide, ibuprofen, lamotrigine, lansoprazole, levodopa, loratadine, lorazepam, modafinil, memantine, mesalamine, metronidazole, naproxen, nifedipine, nisoldipine, olanzapine, omeprazole, olmersartan, paroxetine, phenylephrine, prednisone, pindolol, pioglitazone, quetiapine, raloxifene, ramipril, risperidone, rofecoxib, sertraline, sildenafil, simvastatin, tegaserod, temazepan, telmisartan, trazodone, triamterene, valsartan, vardenafil, venlafaxine, zolpidem and pharmaceutically acceptable salts thereof.

27. The device of claim 26 wherein the active agent is alprazolam.

28. The device of claim 26 wherein the active agent is sildenafil citrate.

29. The device of claim 1 or 12, comprising an optional inert water soluble or erodible coat composition surrounding the semipermeable membrane, wherein the core of the device is optionally selected from the group consisting of a unitary core, a bi-layered core or a multi-layered core and wherein:
   the core further comprises a surfactant, a diluent, an osmagent, and a binder.

30. The device of claim 29, wherein:
   the surfactant is selected from the group consisting of polysorbate, fatty amine oxides, fatty acid alkanolamides, and poly(oxyethylene)-block-poly(oxypropylene) copolymers, diethylene glycol monostearate, sodium lauryl sulfate, sorbitan monooleate, polyoxyethylene sorbitan fatty acid esters, polysorbate, bile salts, and glyceryl monostearate;
   the diluent is selected from the group consisting of microcrystalline cellulose, lactose, sucrose, mannitol, cellulose, starch, sorbitol, dibasic calcium phosphate, and calcium carbonate;
   the binder is selected from the group consisting of poly(vinylpyrrolidone), povidone, sodium carboxymethylcellulose, alginic acid, poly(ethylene glycol), guar gum, polysaccharide, bentonite clay, sugar, poloxamer, collagen, albumin, gelatin, poly(propylene glycol), and poly(ethylene oxide);

the osmagent is selected from the group consisting of sodium chloride, salt, mannitol, acid, sugar, base, calcium salt, sodium salt, and lactose;

the plasticizer is selected from the group consisting of poly(ethylene glycol), low molecular weight polymer, citrate ester, triacetin, propylene glycol, glycerin, sorbitol lactate, ethyl lactate, butyl lactate, ethyl glycolate, and dibutylsebacate.

31. The device of claim 29 further comprising at least one osmopolymer in the core.

32. The device of claim 31 wherein the osmopolymer is selected from the group consisting of hydroxylalkyl alkylcellulose, sodium carboxymethylcellulose, poly(vinylpyrrolidone), poly(hydroxy-alkyl methacrylates), poly(vinyl alcohol), polyethylene oxide, carbopol acidic carboxy polymer, and mixtures thereof.

33. The device of claim 32 wherein the hydroxylalkyl alkylcellulose is hydroxypropyl methylcellulose.

34. A rupturing controlled release device comprising: a) a core comprising sildenafil and at least one excipient; b) a semipermeable membrane enclosing the core and comprising a first cellulose acetate, a second cellulose acetate a plasticizer, at least one preformed passageway there through, wherein the first cellulose acetate comprises 7-10% by weight of hydroxyl groups and 30-36% by weight of acetyl groups, and the second cellulose acetate comprises 3-5% by weight of hydroxyl groups and 37-43% by weight of acetyl groups, and a weakened region; c) a rupture-controlling subcoat between the core and the semipermeable membrane wherein the subcoat consists essentially of hydroxypropyl methylcellulose, poly(ethylene glycol) and levodopa; and d) an external drug-containing coat comprising carbidopa, wherein the semipermeable membrane ruptures at the weakened region during use due to the increase of the internal pressure of the device; the rupture-controlling subcoat reduces the size of a rupture initially formed in the semipermeable membrane during use as compared to an otherwise similar osmotic device comprising no rupture-controlling subcoat; the osmotic device continues to provide a controlled release of active agent from the core after rupture of the semipermeable membrane for a period of eight hours up to 12 hours, 16 hours, 18 hours, 20 hours, a day, or more than a day; and the invention does not include embodiments wherein the membrane breaks catastrophically thereby releasing the contents of the core in a burst or rapid manner.

35. The device of claim 1 or 12, comprising an optional inert water soluble or erodible coat composition surrounding the semipermeable membrane, wherein the core of the device is optionally selected from the group consisting of a unitary core, a bi-layered core or a multi-layered core, and wherein the subcoat comprises one or more water soluble and/or erodible materials.

36. A rupturing controlled release device comprising:
a) a core comprising at least one active agent and at least one osmopolymer;
b) a semipermeable membrane enclosing the core and comprising a first cellulose acetate, a second cellulose acetate, a plasticizer, and at least one preformed passageway, wherein the first cellulose acetate comprises 7-10% by weight of hydroxyl groups and 30-36% by weight of acetyl groups, and the second cellulose acetate comprises 3-5% by weight of hydroxyl groups and 37-43% by weight of acetyl groups;
c) a weakened region in the membrane spaced away from or adjacent the preformed passageway; and
d) a rupture-controlling subcoat between the core and the semipermeable membrane, the subcoat consisting essentially hydroxypropyl methylcellulose and poly (ethylene glycol), wherein the membrane ruptures at the weakened region due to the increase of the internal pressure during use of the device to form a second passageway spaced away from the preformed passageway or to form a tear at the edge defining the preformed passageway thereby increasing the size of the preformed passageway, and the device provides a controlled release of the at least one active agent from the core after rupture of the semipermeable membrane; the rupture-controlling subcoat reduces the size of a rupture initially formed in the semipermeable membrane during use as compared to an otherwise similar osmotic device comprising no rupture-controlling subcoat; and the invention does not include embodiments wherein the membrane breaks catastrophically thereby releasing the contents of the core in a burst or rapid manner.

37. The device of claim 1, wherein the weakened region is spaced away from the preformed passageway, a second passageway is formed during use, and the second passageway ranges in size from 0.3 to 1.49 mm, 1.5 to 2.99 mm, 3 to 6 mm, or 0.3 to 6 mm.

38. The device of claim 1 or 12, comprising an optional inert water soluble or erodible coat composition surrounding the semipermeable membrane, wherein the core of the device is optionally selected from the group consisting of a unitary core, a bi-layered core or a multi-layered core, and wherein the core further comprises an acidic component.

39. The device of claim 1 or 12, comprising an optional inert water soluble or erodible coat composition surrounding the semipermeable membrane, wherein the core of the device is optionally selected from the group consisting of a unitary core, a bi-layered core or a multi-layered core, and wherein the core further comprises a swell-reducing agent.

40. The device of claim 39, wherein the swell-reducing agent is an organic acid.

41. The device of claim 40, wherein the swell-reducing agent is an organic acid selected from the group consisting of a non-aromatic carboxylic acid, a monocarboxylic acid, acetic acid, (+)-L-lactic acid, DL-lactic acid, L-mandelic acid, gluconic acid, cinnamic acid, salicylic acid, gentisic acid, a dicarboxylic acid, oxalic acid, 2-oxo-glutaric acid, malonic acid, (−)-L-malic acid, mucic acid, (+)-L-tartaric acid, fumaric acid, succinic acid, maleic acid, and terephthalic acid, a hydroxy-carboxylic acid, a hydroxy-dicarboxylic acid, a tricarboxylic acid, citric acid, aromatic carboxylic acid, sulfonic acids, methanesulfonic acid, benzenesulfonic acid, toluenesulfonic acid, napthalene-1,5-disulfonic acid, alpha-hydroxy acids, tartaric acid, citric acid, ascorbic acid and malic acid.

42. The device of claim 41, wherein the organic acid is tartaric acid or citric acid.

43. The device of claim 1 or 12, comprising an optional inert water soluble or erodible coat composition surrounding the semipermeable membrane, wherein the core of the device is optionally selected from the group consisting of a unitary core, a bi-layered core or a multi-layered core, and wherein the subcoat further comprises at least an active agent.

* * * * *